US006955879B2

(12) United States Patent
Lee et al.

(10) Patent No.: US 6,955,879 B2
(45) Date of Patent: Oct. 18, 2005

(54) METHOD FOR GENERATING RECOMBINANT DNA LIBRARY USING UNIDIRECTIONAL SINGLE-STRANDED DNA FRAGMENTS

(75) Inventors: Si-Hyoung Lee, Jinju-si (KR);
Yong-Chul Shin, Jinju-si (KR);
Yeong-Joong Jeon, Seoul (KR);
Kyung-Hwa Jung, Daejeon (KR);
Eun-Jung Ryu, Jinju-si (KR);
Ko-Woon Lee, Jinju-si (KR)

(73) Assignee: Amicogen, Inc. (KR)

( * ) Notice: Subject to any disclaimer, the term of this patent is extended or adjusted under 35 U.S.C. 154(b) by 669 days.

(21) Appl. No.: 10/148,724
(22) PCT Filed: Jun. 16, 2001
(86) PCT No.: PCT/KR01/01031

§ 371 (c)(1),
(2), (4) Date: May 28, 2002

(87) PCT Pub. No.: WO02/38757

PCT Pub. Date: May 16, 2002

(65) Prior Publication Data

US 2003/0152943 A1 Aug. 14, 2003

(51) Int. Cl.[7] .......................... C12Q 1/68; C12P 19/34; C12P 21/06
(52) U.S. Cl. ................. 435/6; 6/91.51; 6/69.1
(58) Field of Search .................. 435/6, 91.2, 69.1, 435/91.51

(56) References Cited

U.S. PATENT DOCUMENTS 5,965,408 A * 10/1999 Short .......................... 435/6

* cited by examiner

Primary Examiner—Kenneth R. Horlick
Assistant Examiner—Joyce Tung
(74) Attorney, Agent, or Firm—Anderson Kill & Olick; David A Einhorn

(57) ABSTRACT

The present invention relates to a method for producing a recombinant polynucleotides comprising the steps of generating a pool of unidirectional single-stranded polynucleotide fragments from two or more homologous double-stranded polynucleotides, conducting a polymerization process comprising multi-cyclic extension reactions using the unidirectional single-stranded polynucleotide fragments as templates and specific oligonucleotides as primers to obtain recombinant polynucleotides, and conducting a polymerase chain reaction using at least one primer to amplify the recombinant polynucleotides; and a method for constructing a recombinant DNA library comprising the steps of inserting the recombinant polynucleotide prepared by the above method into a vector and transforming an expression cell with said vector containing the recombinant polynucleotide to obtain a plurality of mutant clones. The method of the present invention can be used for in vitro recombination of homologous polynucleotides and the directed molecular evolution.

17 Claims, 24 Drawing Sheets

FIG. 2

```
l-chi   ATGCGCAAAT TTAATAAACC GCTGTTGGCG tTGcTGATCG GCAGCACGCT   50
m-chi   ATGCGCAAAT TTAATAAACC GCTGTTGGCG cTGtTGATCG GCAGCACGCT   50 l-chi   GTGcTCtGCG GCGCAGGCCG CtGCaCCGGG CAAaCCtACg tTgGCCTGGG   100
m-chi   GTGtTCcGCG GCGCAGGCCG CcGCgCCGGG CAAgCCgACc aTcGCCTGGG   100 l-chi   GCAAtACCAA aTTCGCCATt GTcGAAGTcG AtCAaGCGGC gACgGCTTAT   150
m-chi   GCAAcACCAA gTTCGCCATc GTtGAAGTtG AcCAgGCGGC tACcGCTTAT   150 l-chi   AATAATcTGG TGAAaGTAAA AAgTGCCGCC GAcGTTTCtG TtTCaTGGAA   200
m-chi   AATAATtTGG TGAAgGTAAA AAaTGCCGCC GAtGTTTCcG TcTCcTGGAA   200 l-chi   TTTATGGAAT GGCGAtaCcG GtACcACGGC aAAagTaTTA TTAAATGGcA   250
m-chi   TTTATGGAAT GGCGAcgCgG GcACgACGGC cAAgaTtTTA TTAAATGGtA   250 l-chi   AAGAaGttTG GAGTGGTgCc TCAACCGGta gTTCgGGaAC cGCaAAcTTT   300
m-chi   AAGAgGcgTG GAGTGGTcCt TCAACCGGat cTTCcGGtAC gGCgAAtTTT   300 l-chi   AAggtgaATA AAGGCGGCCG TTATCAAATG CAGGTGGCgT TaTGCAAcGC   350
m-chi   AAaagtgATA AAGGCGGCCG TTATCAAATG CAGGTGGcaT TgTGCAAtGC   350 l-chi   CGACGGCTGt ACCGCCAGcG AtGCaACCGA AATTGTGGTG GCaGAtACCG   400
m-chi   CGACGGCTGc ACCGCCAGtG AcGCcACCGA AATTGTGGTG GCcGAcACCG   400 l-chi   ACGGtAGCCA TTTGGCaCCt TTaAAAGAaC CttTGttGGA AAAGAATAAg   450
m-chi   ACGGcAGCCA TTTGGCgCCg TTgAAAGAgC CgcTGcTGGA AAAGAATAAa   450 l-chi   CCtTATAAAC AagACTCCGG CAAAGTGGTt GGcTCTTATT TCGTtGAaTG   500
m-chi   CCgTATAAAC AgaACTCCGG CAAAGTGGTc GGtTCTTATT TCGTcGAgTG   500 l-chi   GGGCGTTTAC GGcCGtAATT TCACCGTCGA tAAacTtCCG GCtCAgAACC   550
m-chi   GGGCGTTTAC GGgCGcAATT TCACCGTCGA cAAgaTcCCG GCgCAaAACC   550 l-chi   TGACgCACCT GCTGTACGGC TTTATCCCtA TCTGtGGCGG tgAcGGCATC   600
m-chi   TGACcCACCT GCTGTACGGC TTTATCCCgA TCTGcGGCGG caAtGGCATC   600 l-chi   AACGACAGCC TGAAAGAGAT cGAAGGCAGC TTCCAGGCGT TACAGCGtTC   650
m-chi   AACGACAGCC TGAAAGAGAT tGAAGGCAGC TTCCAGGCGT TACAGCGcTC   650 l-chi   CTGtCAGGGg CGtGAaGACT TtAAgGTaTC GaTCCACGAT CCGTTCGCtG   700
m-chi   CTGcCAGGGc CGcGAgGACT TcAAaGTcTC GgTCCACGAT CCGTTCGCcG   700 l-chi   CGCTGCAgAA AGgtCAGAAG GGCGTGACCG CCTGGGAcGA CCCCTACAAa   750
m-chi   CGCTGCAaAA AGcgCAGAAG GGCGTGACCG CCTGGGAtGA CCCCTACAAg   750 l-chi   GGCAACTTCG GCCAGtTGAT GGCGtTGAAa CAGGCGCgcC CgGACCTGAA   800
m-chi   GGCAACTTCG GCCAGcTGAT GGCGcTGAAg CAGGCGCatC CtGACCTGAA   800 l-chi   AATCCTGCCG TCGATCGGtG GCTGGACGtT aTCCGAtCCG TTCTTCTTtA   850
m-chi   AATCCTGCCG TCGATCGGcG GCTGGACGcT gTCCGAcCCG TTCTTCTTcA   850
```

FIG. 2 (continued)

```
l-chi   TGGGCGAtAA GGTGAAGCGC GATCGCTTCG TCGGcTCGGT GAAgGAGTTC   900
m-chi   TGGGCGAcAA GGTGAAGCGC GATCGCTTCG TCGGtTCGGT GAAaGAGTTC   900 l-chi   CTGCAaACCT GGAAGTTCTT tGAtGGCGTa GATATCGACT GGGAaTTCCC   950
m-chi   CTGCAgACCT GGAAGTTCTT cGAcGGCGTg GATATCGACT GGGAgTTCCC   950 l-chi   GGGCGGgcAg GGtGCtAACC CgAAaCTGGG CAGtaCGCAg GAtGGGGcAA   1000
m-chi   GGGCGGcaAa GGcGCcAACC CtAAcCTGGG CAGccCGCAa GAcGGGGaAA   1000 l-chi   CCTATGTGca GCTGATGAAa GAGCTGCGcG CcATGCTGGA TCAGCTtTCG   1050
m-chi   CCTATGTGtt GCTGATGAAg GAGCTGCGgG CgATGCTGGA TCAGCTgTCG   1050 l-chi   GCGGAAACgG GCCGtAAGTA TGAaCTGACC TCtGCgATCA GCGCCGGcAA   1100
m-chi   GCGGAAACcG GCCGcAAGTA TGAgCTGACC TCcGCcATCA GCGCCGGtAA   1100 l-chi   GGAtAAaATC GAtAAGGTGG aTTACAACac cGCaCAaAAC TCGATGGATC   1150
m-chi   GGAcAAgATC GAcAAGGTGG cTTACAACgt tGCgCAgAAC TCGATGGATC   1150 l-chi   ACATtTTCCT GATGAGtTAC GACTTCTATG GgGCaTTCGA TCTGAAaAAt   1200
m-chi   ACATcTTCCT GATGAGcTAC GACTTCTATG GcGCcTTCGA TCTGAAgAAc   1200 l-chi   CTGGGcCAcC AGACtGCGCT GAAaGCGCCG GCCTGGAAaC CGGAtACgGC   1250
m-chi   CTGGGgCAtC AGACcGCGCT GAAtGCGCCG GCCTGGAAgC CGGAcACcGC   1250 l-chi   gTAtACCACG GTGAAtGGCG TtAATGCaCT GCTcaCGCAG GGCGTgAAGC   1300
m-chi   tTAcACCACG GTGAAcGGCG TcAATGCgCT GCTggCGCAG GGCGTcAAGC   1300 l-chi   CGGGCAAaAT CGTGGTgGGC ACCGCCATGT AcGGtCGCGG tTGGACCGGG   1350
m-chi   CGGGCAAgAT CGTGGTcGGC ACCGCCATGT AtGGcCGCGG cTGGACCGGG   1350 l-chi   GTGAACGGtT ACCAGAACAA CATTCCGTTt ACCGGcACCG CCACTGGcCC   1400
m-chi   GTGAACGGcT ACCAGAACAA CATTCCGTTc ACCGGtACCG CCACTGGgCC   1400 l-chi   GGTgAAAGGC ACCTGGGAaA AtGGCATCGT GGAtTACCGC CAgATCGCCa   1450
m-chi   GGTtAAAGGC ACCTGGGAgA AcGGCATCGT GGAcTACCGC CAaATCGCCg   1450 l-chi   atgAGTTtAT GAGCGGCGAa TGGCAGTAcA gCTACGAtGC tACcGCtGAA   1500
m-chi   gccAGTTcAT GAGCGGCGAg TGGCAGTAtA cCTACGAcGC cACgGCgGAA   1500 l-chi   GCaCCcTAtG TcTTCAAACC TTCCACtGGC GATCTGATCA CCTTCGACGA   1550
m-chi   GCgCCtTAcG TgTTCAAACC TTCCACcGGC GATCTGATCA CCTTCGACGA   1550 l-chi   TGCgCGCTCG GTGCAGGCgA AgGGCAAaTA tGTGCTGGAT AAGCAGCTGG   1600
m-chi   TGCcCGCTCG GTGCAGGCcA AaGGCAAgTA cGTGCTGGAT AAGCAGCTGG   1600 l-chi   GCGGgtTGTT CTCaTGGGAa ATtGACGCcG AcAACGGCGA TATTCTgAAt   1650
m-chi   GCGGccTGTT CTCcTGGGAg ATcGACGCgG AtAACGGCGA TATTCTcAAc   1650 l-chi   AaCATGAACa gCAGCCTGGG CAACAGCGtC GGtacgCctT AA            1692
m-chi   AgCATGAACg cCAGCCTGGG CAACAGCGcC GGcgttCaaT AA            1692
```

FIG. 5

```
1-chi    ATGCGCAAATTTAATAAACCGCTGTTGGCGTTGCTGATCGGCAGCACGCTGTGCTCTGCG 60
m-chi    ATGCGCAAATTTAATAAACCGCTGTTGGCGCTGTTGATCGGCAGCACGCTGTGTTCCGCG 60
mut-1    ATGCGCAAATTTAATAAACCGCTGTTGGCGTTGCTGATCGGCAGCACGCTGTGCTCTGCG 60
mut-2    ATGCGCAAATTTAATAAACCGCTGTTGGCGTTGCTGATCGGCAGCACGCTGTGCTCTGCG 60
mut-3    ATGCGCAAATTTAATAAACCGCTGTTGGCGCTGTTGATCGGCAGCACGCTGTGTTCCGCG 60
mut-4    ATGCGCAAATTTAATAAACCGCTGTTGGCGCTGTTGATCGGCAGCACGCTGTGTTCCGCG 60
mut-5    ATGCGCAAATTTAATAAACCGCTGTTGGCGCTGTTGATCGGCAGCACGCTGTGTTCCGCG 60
mut-6    ATGCGCAAATTTAATAAACCGCTGTTGGCGCTGTTGATCGGCAGCACGCTGTGTTCCGCG 60
mut-7    ATGCGCAAATTTAATAAACCGCTGTTGGCGTTGCTGATCGGCAGCACGCTGTGCTCTGCG 60
mut-8    ATGCGCAAATTTAATAAACCGCTGTTGGCGCTGTTGATCGGCAGCACGCTGTGTTCCGCG 60
mut-9    ATGCGCAAATTTAATAAACCGCTGTTGGCGCTGTTGATCGGCAGCACGCTGTGTTCCGCG 60
mut-10   ATGCGCAAATTTAATAAACCGCTGTTGGCGCTGTTGATCGGCAGCACGCTGTGTTCCGCG 60

1-chi    GCGCAGGCCGCTGCACCGGGCAAACCTACGTTGGCCTGGGGCAATACCAAATTCGCCATT 120
m-chi    GCGCAGGCCGCCGCGCCGGGCAAGCCGACCATCGCCTGGGGCAACACCAAGTTCGCCATC 120
mut-1    GCGCAGGCCGCTGCACCGGGCAAACCTACGTTGGCCTGGGGCAATACCAAATTCGCCATT 120
mut-2    GCGCAGGCCGCTGCACCGGGCAAACCTACGTTGGCCTGGGGCAATACCAAATTCGCCATT 120
mut-3    GCGCAGGCCGCCGCGCCGGGCAAGCCGACCATCGCCTGGGGCAACACCAAGTTCGCCATC 120
mut-4    GCGCAGGCCGCCGCGCCGGGCAAGCCGACCATCGCCTGGGGCAACACCAAGTTCGCCATC 120
mut-5    GCGCAGGCCGCCGCGCCGGGCAAGCCGACCATCGCCTGGGGCAACACCAAGTTCGCCATC 120
mut-6    GCGCAGGCCGCCGCGCCGGGCAAGCCGACCATCGCCTGGGGCAACACCAAGTTCGCCATC 120
mut-7    GCGCAGGCCGCTGCACCGGGCAAACCTACGTTGGCCTGGGGCAATACCAAATTCGCCATT 120
mut-8    GCGCAGGCCGCCGCGCCGGGCAAGCCGACCATCGCCTGGGGCAACACCAAGTTCGCCATC 120
mut-9    GCGCAGGCCGCCGCGCCGGGCAAGCCGACCATCGCCTGGGGCAACACCAAGTTCGCCATC 120
mut-10   GCGCAGGCCGCCGCGCCGGGCAAGCCGACCATCGCCTGGGGCAACACCAAGTTCGCCATC 120

1-chi    GTCGAAGTCGATCAAGCGGCGACGGCTTATAATAATCTGGTGAAAGTAAAAAGTGCCGCC 180
m-chi    GTTGAAGTTGACCAGGCGGCTACCGCTTATAATAATTTGGTGAAGGTAAAAAATGCCGCC 180
mut-1    GTCGAAGTCGATCAAGCGGCGACGGCTTATAATAATCTGGTGAAAGTAAAAAGTGCCGCC 180
mut-2    GTCGAAGTCGATCAAGCGGCGACGGCTTATAATAATCTGGTGAAAGTAAAAAGTGCCGCC 180
mut-3    GTTGAAGTTGACCAGGCGGCTACCGCTTATAATAATTTGGTGAAGGTAAAAAATGCCGCC 180
mut-4    GTTGAAGTTGACCAGGCGGCTACCGCTTATAATAATTTGGTGAAGGTAAAAAATGCCGCC 180
mut-5    GTTGAAGTTGACCAGGCGGCTACCGCTTATAATAATTTGGTGAAGGTAAAAAATGCCGCC 180
mut-6    GTTGAAGTTGACCAGGCGGCTACCGCTTATAATAATTTGGTGAAGGTAAAAAATGCCGCC 180
mut-7    GTCGAAGTCGATCAAGCGGCGACGGCTTATAATAATCTGGTGAAAGTAAAAAGTGCCGCC 180
mut-8    GTTGAAGTTGACCAGGCGGCTACCGCTTATAATAATTTGGTGAAGGTAAAAAATGCCGCC 180
mut-9    GTTGAAGTTGATCAAGCGGCGACGGCTTATAATAATCTGGTGAAAGTAAAAAGTGCCGCC 180
mut-10   GTTGAAGTTGACCAGGCGGCTACCGCTTATAATAATTTGGTGAAGGTAAAAAATGCCGCC 180
```

FIG. 5 (continued)

```
l-chi    GACGTTTCTGTTTCATGGAATTTATGGAATGGCGATACCGGTACCACGGCAAAAGTATTA 240
m-chi    GATGTTTCCGTCTCCTGGAATTTATGGAATGGCGACGCGGGCACGACGGCCAAGATTTTA 240
mut-1    GACGTTTCTGTTTCATGGAATTTATGGAATGGCGATACCGGTACCACGGCAAAAGTATTA 240
mut-2    GACGTTTCTGTTTCATGGAATTTATGGAATGGCGATACCGGTACCACGGCAAAAGTATTA 240
mut-3    GATGTTTCCGTCTCCTGGAATTTATGGAATGGCGACGCGGGCACGACGGCCAAGATTTTA 240
mut-4    GATGTTTCCGTCTCCTGGAATTTATGGAATGGCGACGCGGGCACGACGGCCAAGATTTTA 240
mut-5    GATGTTTCCGTCTCCTGGAATTTATGGAATGGCGACGCGGGCACGACGGCCAAGATTTTA 240
mut-6    GATGTTTCCGTCTCCTGGAATTTATGGAATGGCGACGCGGGCACGACGGCCAAGATTTTA 240
mut-7    GACGTTTCTGTTTCATGGAATTTATGGAATGGCGATACCGGTACCACGGCAAAAGTATTA 240
mut-8    GATGTTTCCGTCTCCTGGAATTTATGGAATGGCGACGCGGGCACGACGGCCAAGATTTTA 240
mut-9    GACGTTTCTGTTTCATGGAATTTATGGAATGGCGATACCGGTACCACGGCAAAAGTATTA 240
mut-10   GATGTTTCCGTCTCCTGGAATTTATGGAATGGCGACGCGGGCACGACGGCCAAGATTTTA 240 l-chi    TTAAATGGCAAAGAAGTTTGGAGTGGTGCCTCAACCGGTAGTTCGGGAACCGCAAACTTT 300
m-chi    TTAAATGGTAAAGAGGCGTGGAGTGGTCCTTCAACCGGATCTTCCGGTACGGCGAATTTT 300
mut-1    TTAAATGGCAAAGAAGTTTGGAGTGGTGCCTCAACCGGTAGTTCGGGAACCGCAAACTTT 300
mut-2    TTAAATGGCAAAGAAGTTTGGAGTGGTGCCTCAACCGGTAGTTCGGGAACCGCAAACTTT 300
mut-3    TTAAATGGTAAAGAGGCGTGGAGTGGTCCTTCAACCGGATCTTCCGGTACGGCGAATTTT 300
mut-4    TTAAATGGTAAAGAGGCGTGGAGTGGTCCTTCAACCGGATCTTCCGGTACGGCGAATTTT 300
mut-5    TTAAATGGTAAAGAGGCGTGGAGTGGTCCTTCAACCGGATCTTCCGGTACGGCGAATTTT 300
mut-6    TTAAATGGTAAAGAGGCGTGGAGTGGTCCTTCAACCGGATCTTCCGGTACGGCGAATTTT 300
mut-7    TTAAATGGCAAAGAAGTTTGGAGTGGTGCCTCAACCGGTAGTTCGGGAACCGCAAACTTT 300
mut-8    TTAAATGGTAAAGAGGCGTGGAGTGGTCCTTCAACCGGATCTTCCGGTACGGCGAATTTT 300
mut-9    TTAAATGGCAAAGAAGTTTAGAGTGGTGCCTCAACCGGTAGTTCGGGAACCGCAAACTTT 300
mut-10   TTAAATGGTAAAGAGGCGTGGAGTGGTCCTTCAACCGGATCTTCCGGTACGGCGAATTTT 300 l-chi    AAGGTGAATAAAGGCGGCCGTTATCAAATGCAGGTGGCGTTATGCAACGCCGACGGCTGT 360
m-chi    AAAGTGAATAAAGGCGGCCGTTATCAAATGCAGGTGGCATTGTGCAATGCCGACGGCTGC 360
mut-1    AAGGTGAATAAAGGCGGCCGTTATCAAATGCAGGTGGCGTTATGCAACGCCGACGGCTGT 360
mut-2    AAGGTGAATAAAGGCGGCCGTTATCAAATGCAGGTGGCGTTATGCAACGCCGACGGCTGT 360
mut-3    AAAGTGAATAAAGGCGGCCGTTATCAAATGCAGGTGGCATTGTGCAATGCCGACGGCTGC 360
mut-4    AAAGTGAATAAAGGCGGCCGTTATCAAATGCAGGTGGCATTGTGCAATGCCGACGGCTGC 360
mut-5    AAAGTGAATAAAGGCGGCCGTTATCAAATGCAGGTGGCATTGTGCAATGCCGACGGCTGC 360
mut-6    AAAGTGAATAAAGGCGGCCGTTATCAAATGCAGGTGGCATTGTGCAATGCCGACGGCTGC 360
mut-7    AAGGTGAATAAAGGCGGCCGTTATCAAATGCAGGTGGCGTTATGCAACGCCGACGGCTGT 360
mut-8    AAAGTGAATAAAGGCGGCCGTTATCAAATGCAGGTGGCGTTATGCAACGCCGACGGCTGT 360
mut-9    AAGGTGAATAAAGGCGGCCGTTATCAAATGCAGGTGGCGTTATGCAACGCCGACGGCTGT 360
mut-10   AAAGTGAATAAAGGCGGCCGTTATCAAATGCAGGTGGCATTGTGCAATGCCGACGGCTGC 360
```

FIG. 5 (continued)

```
l-chi    ACCGCCAGCGATGCAACCGAAATTGTGGTGGCAGATACCGACGGTAGCCATTTGGCACCT 420
m-chi    ACCGCCAGTGACGCCACCGAAATTGTGGTGGCCGACACCGACGGCAGCCATTTGGCGCCG 420
mut-1    ACCGCCAGCGATGCAACCGAAATTGTGGTGGCAGATACCGACGGTAGCCATTTGGCACCT 420
mut-2    ACCGCCAGCGATGCAACCGAAATTGTGGTGGCAGATACCGACGGTAGCCATTTGGCACCT 420
mut-3    ACCGCCAGTGACGCCACCGAAATTGTGGTGGCCGACACCGACGGCAGCCATTTGGCGCCG 420
mut-4    ACCGCCAGTGACGCCACCGAAATTGTGGTGGCCGACACCGACGGCAGCCATTTGGCGCCG 420
mut-5    ACCGCCAGTGACGCCACCGAAATTGTGGTGGCCGACACCGACGGCAGCCATTTGGCGCCG 420
mut-6    ACCGCCAGTGACGCCACCGAAATTGTGGTGGCAGATACCGACGGTAGCCATTTGGCACCT 420
mut-7    ACCGCCAGCGATGCAACCGAAATTGTGGTGGCAGATACCGACGGTAGCCATTTGGCACCT 420
mut-8    ACCGCCAGCGATGCAACCGAAATTGTGGTGGCCGACACCGACGGCAGCCATTTGGCGCCG 420
mut-9    ACCGCCAGCGATGCAACCGAAATTGTGGTGGCAGATACCGACGGTAGCCATTTGGCACCT 420
mut-10   ACCGCCAGTGACGCCACCGAAATTGTGGTGGCCGACACCGACGGCAGCCATTTGGCGCCG 420 l-chi    TTAAAAGAACCTTTGTTGGAAAAGAATAAGCCTTATAAACAAGACTCCGGCAAAGTGGTT 480
m-chi    TTGAAAGAGCCGCTGCTGGAAAAGAATAAACCGTATAAACAGAACTCCGGCAAAGTGGTC 480
mut-1    TTAAAAGAACCTTTGTTGGAAAAGAATAAGCCTTATAAACAAGACTCCGGCAAAGTGGTC 480
mut-2    TTAAAAGAACCTTTGTTGGAAAAGAATAAGCCTTATAAACAAGACTCCGGCAAAGTGGTT 480
mut-3    TTGAAAGAGCCGCTGCTGGAAAAGAATAAACCGTATAAACAGAACTCCGGCAAAGTGGTC 480
mut-4    TTGAAAGAGCCGCTGCTGGAAAAGAATAAACCGTATAAACAGAACTCCGGCAAAGTGGTC 480
mut-5    TTGAAAGAGCCGCTGCTGGAAAAGAATAAACCGTATAAACAGAACTCCGGCAAAGTGGTC 480
mut-6    TTAAAAGAACCTTTGTTGGAAAAGAATAAGCCTTATAAACAAGACTCCGGCAAAGTGGTT 480
mut-7    TTAAAAGAACCTTTGTTGGAAAAGAATAAGCCTTATAAACAAGACTCCGGCAAAGTGGTT 480
mut-8    TTGAAAGAGCCGCTGCTGGAAAAGAATAAACCGTATAAACAGAACTCCGGCAAAGTGGTC 480
mut-9    TTAAAAGAACCTTTGTTGGAAAAGAATAAGCCTTATAAACAAGACTCCGGCAAAGTGGTT 480
mut-10   TTGAAAGAGCCGCTGCTGGAAAAGAATAAACCGTATAAACAGAACTCCGGCAAAGTGGTC 480 l-chi    GGCTCTTATTTCGTTGAATGGGGCGTTTACGGCCGTAATTTCACCGTCGATAAACTTCCG 540
m-chi    GGTTCTTATTTCGTCGAGTGGGGCGTTTACGGGCGCAATTTCACCGTCGACAAGATCCCG 540
mut-1    GGTTCTTATTTCGTCGAGTGGGGCGTTTACGGGCGCAATTTCACCGTCGACAAGATCCCG 540
mut-2    GGCTCTTATTTCGTTGAATGGGGCGTTTACGGCCGTAATTTCACCGTCGATAAACTTCCG 540
mut-3    GGTTCTTATTTCGTCGAGTGGGGCGTTTACGGGCGCAATTTCACCGTCGACAAGATCCCG 540
mut-4    GGTTCTTATTTCGTCGAGTGGGGCGTTTACGGGCGCAATTTCACCGTCGACAAGATCCCG 540
mut-5    GGTTCTTATTTCGTCGAGTGGGGCGTTTACGGCCGTAATTTCACCGTCGATAAACTTCCG 540
mut-6    GGCTCTTATTTCGTTGAATGGGGCGTTTACGGCCGTAATTTCACCGTCGATAAACTTCCG 540
mut-7    GGCTCTTATTTCGTTGAATGGGGCGTTTACGGCCGTAATTTCACCGTCGATAAACTTCCG 540
mut-8    GGTTCTTATTTCGTCGAGTGGGGCGTTTACGGGCGCAATTTCACCGTCGACAAGATCCCG 540
mut-9    GGCTCTTATTTCGTTGAATGGGGCGTTTACGGCCGTAATTTCACCGTCGATAAACTTCCG 540
mut-10   GGTTCTTATTTCGTCGAGTGGGGCGTTTACGGGCGCAATTTCACCGTCGACAAGATCCCG 540
```

FIG. 5 (continued)

```
1-chi    GCTCAGAACCTGACGCACCTGCTGTACGGCTTTATCCCTATCTGTGGCGGTGACGGCATC  600
m-chi    GCGCAAAACCTGACCCACCTGCTGTACGGCTTTATCCCGATCTGCGGCGGCAATGGCATC  600
mut-1    GCTCAGAACCTGACGCACCTGCTGTACGGCTTTATCCCTATCTGTGGCGGTGACGGCATC  600
mut-2    GCTCAGAACCTGACGCACCTGCTGTACGGCTTTATCCCTATCTGTGGCGGTGACGGCATC  600
mut-3    GCGCAAAACCTGACCCACCTGCTGTACGGCTTTATCCCGATCTGCGGCGGCAATGGCATC  600
mut-4    GCGCAAAACCTGACCCACCTGCTGTACGGCTTTATCCCTATCTGTGGCGGTGACGGCATC  600
mut-5    GCTCAGAACCTGACGCACCTGCTGTACGGCTTTATCCCTATCTGTGGCGGTGACGGCATC  600
mut-6    GCTCAGAACCTGACGCACCTGCTGTACGGCTTTATCCCTATCTGTGGCGGTGACGGCATC  600
mut-7    GCTCAGAACCTGACGCACCTGCTGTACGGCTTTATCCCTATCTGTGGCGGTGACGGCATC  600
mut-8    GCGCAAAACCTGACCCACCTGCTGTACGGCTTTATCCCGATCTGCGGCGGCAATGGCATC  600
mut-9    GCTCAGAACCTGACGCACCTGCTGTACGGCTTTATCCCTATCTGTGGCGGTGACGGCATC  600
mut-10   GCGCAGAACCTGACGCACCTGCTGTACGGCTTTATCCCGATCTGCGGCGGTGATGGCATC  600

1-chi    AACGACAGCCTGAAAGAGATCGAAGGCAGCTTCCAGGCGTTACAGCGTTCCTGTCAGGGG  660
m-chi    AACGACAGCCTGAAAGAGATTGAAGGCAGCTTCCAGGCGTTACAGCGCTCCTGCCAGGGC  660
mut-1    AACGACAGCCTGAAAGAGATCGAAGGCAGCTTCCAGGCGTTACAGCGTTCCTGTCAGGGG  660
mut-2    AACGACAGCCTGAAAGAGATCGAAGGCAGCTTCCAGGCGTTACAGCGTTCCTGTCAGGGG  660
mut-3    AACGACAGCCTGAAAGAGATTGAAGGCAGCTTCCAGGCGTTACAGCGCTCCTGCCAGGGC  660
mut-4    AACGACAGCCTGAAAGAGATCGAAGGCAGCTTCCAGGCGTTACAGCGTTCCTGTCAGGGG  660
mut-5    AACGACAGCCTGAAAGAGATCGAAGGCAGCTTCCAGGCGTTACAGCGTTCCTGTCAGGGG  660
mut-6    AACGACAGCCTGAAAGAGATTGAAGGCAGCTTCCAGGCGTTACAGCGTTCCTGTCAGGGG  660
mut-7    AACGACAGCCTGAAAGAGATCGAAGGCAGCTTCCAGGCGTTACAGCGTTCCTGTCAGGGG  660
mut-8    AACGACAGCCTGAAAGAGATTGAAGGCAGCTTCCAGGCGTTACAGCGCTCCTGCCAGGGC  660
mut-9    AACGACAGCCTGAAAGAGATCGAAGGCAGCTTCCAGGCGTTACAGCGTTCCTGTCAGGGG  660
mut-10   AACGACAGCCTGAAAGAGATCGAAGGCAGCTTCCAGGCGTTACAGCGCTCCTGTCAGGGG  660

1-chi    CGTGAAGACTTTAAGGTATCGATCCACGATCCGTTCGCTGCGCTGCAGAAAGGTCAGAAG  720
m-chi    CGCGAGGACTTCAAAGTCTCGGTCCACGATCCGTTCGCCGCGCTGCAAAAAGCGCAGAAG  720
mut-1    CGTGAAGACTTTAAGGTATCGATCCACGATCCGTTCGCTGCGCTGCAGAAAGGTCAGAAG  720
mut-2    CGTGAAGACTTTAAGGTATCGATCCACGATCCGTTCGCTGCGCTGCAGAAAGGTCAGAAG  720
mut-3    CGCGAGGACTTCAAAGTCTCGGTCCACGATCCGTTCGCCGCGCTGCAAAAAGCGCAGAAG  720
mut-4    CGTGAAGACTTTAAGGTATCGATCCACGATCCGTTCGCTGCGCTGCAGAAAGGTCAGAAG  720
mut-5    CGTGAAGACTTTAAGGTATCGATCCACGATCCGTTCGCTGCGCTGCAGAAAGGTCAGAAG  720
mut-6    CGTGAAGACTTTAAGGTATCGATCCACGATCCGTTCGCTGCGCTGCAGAAAGGTCAGAAG  720
mut-7    CGTGAAGACTTTAAGGTATCGATCCACGATCCGTTCGCCGCGCTGCAAAAAGCGCAGAAG  720
mut-8    CGCGAGGACTTCAAAGTCTCGGTCCACGATCCGTTCGCCGCGCTGCAAAAAGCGCAGAAG  720
mut-9    CGTGAAGACTTTAAGGTATCGATCCACGATCCGTTCGCTGCGCTGCCGAAAGGTCAGAAG  720
mut-10   CGCGAAGACTTCAAGGTATCGGTCCACGATCCGTTCGCCGCGCTGCAGAAAGGGCAGAAG  720
```

FIG. 5(continued)

```
1-chi    GGCGTGACCGCCTGGGACGACCCCTACAAAGGCAACTTCGGCCAGTTGATGGCGTTGAAA 780
m-chi    GGCGTGACCGCCTGGGATGACCCCTACAAGGGCAACTTCGGCCAGCTGATGGCGCTGAAG 780
mut-1    GGCGTGACCGCCTGGGACGACCCCTACAAAGGCAACTTCGGCCAGTTGATGGCGTTGAAA 780
mut-2    GGCGTGACCGCCTGGGACGACCCCTACAAAGGCAACTTCGGCCAGTTGATGGCGTTGAAA 780
mut-3    GGCGTGACCGCCTGGGATGACCCCTACAAGGGCAACTTCGGCCAGCTGATGGCGCTGAAG 780
mut-4    GGCGTGACCGCCTGGGACGACCCCTACAAAGGCAACTTCGGCCAGTTGATGGCGTTGAAA 780
mut-5    GGCGTGACCGCCTGGGACGACCCCTACAAAGGCAACTTCGGCCAGTTGATGGCGTTGAAA 780
mut-6    GGCGTGACCGCCTGGGACGACCCCTACAAAGGCAACTTCGGCCAGTTGATGGCGTTGAAA 780
mut-7    GGCGTGACCGCCTGGGATGACCCCTACAAGGGCAACTTCGGCCAGCTGATGGCGCTGAAG 780
mut-8    GGCGTGACCGCCTGGGATGACCCCTACAAGGGCAACTTCGGCCAGCTGATGGCGCTGAAG 780
mut-9    GGCGTGACCGCCTGGGACGACCCCTACAAAGGCAACTTCGGCCAGTTGATGGCGTTGAAA 780
mut-10   GGCGTGACCGCCTGGGACGACCCCTACAAGGGCAACTTCGGCCAGCTGATGGCGCTGAAG 780

1-chi    CAGGCGCGCCCGGACCTGAAAATCCTGCCGTCGATCGGTGGCTGGACGTTATCCGATCCG 840
m-chi    CAGGCGCATCCTGACCTGAAAATCCTGCCGTCGATCGGCGGCTGGACGCTGTCCGACCCG 840
mut-1    CAGGCGCGCCCGGACCTGAAAATCCTGCCGTCGATCGGTGGCTGGACGTTATCCGATCCG 840
mut-2    CAGGCGCGCCCGGACCTGAAAATCCTGCCGTCGATCGGTGGCTGGACGTTATCCGATCCG 840
mut-3    CAGGCGCATCCTGACCTGAAAATCCTGCCGTCGATCGGCGGCTGGACGTTATCCGATCCG 840
mut-4    CAGGCGCGCCCGGACCTGAAAATCCTGCCGTCGATCGGTGGCTGGACGTTATCCGATCCG 840
mut-5    CAGGCGCGCCCGGACCTGAAAATCCTGCCGTCGATCGGTGGCTGGACGTTATCCGATCCG 840
mut-6    CAGGCGCGCCCGGACCTGAAAATCCTGCCGTCGATCGGTGGCTGGACGTTATCCGATCCG 840
mut-7    CAGGCGCATCCTGACCTGAAAATCCTGCCGTCGATCGGCGGCTGGACGCTGTCCGACCCG 840
mut-8    CAGGCGCATCCTGACCTGAAAATCCTGCCGTCGATCGGCGGCTGGACGCTGTCCGACCCG 840
mut-9    CAGGCGCGCCCGGACCTGAAAATCCTGCCGTCGATCGGTGGCTGGACGTTATCCGATCCG 840
mut-10   CAGGCGCGCCCGGACCTGAAAATCCTGCCGTCGATCGGTGGCTGGACGTTATCCGATCCG 840

1-chi    TTCTTCTTTATGGGCGATAAGGTGAAGCGCGATCGCTTCGTCGGCTCGGTGAAGGAGTTC 900
m-chi    TTCTTCTTCATGGGCGACAAGGTGAAGCGCGATCGCTTCGTCGGTTCGGTGAAAGAGTTC 900
mut-1    TTCTTCTTTATGGGCGATAAGGTGAAGCGCGATCGCTTCGTCGGCTCGGTGAAGGAGTTC 900
mut-2    TTCTTCTTTATGGGCGATAAGGTGAAGCGCGATCGCTTCGTCGGCTCGGTGAAAGAGTTC 900
mut-3    TTCTTCTTTATGGGCGATAAGGTGAAGCGCGATCGCTTCGTCGGCTCGGTGAAGGAGTTC 900
mut-4    TTCTTCTTTATGGGCGATAAGGTGAAGCGCGATCGCTTCGTCGGCTCGGTGAAGGAGTTC 900
mut-5    TTCTTCTTTATGGGCGATAAGGTGAAGCGCGATCGCTTCGTCGGCTCGGTGAAAGAGTTC 900
mut-6    TTCTTCTTTATGGGCGACAAGGTGAAGCGCGATCGCTTCGTCGGTTCGGTGAAAGAGTTC 900
mut-7    TTCTTCTTCATGGGCGACAAGGTGAAGCGCGATCGCTTCGTCGGTTCGGTGAAAGAGTTC 900
mut-8    TTCTTCTTAATGGGCGACAAGGTGAAGCGCGATCGCTTCGTCGGTTCGGTGAAAGAGTTC 900
mut-9    TTCTTCTTTATGGGCGATAAGGTGAAGCGCGATCGCTTCGTCGGCTCGGTGAAGGAGTTC 900
mut-10   TTCTTCTTTATGGGCGATAAGGTGAAGCGCGATCGCTTCGTCGGCTCGGTGAAGGAGTTC 900
```

FIG. 5(continued)

```
1-chi    CTGCAAACCTGGAAGTTCTTTGATGGCGTAGATATCGACTGGGAATTCCCGGGCGGGCAG 960
m-chi    CTGCAGACCTGGAAGTTCTTCGACGGCGTGGATATCGACTGGGAGTTCCCGGGCGGCAAA 960
mut-1    CTGCAAACCTGGAAGTTCTTTGATGGCGTAGATATCGACTGGGAATTCCCGGGCGGGCAG 960
mut-2    CTGCAGACCTGGAAGTTCTTCGACGGCGTGGATATCGACTGGGAGTTCCCGGGCGGCAAA 960
mut-3    CTGCAAACCTGGAAGTTCTTTGATGGCGTAGATATCGACTGGGAATTCCCGGGCGGGCAG 960
mut-4    CTGCAAACCTGGAAGTTCTTTGATGGCGTAGATATCGACTGGGAATTCCCGGGCGGGCAG 960
mut-5    CTGCAGACCTGGAAGTTCTTCGACGGCGTGGATATCGACTGGGAGTTCCCGGGCGGCAAA 960
mut-6    CTGCAGACCTGGAAGTTCTTCGACGGCGTGGATATCGACTGGGAGTTCCCGGGCGGCAAA 960
mut-7    CTGCAGACCTGGAAGTTCTTCGACGGCGTGGATATCGACTGGGAGTTCCCGGGCGGCCAA 960
mut-8    CTGCAGACCTGGAAGTTCTTCGACGGCGTGGATATCGACTGGGAGTTCCCGGGCGGCAAA 960
mut-9    CTGCAAACCTGGAAGTTCTTTGATGGCGTAGATATCGACTGGGAATTCCCGGGCGGGCAG 960
mut-10   CTGCAAACCTGGAAGTTCTTTGATGGCGTAGATATCGACTGGGAATTCCCGGGCGGGCAG 960

1-chi    GGTGCTAACCCGAAACTGGGCAGTACGCAGGATGGGGCAACCTATGTGCAGCTGATGAAA 1020
m-chi    GGCGCCAACCCTAACCTGGGCAGCCCGCAAGACGGGGAAACCTATGTGTTGCTGATGAAG 1020
mut-1    GGTGCTAACCCGAAACTGGGCAGTACGCAGGATGGGGCAACCTATGTGCAGCTGATGAAA 1020
mut-2    GGCGCCAACCCTAACCTGGGCAGCCCGCAAGACGGGGAAACCTATGTGTTGCTGATGAAG 1020
mut-3    GGTGCTAACCCGAAACTGGGCAGTACGCAGGATGGGGCAACCTATGTGCAGCTGATGAAA 1020
mut-4    GGTGCTAACCCGAAACTGGGCAGTACGCAGGATGGGGCAACCTATGTGCAGCTGATGAAA 1020
mut-5    GGCGCCAACCCTAACCTGGGCAGCCCGCAAGACGGGGAAACCTATGTGTTGCTGATGAAG 1020
mut-6    GGCGCCAACCCTAACCTGGGCAGCCCGCAAGACGGGGAAACCTATGTGTTGCTGATGAAG 1020
mut-7    GGCGCCAACCCTAACCTGGGCAGCCCGCAAGACGGGGAAACCTATGTGTTGCTGATGAAG 1020
mut-8    GGCGCCAACCCTAACCTGGGCAGCCCGCAAGACGGGGAAACCTATGTGTTGCTGATGAAG 1020
mut-9    GGTGCTAACCCGAAACTGGGCAGTACGCAGGATGGGGCAACCTATGTGCAGCTGATGAAA 1020
mut-10   GGTGCTAACCCGAAACTGGGCAGTATGCAGGATGGGGCAACCTATGTGCAGCTGATGAAA 1020

1-chi    GAGCTGCGCGCCATGCTGGATCAGCTTTCGGCGGAAACGGGCCGTAAGTATGAACTGACC 1080
m-chi    GAGCTGCGGGCGATGCTGGATCAGCTGTCGGCGGAAACCGGCCGCAAGTATGAGCTGACC 1080
mut-1    GAGCTGCGCGCCATGCTGGATCAGCTTTCGGCGGAAACGGGCCGTAAGTATGAACTGACC 1080
mut-2    GAGCTGCGGGCGATGCTGGATCAGCTGTCGGCGGAAACCGGCCGCAAGTATGAGCTGACC 1080
mut-3    GAGCTGCGCGCCATGCTGGATCAGCTTTCGGCGGAAACGGGCCGTAAGTATGAACTGACC 1080
mut-4    GAGCTGCGCGCCATGCTGGATCAGCTTTCGGCGGAAACGGGCCGTAAGTATGAACTGACC 1080
mut-5    GAGCTGCGGGCGATGCTGGATCAGCTGTCGGCGGAAACCGGCCGCAAGTATGAGCTGACC 1080
mut-6    GAGCTGCGGGCGATGCTGGATCAGCTGTCGGCGGAAACCGGCCGCAAGTATGAGCTGACC 1080
mut-7    GAGCTGCGGGCGATGCTGGATCAGCTGTCGGCGGAAACCGGCCGCAAGTATGAGCTGACC 1080
mut-8    GAGCTGCGGGCGATGCTGGATCAGCTGTCGGCGGAAACCGGCCGCAAGTATGAGCTGACC 1080
mut-9    GAGCTGCGCGCCATGCTGGATCAGCTTTCGGCGGAAACGGGCCGTAAGTATGAACTGACC 1080
mut-10   GAGCTGCGCGCCATGCTGGATCAGCTTTCGGCGGAAACGGGCCGTAAGTATGAACTGACC 1080
```

FIG. 5 (continued)

```
1-chi    TCTGCGATCAGCGCCGGCAAGGATAAAATCGATAAGGTGGATTACAACACCGCACAAAAC 1140
m-chi    TCCGCCATCAGCGCCGGTAAGGACAAGATCGACAAGGTGGCTTACAACGTTGCGCAGAAC 1140
mut-1    TCTGCGATCAGCGCCGGCAAGGATAAAATCGATAAGGTGGATTACAACACCGCACAAAAC 1140
mut-2    TCCGCCATCAGCGCCGGTAAGGACAAGATCGACAAGGTGGCTTACAACGTTGCGCAGAAC 1140
mut-3    TCTGCGATCAGCGCCGGCAAGGATAAAATCGATAAGGTGGATTACAACACCGCACAAAAC 1140
mut-4    TCTGCGATCAGCGCCGGCAAGGATAAAATCGATAAGGTGGATTACAACACCGCACAAAAC 1140
mut-5    TCCGCCATCAGCGCCGGTAAGGACAAGATCGACAAGGTGGCTTACAACGTTGCGCAGAAC 1140
mut-6    TCCGCCATCAGCGCCGGTAAGGATAAAATCGATAAGGTGGATTACAACACCGCACAAAAC 1140
mut-7    TCCGCGATCAGCGCCGGCAAGGATAAAATCGATAAGGTGGATTACAACACCGCACAAAAC 1140
mut-8    TCCGCCATCAGCGCCGGTAAGGACAAGATCGACAAGGTGGCTTACAACGTTGCGCAGAAC 1140
mut-9    TCTGCGATCAGCGCCGGCAAGGATAAAATCGATAAGGTGGATTACAACACCGCACAAAAC 1140
mut-10   TCTGCGATCAGCGCCGGCAAGGATAAAATCGATAAGGTGGATTACAACACCGCACAAAAC 1140

1-chi    TCGATGGATCACATTTTCCTGATGAGTTACGACTTCTATGGGGCATTCGATCTGAAAAAT 1200
m-chi    TCGATGGATCACATCTTCCTGATGAGCTACGACTTCTATGGCGCCTTCGATCTGAAGAAC 1200
mut-1    TCGATGGATCACATTTTCCTGATGAGTTACGACTTCTATGGGGCATTCGATCTGAAAAAT 1200
mut-2    TCGATGGATCACATCTTCCTGATGAGCTACGACTTCTATGGCGCCTTCGATCTGAAGAAC 1200
mut-3    TCGATGGATCACATTTTCCTGATGAGTTACGACTTCTATGGGGCATTCGATCTGAAAAAT 1200
mut-4    TCGATGGATCACATTTTCCTGATGAGTTACGACTTCTATGGGGCATTCGATCTGAAAAAT 1200
mut-5    TCGATGGATCACATCTTCCTGATGAGCTACGACTTCTATGGCGCCTTCGATCTGAAGAAC 1200
mut-6    TCGATGGATCACATTTTCCTGATGAGTTACGACTTCTATGGGGCATTCGATCTGAAAAAT 1200
mut-7    TCGATGGATCACATTTTCCTGATGAGTTACGACTTCTATGGGGCATTCGATCTGAAAAAT 1200
mut-8    TCGATGGATCACATCTTCCTGATGAGCTACGACTTCTATGGCGCCTTCGATCTGAAGAAC 1200
mut-9    TCGATGGATCACATTTTCCTGATGAGTTACGACTTCTATGGGCCTTCGATCTGAAGAAC 1200
mut-10   TCGATGGATCACATTTTCCTGATGAGTTACGACTTCTATGGGGCATTCGATCTGAAAAAT 1200

1-chi    CTGGGCCACCAGACTGCGCTGAAAGCGCCGGCCTGGAAACCGGATACGGCGTATACCACG 1260
m-chi    CTGGGGCATCAGACCGCGCTGAATGCGCCGGCCTGGAAGCCGGACACCGCTTACACCACG 1260
mut-1    CTGGGCCACCAGACTGCGCTGAAAGCGCCGGCCTGGAAACCGGATACGGCGTATACCACG 1260
mut-2    CTGGGGCATCAGACCGCGCTGAATGCGCCGGCCTGGAAGCCGGACACCGCTTACACCACG 1260
mut-3    CTGGGCCACCAGACTGCGCTGAAAGCGCCGGCCTGGAAACCGGATACGGCGTATACCACG 1260
mut-4    CTGGGCCACCAGACTGCGCTGAAAGCGCCGGCCTGGAAACCGGATACGGCGTATACCACG 1260
mut-5    CTGGGGCATCAGACCGCGCTGAAAGCGCCGGCCTGGAAACCGGATACGGCGTATACCACG 1260
mut-6    CTGGGCCACCAGACTGCGCTGAAAGCGCCGGCCTGGAAACCGGATACGGCGTATACCACG 1260
mut-7    CTGGGCCACCAGACTGCGCTGAAAGCGCCGGCCTGGAAACCGGATACGGCGTATACCACG 1260
mut-8    CTGGGGCATCAGACCGCGCTGAATGCGCCGGCCTGGAAGCCGGACACCGCTTACACCACG 1260
mut-9    CTGGGGCATCAGACCGCGCTGAATGCGCCGGCCTGGAAGCCGGACACCGCTTACACCACG 1260
mut-10   CTGGGCCACCAGACTGCGCTGAAAGCGCCGGCCTGGAAACCGGATACGGCGTATACCACG 1260
```

FIG. 5 (continued)

```
l-chi    GTGAATGGCGTTAATGCACTGCTCACGCAGGGCGTGAAGCCGGGCAAAATCGTGGTGGGC 1320
m-chi    GTGAACGGCGTCAATGCGCTGCTGGCGCAGGGCGTCAAGCCGGGCAAGATCGTGGTCGGC 1320
mut-1    GTGAATGGCGTTAATGCACTGCTCACGCAGGGCGTGAAGCCGGGCAAAATCGTGGTGGGC 1320
mut-2    GTGAACGGCGTCAATGCGCTGCTGGCGCAGGGCGTCAAGCCGGGCAAGATCGTGGTCGGC 1320
mut-3    GTGAATGGCGTTAATGCACTGCTCACGCAGGGCGTGAAGCCGGGCAAAATCGTGGTGGGC 1320
mut-4    GTGAATGGCGTTAATGCACTGCTCACGCAGGGCGTGAAGCCGGGCAAAATCGTGGTGGGC 1320
mut-5    GTGAATGGCGTTAATGCACTGCTCACGCAGGGCGTGAAGCCGGGCAAAATCGTGGTGGGC 1320
mut-6    GTGAATGGCGTTAATGCACTGCTCACGCAGGGCGTGAAGCCGGGCAAAATCGTGGTGGGC 1320
mut-7    GTGAATGGCGTTAATGCACTGCTCGCGCAGGGCGTGAAGCCGGGCAAAATCGTGGTGGGC 1320
mut-8    GTGAACGGCGTCAATGCGCTGCTGGCGCAGGGCGTCAAGCCGGGCAAGATCGTGGTCGGC 1320
mut-9    GTGAACGGCGTCAATGCGCTGCTGGCGCAGGGCGTCAAGCCGGGCAAAATCGTGGTGGGC 1320
mut-10   GTGAATGGCGTTAATGCACTGCTCACGCAGGGCGTGAAGCCGGGCAAAATCGTGGTGGGC 1320 l-chi    ACCGCCATGTACGGTCGCGGTTGGACCGGGGTGAACGGTTACCAGAACAACATTCCGTTT 1380
m-chi    ACCGCCATGTATGGCCGCGGCTGGACCGGGGTGAACGGCTACCAGAACAACATTCCGTTC 1380
mut-1    ACCGCCATGTACGGTCGCGGTTGGACCGGGGTGAACGGTTACCAGAACAACATTCCGTTT 1380
mut-2    ACCGCCATGTATGGCCGCGGCTGGACCGGGGTGAACGGCTACCAGAACAACATTCCGTTC 1380
mut-3    ACCGCCATGTACGGTCGCGGTTGGACCGGGGTGAACGGTTACCAGAACAACATTCCGTTT 1380
mut-4    ACCGCCATGTACGGTCGCGGTTGGACCGGGGTGAACGGTTACCAGAACAACATTCCGTTT 1380
mut-5    ACCGCCATGTACGGTCGCGGTTGGACCGGGGTGAACGGTTACCAGAACAACATTCCGTTT 1380
mut-6    ACCGCCATGTACGGTCGCGGTTGGACCGGGGTGAACGGTTACCAGAACAACATTCCGTTT 1380
mut-7    ACCGCCATGTACGGTCGCGGTTGGACCGGGGTGAACGGTTACCAGAACAACATTCCGTTT 1380
mut-8    ACCGCCATGTATGGCCGCGGCTGGACCGGGGTGAACGGCTACCAGAACAACATTCCGTTC 1380
mut-9    ACCGCCATGTACGGTCGCGGTTGGACCGGGGTGAACGGTTACCAGAACAACATTCCGTTT 1380
mut-10   ACCGCCATGTACGGTCGCGGTTGGACCGGGGTGAACGGTTACCAGAACAACATTCCGTTT 1380 l-chi    ACCGGCACCGCCACTGGCCCGGTGAAAGGCACCTGGGAAAATGGCATCGTGGATTACCGC 1440
m-chi    ACCGGTACCGCCACTGGGCCGGTTAAAGGCACCTGGGAGAACGGCATCGTGGACTACCGC 1440
mut-1    ACCGGCACCGCCACTGGCCCGGTGAAAGGCACCTGGGAAAATGGCATCGTGGATTACCGC 1440
mut-2    ACCGGTACCGCCACTGGGCCGGTTAAAGGCACCTGGGAGAACGGCATCGTGGACTACCGC 1440
mut-3    ACCGGCACCGCCACTGGCCCGGTGAAAGGCACCTGGGAAAATGGCATCGTGGATTACCGC 1440
mut-4    ACCGGCACCGCCACTGGCCCGGTGAAAGGCACCTGGGAAAATGGCATCGTGGATTACCGC 1440
mut-5    ACCGGCACCGCCACTGGCCCGGTGAAAGGCACCTGGGAAAATGGCATCGTGGATTACCGC 1440
mut-6    ACCGGCACCGCCACTGGCCCGGTGAAAGGCACCTGGGAAAATGGCATCGTGGATTACCGC 1440
mut-7    ACCGGCACCGCCACTGGCCCGGTGAAAGGCACCTGGGAAAATGGCATCGTGGATTACCGC 1440
mut-8    ACCGGTACCGCCACTGGGCCGGTTAAAGGCACCTGGGAGAACGGCATCGTGGACTACCGC 1440
mut-9    ACCGGCACCGCCACTGGCCCGGTGAAAGGCACCTGGGAAAATGGCATCGTGGATTACCGC 1440
mut-10   ACCGGCACCGCCACTGGCCCGGTGAAAGGCACCTGGGAAAATGGCATCGTGGATTACCGC 1440
```

FIG. 5(continued)

```
1-chi    CAGATCGCCAATGAGTTTATGAGCGGCGAATGGCAGTACAGCTACGATGCTACCGCTGAA 1500
m-chi    CAAATCGCCGGCCAGTTCATGAGCGGCGAGTGGCAGTATACCTACGACGCCACGGCGGAA 1500
mut-1    CAGATCGCCAATGAGTTTATGAGCGGCGAATGGCAGTACAGCTACGATGCTACCGCTGAA 1500
mut-2    CAGATCGCCAATGAGTTTATGAGCGGCGAATGGCAGTACAGCTACGATGCTACCGCTGAA 1500
mut-3    CAGATCGCCAATGAGTTTATGAGCGGCGAATGGCAGTACAGCTACGATGCTACCGCTGAA 1500
mut-4    CAGATCGCCAATGAGTTTATGAGCGGCGAATGGCAGTACAGCTACGATGCTACCGCTGAA 1500
mut-5    CAGATCGCCAATGAGTTTATGAGCGGCGAATGGCAGTACAGCTACGATGCTACCGCTGAA 1500
mut-6    CAGATCGCCAATGAGTTTATGAGCGGCGAATGGCAGTACAGCTACGATGCTACCGCTGAA 1500
mut-7    CAGATCGCCAATGAGTTTATGAGCGGCGAATGGCAGTACAGCTACGATGCTACCGCTGAA 1500
mut-8    CAAATCGCCGGCCAGTTCATGAGCGGCGAGTGGCAGTATACCTACGACGCCACGGCGGAA 1500
mut-9    CAGATCGCCAATGAGTTTATGAGCGGCGAATGGCAGTACAGCTACGATGCTACCGCTGAA 1500
mut-10   CAGATCGCCAATGAGTTTATGAGCGGCGAATGGCAGTACAGCTACGATGCTACCGCTGAA 1500

1-chi    GCACCCTATGTCTTCAAACCTTCCACTGGCGATCTGATCACCTTCGACGATGCGCGCTCG 1560
m-chi    GCGCCTTACGTGTTCAAACCTTCCACCGGCGATCTGATCACCTTCGACGATGCCCGCTCG 1560
mut-1    GCACCCTATGTCTTCAAACCTTCCACTGGCGATCTGATCACCTTCGACGATGCGCGCTCG 1560
mut-2    GCACCCTATGTCTTCAAACCTTCCACTGGCGATCTGATCACCTTCGACGATGCGCGCTCG 1560
mut-3    GCACCCTATGTCTTCAAACCTTCCACTGGCGATCTGATCACCTTCGACGATGCGCGCTCG 1560
mut-4    GCACCCTATGTCTTCAAACCTTCCACTGGCGATCTGATCACCTTCGACGATGCGCGCTCG 1560
mut-5    GCACCCTATGTCTTCAAACCTTCCACTGGCGATCTGATCACCTTCGACGATGCCCGCTCG 1560
mut-5    GCACCCTATGTCTTCAAACCTTCCACTGGCGATCTGATCACCTTCGACGATGCGCGCTCG 1560
mut-6    GCACCCTATGTCTTCAAACCTTCCACTGGCGATCTGATCACCTTCGACGATGCGCGCTCG 1560
mut-7    GCACCCTATGTCTTCAAACCTTCCACTGGCGATCTGATCACCTTCGACGATGCGCGCTCG 1560
mut-8    GCGCCTTACGTGTTCAAACCTTCCACCGGCGATCTGATCACCTTCGACGATGCCCGCTCG 1560
mut-9    GCACCCTATGTCTTCAAACCTTCCACTGGCGATCTGATCACCTTCGACGATGCGCGCTCG 1560
mut-10   GCACCCTATGTCTTCAAACCTTCCACTGGCGATCTGATCACCTTCGACGATGCGCGCTCG 1560

1-chi    GTGCAGGCGAAGGGCAAATATGTGCTGGATAAGCAGCTGGGCGGGTTGTTCTCATGGGAA 1620
m-chi    GTGCAGGCCAAAGGCAAGTACGTGCTGGATAAGCAGCTGGGCGGCCTGTTCTCCTGGGAG 1620
mut-1    GTGCAGGCGAAGGGCAAATATGTGCTGGATAAGCAGCTGGGCGGGTTGTTCTCATGGGAA 1620
mut-2    GTGCAGGCGAAGGGCAAATATGTGCTGGATAAGCAGCTGGGCGGGTTGTTCTCATGGGAA 1620
mut-3    GTGCAGGCGAAGGGCAAATATGTGCTGGATAAGCAGCTGGGCGGGTTGTTCTCATGGGAA 1620
mut-4    GTGCAGGCGAAGGGCAAATATGTGCTGGATAAGCAGCTGGGCGGGTTGTTCTCATGGGAA 1620
mut-5    GTGCAGGCCAAAGGCAAGTACGTGCTGGATAAGCAGCTGGGCGGCCTGTTCTCCTGGGAG 1620
mut-6    GTGCAGGCGAAGGGCAAATATGTGCTGGATAAGCAGCTGGGCGGGTTGTTCTCATGGGAA 1620
mut-7    GTGCAGGCGAAGGGCAAATATGTGCTGGATAAGCAGCTGGGCGGGTTGTTCTCATGGGAA 1620
mut-8    GTGCAGGCCAAAGGCAAGTACGTGCTGGATAAGCAGCTGGGCGGCCTGTTCTCCTGGGAG 1620
mut-9    GTGCAGGCGAAGGGCAAATATGTGCTGGATAAGCAGCTGGGCGGGTTGTTCTCATGGGAA 1620
mut-10   GTGCAGGCGAAGGGCAAATATGTGCTGGATAAGCAGCTGGGCGGGTTGTTCTCATGGGAA 1620
```

FIG. 5 (continued)

```
l-chi    ATTGACGCCGACAACGGCGATATTCTGAATAACATGAACAGCAGCCTGGGCAACAGCGTC 1680
m-chi    ATCGACGCGGATAACGGCGATATTCTCAACAGCATGAACGCCAGCCTGGGCAACAGCGCC 1680
mut-1    ATTGACGCCGACAACGGCGATATTCTGAATAACATGAACAGCAGCCTGGGCAACAGCGTC 1680
mut-2    ATTGACGCCGACAACGGCGATATTCTGAATAACATGAACAGCAGCCTGGGCAACAGCGTC 1680
mut-3    ATTGACGCCGACAACGGCGATATTCTGAATAACATGAACAGCAGCCTGGGCAACAGCGTC 1680
mut-4    ATTGACGCCGACAACGGCGATATTCTGAATAACATGAACAGCAGCCTGGGCAACAGCGTC 1680
mut-5    ATCGACGCGGATAACGGCGATATTCTCAACAGCATGAACGCCAGCCTGGGCAACAGCGCC 1680
mut-6    ATTGACGCCGACAACGGCGATATTCTGAATAACATGAACAGCAGCCTGGGCAACAGCGTC 1680
mut-7    ATTGACGCCGACAACGGCGATATTCTGAATAACATGAACAGCAGCCTGGGCAACAGCGTC 1680
mut-8    ATCGACGCGGATAACGGCGATATTCTCAACAGCATGAACGCCAGCCTGGGCAACAGCGCC 1680
mut-9    ATTGACGCCGACAACGGCGATATTCTGAATAACATGAACAGCAGCCTGGGCAACAGCGTC 1680
mut-10   ATTGACGCCGACAACGGCGATATTCTGAATAACATGAACAGCAGCCTGGGCAACAGCGTC 1680 l-chi    GGTACGCCTTAA 1692
m-chi    GGCGTTCAATAA 1692
mut-1    GGTACGCCTTAA 1692
mut-2    GGTACGCCTTAA 1692
mut-3    GGTACGCCTTAA 1692
mut-4    GGTACGCCTTAA 1692
mut-5    GGCGTTCAATAA 1692
mut-6    GGTACGCCTTAA 1692
mut-7    GGTACGCCTTAA 1692
mut-8    GGCGTTCAATAA 1692
mut-9    GGTACGCCTTAA 1692
mut-10   GGTACGCCTTAA 1692
```

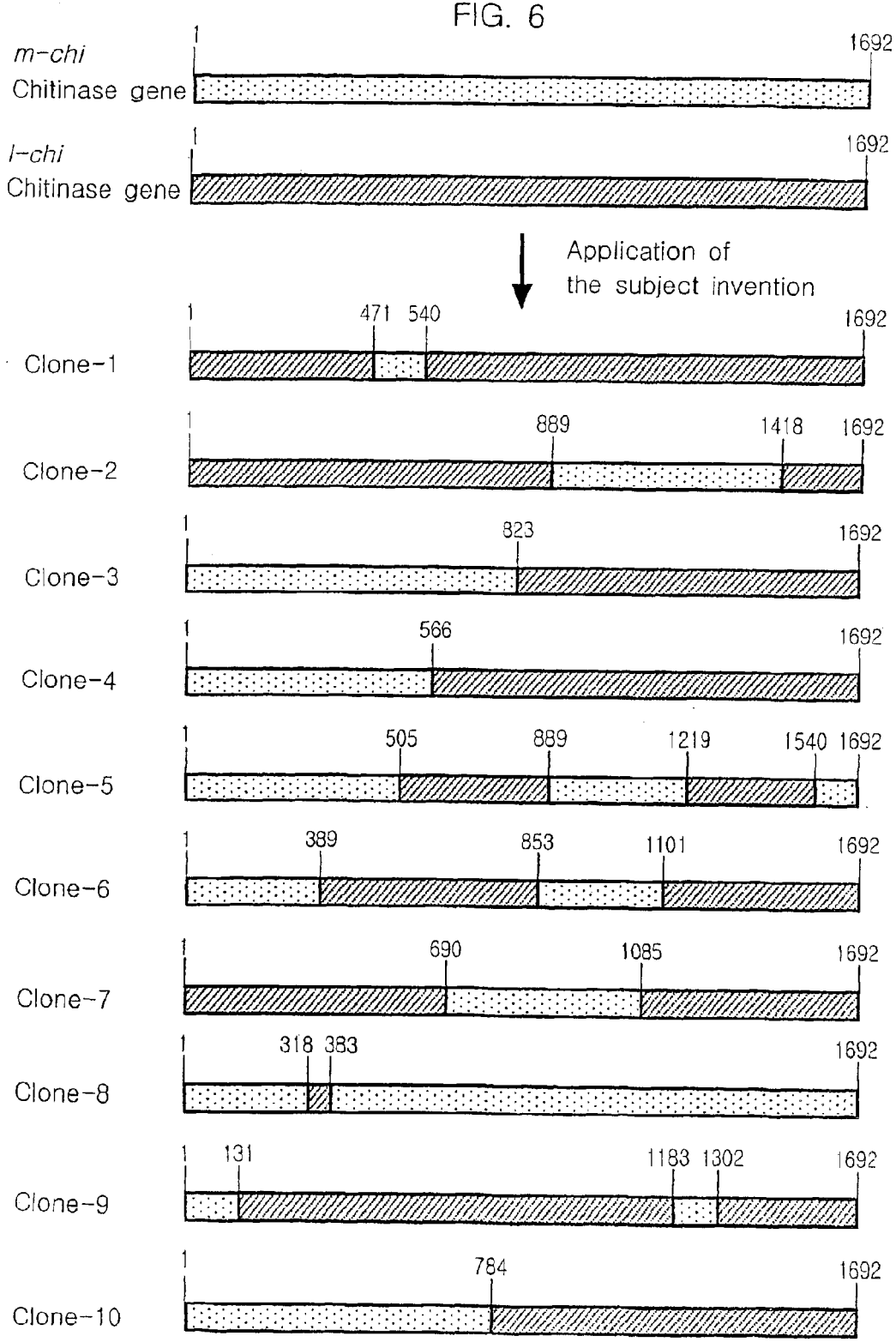

FIG. 8

```
l-chi    ATGCGCAAAT TTAATAAACC GCTGTTGGCG TTGCTGATCG GCAGCACGCT    50
m-chi    ATGCGCAAAT TTAATAAACC GCTGTTGGCG CTGTTGATCG GCAGCACGCT    50
R-24     ATGCGCAAAT TTAATAAACC GCTGTTGGCG TTGCTGATCG GCAGCACGCT    50 l-chi    GTGCTCTGCG GCGCAGGCCG CTGCACCGGG CAAACCTACG TTGGCCTGGG    100
m-chi    GTGTTCCGCG GCGCAGGCCG CCGCGCCGGG CAAGCCGACC ATCGCCTGGG    100
R-24     GTGCTCTGCG GCGCAGGCCG CTGCACCGGG CAAACCTACG TTGGCCTGGG    100 l-chi    GCAATACCAA ATTCGCCATT GTCGAAGTCG ATCAAGCGGC GACGGCTTAT    150
m-chi    GCAACACCAA GTTCGCCATC GTTGAAGTTG ACCAGGCGGC TACCGCTTAT    150
R-24     GCAATACCAA ATTCGCCATT GTCGAAGTCG ATCAAGCGGC GACGGCTTAT    150 l-chi    AATAATCTGG TGAAAGTAAA AAGTGCCGCC GACGTTTCTG TTTCATGGAA    200
m-chi    AATAATTTGG TGAAGGTAAA AAATGCCGCC GATGTTTCCG TCTCCTGGAA    200
R-24     AATAATCTGG TGAAAGTAAA AAGTGCCGCC GACGTTTCTG TTTCATGGAA    200 l-chi    TTTATGGAAT GGCGATACCG GTACCACGGC AAAAGTATTA TTAAATGGCA    250
m-chi    TTTATGGAAT GGCGACGCGG GCACGACGGC CAAGATTTTA TTAAATGGTA    250
R-24     TTTATGGAAT GGCGATACCG GTACCACGGC AAAAGTATTA TTAAATGGCA    250 l-chi    AAGAAGTTTG GAGTGGTGCC TCAACCGGTA GTTCGGGAAC CGCAAACTTT    300
m-chi    AAGAGGCGTG GAGTGGTCCT TCAACCGGAT CTTCCGGTAC GGCGAATTTT    300
R-24     AAGAAGTTTG GAGTGGTGCC TCAACCGGTA GTTCGGGAAC CGCAAACTTT    300 l-chi    AAGGTGAATA AAGGCGGCCG TTATCAAATG CAGGTGGCGT TATGCAACGC    350
m-chi    AAAGTGAATA AAGGCGGCCG TTATCAAATG CAGGTGGCAT TGTGCAATGC    350
R-24     AAGGTGAATA AAGGCGGCCG TTATCAAATG CAGGTGGCGT TATGCAACGC    350 l-chi    CGACGGCTGT ACCGCCAGCG ATGCAACCGA AATTGTGGTG GCAGATACCG    400
m-chi    CGACGGCTGC ACCGCCAGTG ACGCCACCGA AATTGTGGTG GCCGACACCG    400
R-24     CGACGGCTGT ACCGCCAGCG ATGCAACCGA AATTGTGGTG GCAGATACCG    400 l-chi    ACGGTAGCCA TTTGGCACCT TTAAAAGAAC CTTTGTTGGA AAAGAATAAG    450
m-chi    ACGGCAGCCA TTTGGCGCCG TTGAAAGAGC CGCTGCTGGA AAAGAATAAA    450
R-24     ACGGTAGCCA TTTGGCACCT TTAAAAGAAC CTTTGTTGGA AAAGAATAAG    450 l-chi    CCTTATAAAC AAGACTCCGG CAAAGTGGTT GGCTCTTATT TCGTTGAATG    500
m-chi    CCGTATAAAC AGAACTCCGG CAAAGTGGTC GGTTCTTATT TCGTCGAGTG    500
R-24     CCTTATAAAC AAGACTCCGG CAAAGTGGTC GGTTCTTATT TCGTCGAGTG    500 l-chi    GGGCGTTTAC GGCCGTAATT TCACCGTCGA TAAACTTCCG GCTCAGAACC    550
m-chi    GGGCGTTTAC GGGCGCAATT TCACCGTCGA CAAGATCCCG GCGCAAAACC    550
R-24     GGGCGTTTAC GGCCGTAATT TCACCGTCGA TAAACTTCCG GCTCAGAACC    550 l-chi    TGACGCACCT GCTGTACGGC TTTATCCCTA TCTGTGGCGG TGACGGCATC    600
m-chi    TGACCCACCT GCTGTACGGC TTTATCCCGA TCTGCGGCGG CAATGGCATC    600
R-24     TGACGCACCT GCTGTACGGC TTTATCCCTA TCTGTGGCGG TGACGGCATC    600 l-chi    AACGACAGCC TGAAAGAGAT CGAAGGCAGC TTCCAGGCGT TACAGCGTTC    650
m-chi    AACGACAGCC TGAAAGAGAT TGAAGGCAGC TTCCAGGCGT TACAGCGCTC    650
R-24     AACGACAGCC TGAAAGAGAT TGAAGGCAGC TTCCAGGCGT TACAGCGCTC    650
```

FIG. 8(continued)

```
l-chi   CTGTCAGGGG CGTGAAGACT TTAAGGTATC GATCCACGAT CCGTTCGCTG   700
m-chi   CTGCCAGGGC CGCGAGGACT TCAAAGTCTC GGTCCACGAT CCGTTCGCCG   700
R-24    CTGCCAGGGC CGCGAGGACT TCAAAGTCTC GGTCCACGAT CCGTTCGCCG   700 l-chi   CGCTGCAGAA AGGTCAGAAG GGCGTGACCG CCTGGGACGA CCCCTACAAA   750
m-chi   CGCTGCAAAA AGCGCAGAAG GGCGTGACCG CCTGGGATGA CCCCTACAAG   750
R-24    CGCTGCAAAA AGCGCAGAAG GGCGTGACCG CCTGGGATGA CCCCTACAAG   750 l-chi   GGCAACTTCG GCCAGTTGAT GGCGTTGAAA CAGGCGCGCC CGGACCTGAA   800
m-chi   GGCAACTTCG GCCAGCTGAT GGCGCTGAAG CAGGCGCATC CTGACCTGAA   800
R-24    GGCAACTTCG GCCAGCTGAT GGCGCTGAAG CAGGCGCATC CTGACCTGAA   800 l-chi   AATCCTGCCG TCGATCGGTG GCTGGACGTT ATCCGATCCG TTCTTCTTTA   850
m-chi   AATCCTGCCG TCGATCGGCG GCTGGACGCT GTCCGACCCG TTCTTCTTCA   850
R-24    AATCCTGCCG TCGATCGGCG GCTGGACGCT GTCCGACCCG TTCTTCTTCA   850 l-chi   TGGGCGATAA GGTGAAGCGC GATCGCTTCG TCGGCTCGGT GAAGGAGTTC   900
m-chi   TGGGCGACAA GGTGAAGCGC GATCGCTTCG TCGGTTCGGT GAAAGAGTTC   900
R-24    TGGGCGACAA GGTGAAGCGC GATCGCTTCG TCGGTTCGGT GAAAGAGTTC   900 l-chi   CTGCAAACCT GGAAGTTCTT TGATGGCGTA GATATCGACT GGGAATTCCC   950
m-chi   CTGCAGACCT GGAAGTTCTT CGACGGCGTG GATATCGACT GGGAGTTCCC   950
R-24    CTGCAGACCT GGAAGTTCTT CGACGGCGTG GATATCGACT GGGAGTTCCC   950 l-chi   GGGCGGGCAG GGTGCTAACC CGAAACTGGG CAGTACGCAG GATGGGGCAA   1000
m-chi   GGGCGGCAAA GGCGCCAACC CTAACCTGGG CAGCCCGCAA GACGGGGAAA   1000
R-24    GGGCGGCAAA GGCGCCAACC CTAACCTGGG CAGCCCGCAA GACGGGGAAA   1000 l-chi   CCTATGTGCA GCTGATGAAA GAGCTGCGCG CCATGCTGGA TCAGCTTTCG   1050
m-chi   CCTATGTGTT GCTGATGAAG GAGCTGCGGG CGATGCTGGA TCAGCTGTCG   1050
R-24    CCTATGTGTT GCTGATGAAG GAGCTGCGGG CGATGCTGGA TCAGCTGTCG   1050 l-chi   GCGGAAACGG GCCGTAAGTA TGAACTGACC TCTGCGATCA GCGCCGGCAA   1100
m-chi   GCGGAAACCG GCCGCAAGTA TGAGCTGACC TCCGCCATCA GCGCCGGTAA   1100
R-24    GCGGAAACCG GCCGCAAGTA TGAGCTGACC TCCGCCATCA GCGCCGGTAA   1100 l-chi   GGATAAAATC GATAAGGTGG ATTACAACAC CGCACAAAAC TCGATGGATC   1150
m-chi   GGACAAGATC GACAAGGTGG CTTACAACGT TGCGCAGAAC TCGATGGATC   1150
R-24    GGACAAGATC GACAAGGTGG CTTACAACGT TGCGCAGAAC TCGATGGATC   1150 l-chi   ACATTTTCCT GATGAGTTAC GACTTCTATG GGCATTCGA TCTGAAAAAT    1200
m-chi   ACATCTTCCT GATGAGCTAC GACTTCTATG GCGCCTTCGA TCTGAAGAAC   1200
R-24    ACATCTTCCT GATGAGCTAC GACTTCTATG GCGCCTTCGA TCTGAAGAAC   1200 l-chi   CTGGGCCACC AGACTGCGCT GAAAGCGCCG GCCTGGAAAC CGGATACGGC   1250
m-chi   CTGGGGCATC AGACCGCGCT GAATGCGCCG GCCTGGAAGC CGGACACCGC   1250
R-24    CTGGGGCATC AGACCGCGCT GAATGCGCCG GCCTGGAAGC CGGACACCGC   1250 l-chi   GTATACCACG GTGAATGGCG TTAATGCACT GCTCACGCAG GGCGTGAAGC   1300
m-chi   TTACACCACG GTGAACGGCG TCAATGCGCT GCTGGCGCAG GGCGTCAAGC   1300
R-241   TTACACCACG GTGAACGGCG TCAATGCGCT GCTGGCGCAG GGCGTGAAGC   1300
```

FIG. 8 (continued)

```
l-chi   CGGGCAAAAT CGTGGTGGGC ACCGCCATGT ACGGTCGCGG TTGGACCGGG   1350
m-chi   CGGGCAAGAT CGTGGTCGGC ACCGCCATGT ATGGCCGCGG CTGGACCGGG   1350
R-24    CGGGCAAAAT CGTGGTGGGC ACCGCCATGT ACGGTCGCGG TTGGACCGGG   1350 l-chi   GTGAACGGTT ACCAGAACAA CATTCCGTTT ACCGGCACCG CCACTGGCCC   1400
m-chi   GTGAACGGCT ACCAGAACAA CATTCCGTTc ACCGGTACCG CCACTGGGCC   1400
R-24    GTGAACGGTT ACCAGAACAA CATTCCGTTT ACCGGCACCG CCACTGGCCC   1400 l-chi   GGTGAAAGGC ACCTGGGAAA ATGGCATCGT GGATTACCGC CAGATCGCCA   1450
m-chi   GGTTAAAGGC ACCTGGGAGA ACGGCATCGT GGACTACCGC CAAATCGCCG   1450
R-24    GGTGAAAGGC ACCTGGGAAA ATGGCATCGT GGATTACCGC CAGATCGCCA   1450 l-chi   ATGAGTTTAT GAGCGGCGAA TGGCAGTACA GCTACGATGC TACCGCTGAA   1500
m-chi   GCCAGTTCAT GAGCGGCGAG TGGCAGTATA CCTACGACGC CACGGCGGAA   1500
R-24    ATGAGTTTAT GAGCGGCGAA TGGCAGTACA GCTACGATGC TACCGCTGAA   1500 l-chi   GCACCCTATG TCTTCAAACC TTCCACTGGC GATCTGATCA CCTTCGACGA   1550
m-chi   GCGCCTTACG TGTTCAAACC TTCCACCGGC GATCTGATCA CCTTCGACGA   1550
R-24    GCACCCTATG TCTTCAAACC TTCCACTGGC GATCTGATCA CCTTCGACGA   1550 l-chi   TGCGCGCTCG GTGCAGGCGA AGGGCAAATA TGTGCTGGAT AAGCAGCTGG   1600
m-chi   TGCCCGCTCG GTGCAGGCCA AAGGCAAGTA CGTGCTGGAT AAGCAGCTGG   1600
R-24    TGCGCGCTCG GTGCAGGCGA AGGGCAAATA TGTGCTGGAT AAGCAGCTGG   1600 l-chi   GCGGGTTGTT CTCATGGGAA ATTGACGCCG ACAACGGCGA TATTCTGAAT   1650
m-chi   GCGGCCTGTT CTCCTGGGAG ATCGACGCGG ATAACGGCGA TATTCTCAAC   1650
R-24    GCGGGTTGTT CTCATGGGAA ATTGACGCCG ACAACGGCGA TATTCTGAAT   1650 l-chi   AACATGAACA GCAGCCTGGG CAACAGCGTC GGTACGCCTT AA           1692
m-chi   AGCATGAACG CCAGCCTGGG CAACAGCGCC GGCGTTCAAT AA           1692
R-24    AACATGAACA GCAGCCTGGG CAACAGCGTC GGTACGCCTT AA           1692
```

FIG. 10

```
Wild  ATGAATGGAAAAAGA AAAATTTTCACATGT ATTTCTATTGTAGGA ATCGGACTAGCTAGT  60
M-13  ATGAATGGAAAAAGA AAAATTTTCACATGT ATTTCTATTGTAGGA ATCGGACTAGCTAGC  60
M-20  ATGAATGGAAAAAGA AAAATTTTCACGTGT ATTTCTATTGTAGGA ATCGGACTAGCTAGT  60

Wild  TTTTCTAATTCTAGT TTCGCAGCAAGTGTA ACGGACAATTCAGTA CAAAATTCTATTCCC  120
M-13  TTTTCTAATTCTAGT TTCGCAGCAAGTGTA ACGGACAATTCAGTA CAAAATTCTATTCCC  120
M-20  TTTTCTAATCCTAGT TTCGCAGCAAGTGTA ACGGACAATTCAGTA CAAAATTCTATTCCC  120

Wild  GTAGTTAATCAACAA GTAGCTGCTGCAAAG GAAATGAAACCATTT CCGCAGCAAGTTAAT  180
M-13  GTAGTTAATCAACAA GTAGCTGCTGCAAAG GAAATGAAACCATTT CCGCAGCAAGTTTAT  180
M-20  GTAGTTAATCAACAA GTAGCTGCTGCAAAG GAAATGAAACCATTT CCGCAGCAAGTTAAT  180

Wild  TATGCAGGTGTTATA AAACCGAATCATGTT ACACAGGAAAGTTTA AATGCTTCTGTAAGA  240
M-13  TATGCAGGTGTTATA AAACCGAATCATGTT ACACAGGAAAGTTTA AATGCTTCTGTAAGA  240
M-20  TATGCAGGTGTTATA AAACCGAATCATGTT ACACAGGAAAGTTTA AATGCTTCTGTAAGA  240

Wild  AGTTACTACGATAAT TGGAAAAAGAAATAT TTGAAAAATGATTTA TCTTCTTTACCTGGT  300
M-13  AGTTACTACGATAAT TGGAAAAAGAAATAT TTGAAAAATGATTTA TCTTCTTTACCTGGT  300
M-20  AGTTACTACGATAAT TGGAAAAAGAAATAT TTGAAAAATGATTTA TCTTCTTTACCTGGT  300

Wild  GGTTATTATGTAAAA GGAGAGATTACAGGT GATGCTGATGGGTTT AAGCCACTTGGAACT  360
M-13  GGTTATTATGTAAAA GGAGATATTACAGGT GATGCTGATGGGTTT AAGCCACTTGGAACT  360
M-20  GGTTATTATGTAAAA GGAGATATTACAGGT GATGCTGATGGGTTT AAGCCACTTGGAACT  360

Wild  TCAGAAGGTCAAGGG TATGGGATGATAATT ACAGTATTAATGGCT GGTTATGATTCGAAT  420
M-13  TCAGAAGGTCAAGGG TATGGGATGATAATT ACAGTATTAATGGCT GGTTATGATTCGAAT  420
M-20  TCAGAAGGTCAAGGG TATGGGATGATAATT ACAGTATTAATGGCT GGTTATGATTCGAAT  420

Wild  GCTCAAAAAATCTAT GACGGTTTATTTAAA ACAGCAAGAACTTTT AAAAGTTCTCAAAAT  480
M-13  GCTCAAAAGATCTAT GACGGTTTATTTAAA ACAGCAAGAACTTTT AAAAGTTCTCGAAAT  480
M-20  GCTCAAAAGATCTAT GACGGTTTATTTAAA ACAGCAAGAACTTTT AAAAGTTCTCGAAAT  480

Wild  CCTAATTTAATGGGA TGGGTTGTCGCAGAT AGTAAAAAAGCACAA GGTCATTTTGATTCT  540
M-13  CCTAATTTAATGGGA TGGGTTGTCGCAGAT AGTAAAAAAGCACAA GGTCATTTTGATTCT  540
M-20  CCTAATTTAATGGGA TGGGTTGTCGCAGAT AGTAAAAAAGCACAA GGTCATTTTGATTCT  540

Wild  GCTACTGATGGAGAT TTAGATATTGCGTAT TCTCTTCTTCTTGCT CATAAGCAGTGGGGA  600
M-13  GCTACTGATGGAGAT TTAGATATTGCGTAT TCTCTTCTTCTTGCT CATAAGCAGTGGGGA  600
M-20  GCTACTGATGGAGAT TTAGATATTGCGTAT TCTCTTCTTCTTGCT CATAAGCAGTGGGGA  600

Wild  TCTAATGGAACAGTG AATTATTTGAAAGAA GCACAAGACATGATT ACAAAAGGTATTAAA  660
M-13  TCTAATGGAACAGTG AATTATTTGAAAGAA GCACAAGACATGATT ACAAAAGGTATTAAA  660
M-20  TCTAATGGAACAGTG AATTATTTGAAAGAA GCACAAGACATGATT ACAAAAGGTATTAAA  660

Wild  GCTAGTAATGTTACA AATAATAACCGACTA AATTTAGGCGATTGG GATTCTAAAAGTTCA  720
M-13  GCTAGTAATGTTACC AATAATACCCGACTA AATTTAGGCGATTGG GATTCTAAAAGTTCA  720
M-20  GCTAGTAATGTTACA AATAATAACCGACTA AATTTAGGCGATTGG GATTCTAAAAGTTCA  720
```

FIG. 10 (continued)

```
Wild  CTTGATACGAGACCA TCTGATTGGATGATG TCACACCTTAGAGCA TTTTATGAATTTACA  780
M-13  CTTGATACGAGACCA TCTGATTGGATGATG TCACACCTTAGAGCA TTTTATGAATTTACA  780
M-20  CTTGATACGAGACCA TCTGATTGGATGATG TCACACCTTAGAGCA TTTTATGAGTTTACA  780

Wild  GGTGATAAAACTTGG CTTACTGTTATTAAT AATTTGTACGATGTT TATACGCAATTTAGT  840
M-13  GGTGATAAAACTTGG CTTACTGTTATTAAT AATTTGTACGATGTT TATACGCAGTTTAGT  840
M-20  GGTGATAAAACTTGG CTTACTGTTATTAAT AATTTGTACGATGTT TATACGCAATTTAGT  840

Wild  AATAAGTACTCTCCA AATACAGGACTTATT TCAGATTTCGTTGTA AAAAACCCACCACAA  900
M-13  AATAAGTACTCTCCA AATACAGGACTTATT TCAGATTTCGTTGTA AAAAACCCACCACAA  900
M-20  AATAAGTACTCTCCA GATACAGGACTTATT TCAGATTTCGTTGTA AAAAACCCACCACAA  900

Wild  CCCGCACCTAAAGAC TTCTTAGACGAGTCA GAATATACAAATGCA TATTATTACAATGCT  960
M-13  CCCGCACCTAAAGGC TTCTTAGGGGAGTCA GAATATACAAATGCA TATTATTACAATGCT  960
M-20  CCCGCACCTAAAGGC TTCTTAGGGGAGTCA GAATATACAAATGCA TATTATTACAATGCT  960

Wild  AGTCGGGTACCATTG AGAATTGTAATGGAC TATGCGATGTACGGC GAGAAAAGAAGTAAA  1020
M-13  AGTCGGGTACCATTG AGAATTGTAATGGAC TATGCGATGTACGGC GAGAAAAGAAGTAAA  1020
M-20  AGTCGGGTACCATTG AGAATTGTAATGGAC TATGCGATGTACGGC GAGAAAAGAAGTAAA  1020

Wild  GTCATTTCTGATAAA GTTTCTTCGTGGATT CAAAATAAAACGAAT GGAAATCCTTCTAAA  1080
M-13  GTCATTTCTGATAAG GTTTCTTCGTGGATT CAAAATAAAACGAAT GGAAATCCTTCTAAA  1080
M-20  GTCATTTCTGATAAG GTTTCTTCGTGGATT CAAAATAAAACGAAT GGAGATCCTTCTAAA  1080

Wild  ATTGTGGATGGTTAT CAATTAAATGGATCT AATATTGGTAGTTAT TCAACTGCTGTATTT  1140
M-13  ATTGTGGATGGTTAT CAATTAGATGGATCT AATATTGGTAGTTAT CCAACTGCTGTATTT  1140
M-20  ATTGTGGATGGTTAT CAATTAGATGGATCT GATATTGGTAGTTAT TCAACTGCTGTATTT  1140

Wild  GTTTCACCGTTTATT GCTGCAAGTATAACA AGTAGCAATAATCAA AAGTGGGTAAATAGC  1200
M-13  GTTTCACCGCTTATT GCTGCAAGTACAACA AGTAGCAATAATCAA AAGTGGGTAAATAGC  1200
M-20  GTTTCACCGTTTATT GCTGCAAGTATAACA AGTAGCAATAATCAA AAGTGGGTAAATAGC  1200

Wild  GGTTGGGATTGGATG AAGAATAAGAGAGAA AGTTATTTTAGTGAT AGTTATAATTTATTA  1260
M-13  GGTTGGGATTGGATG AAGAATAAGAGAGAA AGTTATTTTAGTGAT AGTTATAATTTATTA  1260
M-20  GGTTGGGATTGGATG AAGAATAAGAGAGAA AGTTATTTTAGCGAT AGTTATAATTTGTTA  1260

Wild  ACTATGTTATTCATT ACAGGAAATTGGTGG AAACCTGTACCTGAT GATACAAAAATACAA  1320
M-13  ACTATGTTATTCATT ACAGGGAATTGGTGG AAACCCGTACCTGGT GATACAAAAATACAA  1320
M-20  ACTATGTTATTCATT ACGGGAAATTGGTGG AAACCTGTACCTGAT GATACAAAAATACAA  1320

Wild  AATCAAATAAATGAT GCAATTTATGAAGGA TACGATAATTAA  1362
M-13  AATCAAATAAATGAT GCTATTTATGAAGGA TACGATAATTAA  1362
M-20  AATCAAATAAATGAT GCAATTTATGAAGGA TACGATAATTAA  1362
```

FIG. 11
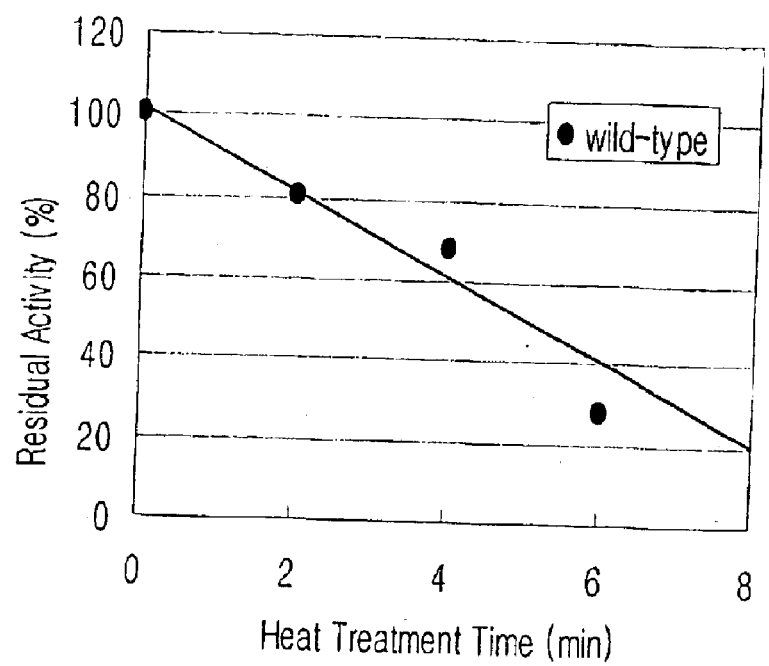
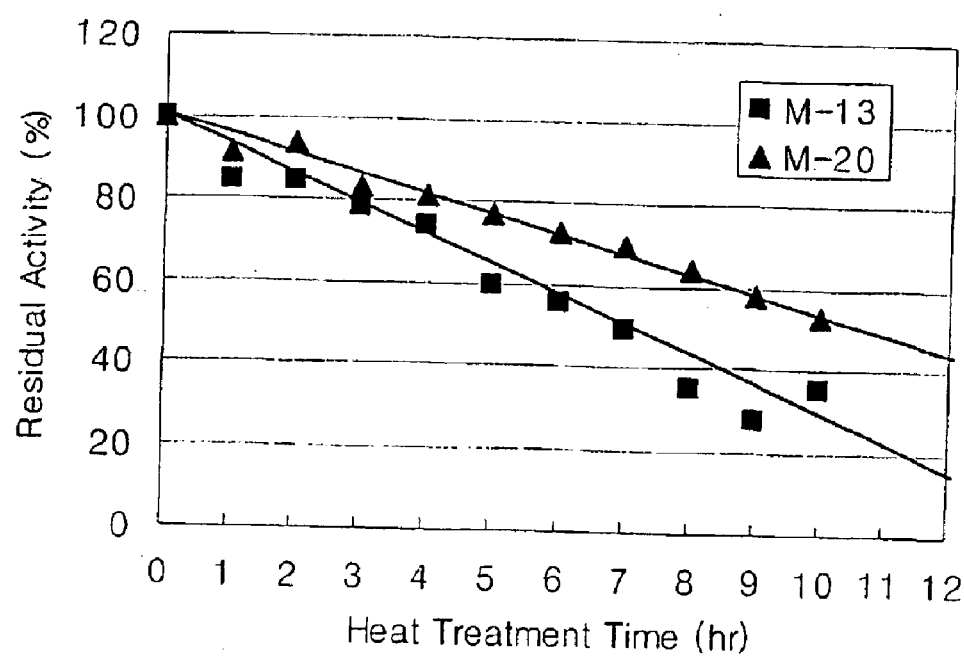

METHOD FOR GENERATING RECOMBINANT DNA LIBRARY USING UNIDIRECTIONAL SINGLE-STRANDED DNA FRAGMENTS

FIELD OF THE INVENTION

The present invention relates to a method for the production of a pool of recombinant DNA encoding mutant proteins and a recombinant DNA library comprising same, which allows the directed evolution of proteins by in vitro recombination.

BACKGROUND OF THE INVENTION

Genetic information is eventually decoded into a protein which performs most of the vital functions in living organisms. As one of important biological macromolecules, protein not only serves as a component of cells but also participates in all the biochemical reactions with a high specificity.

The function of protein comprised of 20 kinds of amino acids is determined by the structure which is divided into four levels; primary, secondary, tertiary and quaternary structures. Since the primary structure of protein, i.e., amino acid sequence, especially contains the information regarding the shape and the function thereof, the whole structure or function of the protein can be changed even by a mutation in one amino acid residue (Shao, Z. and Arnold F. H., *Curr. Opin. Struct. Biol.* 6:513–518, 1996).

The diversity of organism reflects the diversity of genetic information encoded in DNA or RNA. In nature, the genetic information is changed slowly and continuously by a natural evolution process comprising mutation, sexual reproduction and natural selection. For example, during meiosis in sexual reproduction, homologous chromosomes derived from two individuals might exchange or reassemble their genetic materials through homologous recombination. Such reassembly of the DNA provides more chances for living organisms to expedite an evolution. However, it takes long time for this type of evolution to occur in natural environment, partly due to its strong dependency on fortuity. Therefore, there have been many efforts to obtain, in a short period of time, a gene evolved for the desired purpose and a mutant protein by in vitro mutagenesis in combination with an appropriate screening method (Eigen, M., *Naturwissenschaften* 58:465–523, 1971; Bradt, R. M., *Nature* 317:804–806, 1985; Pal, K. F., *Bio. Cybern.* 69:539–546, 1993).

Current method in widespread use for creating mutant proteins is site-directed mutagenesis (Sambrook, J. et al., *Molecular Cloning* 2nd, Cold Spring Harbor Lab Press, 1989). This method replaces nucleotides of desired site with a synthetically mutagenized oligonucleotide. However, there are limitations of the method in that it requires exact information on the amino acid sequence and the function of the site to be mutagenized in-proteins. As another method for creating mutant proteins in a recombinant DNA library format, error-prone polymerase chain reaction (error-prone PCR) is used widely (Leung, D. W. et al., *Technique* 1:11–15, 1989; Caldwell, R. C. et al., *PCR Methods and Applications* 2:28–33, 1992). Error-prone PCR can be used for constructing a mutant DNA library of a gene by controlling the polymerization conditions to decrease the fidelity of polymerase. However, the error-prone PCR suffers from a low processability of the polymerase, which limits the practical applications of the method for average-sized gene.

Another limitation of error-prone PCR is that the frequency of co-occurrence of a plurality of mutations within a short-length region of DNA is too low for multiple mutations to be introduced.

To overcome said shortcomings of these methods, various methods for constructing a mutant DNA library from the mixture of homologous polynucleotides have been developed. Those are DNA shuffling method of Maxygen (U.S. Pat. Nos. 5,605,793; 6,117,679; 6,132,970), Gene Reassembly method of Diversa (U.S. Pat. No. 5,965,408) and recombination method developed by Frances H. Arnold (U.S. Pat. No. 6,153,410).

The DNA shuffling method of Maxygen, Inc. (U.S. Pat. Nos. 5,605,793; 6,117,679 and 6,132,970; Stemmer, W. P. C., *Nature*, 370: 389–391, 1994; Stemmer, W. P. C., *Proc. Natl. Acad. Sci. USA*, 91: 10747–10751, 1994) comprises the steps of fragmenting at least one kind of double-stranded DNAs to be shuffled and conducting polymerase chain reactions (PCR) with the combined fragments, wherein the homologous fragments from different parent DNAs are annealed with each other to form partially overlapping DNA segments and DNA synthesis occurs by employing the respective DNA fragments as a template concurrently as a primer for each other to produce a random recombinant DNA library. However, this method requires a relatively large amount of DNA for preparing DNA fragments and DNase I used in the fragmentation process has to be removed from the resulting DNA fragments in an enough purity not to disturb subsequent polymerization process. Further, the application of the method is limited by the property of the DNase I. For example, DNase I widely used for the purpose is liable to cleave a 3'-phosphodiester bond having a pyrimidine base rather than a purine base at its terminus, which is a serious obstacle to get a completely randomized pool of DNA fragments (Shao, Z. et al, *Nucleic Acids Res.* 26:681–683, 1998).

Gene Reassembly method of Diversa Corporation (U.S. Pat. No. 5,965,408) comprises the steps of synthesizing DNA fragments by polymerization process employing at least one kind of double-stranded DNAs to be shuffled as templates and conducting polymerase chain reactions (PCR) with the combined fragments to produce a random recombinant DNA library. It employs partially synthesized fragments produced by UV treatment or adduct formation on the template DNA, thus preventing a complete polymerization on the template DNA. Despite of the randomness of the constructed DNA library, there are still problems for the method of Diversa Corporation in view of mutagenic potential of used reagents and tediousness to optimize the reaction conditions for the treatment of polymerization terminating reagent to obtain the desired size of fragments. In addition, when pyrimidine bases exist contiguously on the DNA strand, UV treatment induces pyrimidine dimers such as a thymidine dimer, which makes the template DNA distorted and prevent the progress of polymerase along with the strand. As a result, polymerizations are likely to end up at the site of pyrimidine dimer, thus DNA fragments obtained having insufficient randomness.

DNA shuffling and Gene Reassembly methods are characterized in that the formation of partially overlapping DNA segments is a prerequisite step and each DNA fragment derived from starting DNAs to be shuffled serves as not only a template but a primer.

Another method proposed by Arnold, staggered extension process (StEP)(U.S. Pat. No. 6,153,410; Zhao, H. et al., *Nat. Biotechnol.* 16:258–261, 1998; Encell, L. P. et al., *Nature*

Biotech. 16:234–235, 1998) involves priming template double-stranded polynucleotides with random or specific primers, conducting PCR while controlling the reaction conditions to produce, in each cycle of reactions, short DNA fragments of staggered extension from the templates, and conducting repeated PCR to accomplish the recombination between genes by template switching. In case of polymerase reaction, there exist specific sequence-specific pause sites in each of target DNAs. In this line, StEP method has a problem in that the recombinant DNA library is biased from randomness since the extension rate of DNA fragments extended from the primers differs from each other even if the primers are annealed to the same region of different template DNAs (Encell, L. P. and Loeb, L. A., *Nature Biotech.*, 16: 234–235 (1998)). In StEP method, PCR conditions have to be strictly controlled in order to get short DNA fragments from staggered extension of primers by shortening the polymerization time and lowering the reaction temperature. Failure to maintain the desirable range of temperature (e.g., too low temperature) during PCR process in StEP method may lead to non-specific annealing and further formation of undesirable recombinants.

A method for constructing a recombinant DNA library whereby said drawbacks of the conventional methods are overcome would be powerful for the production of mutant proteins having improved properties. The present invention described herein is directed to a method of in vitro recombination of heterologous DNA strands, which comprises preparing unidirectional single-stranded DNA fragments, mixing the DNA fragments with specific primers, followed by polymerization and further repeating the above steps to produce a recombinant DNA library. Further advantages of the present invention will become apparent from the following description of the invention with reference to the attached drawings.

SUMMARY OF THE INVENTION

Accordingly, it is an object of the present invention to provide a method for producing various recombinant polynucleotides through the random recombination between two or more homologous double-stranded polynucleotides.

Another object of the present invention is to provide a method for constructing a recombinant DNA library, which comprises the steps of inserting said recombinant polynucleotides into a vector and transforming an expression cell with the resulting vector to obtain a plurality of mutant clones.

A further object of the present invention is to provide a method for identifying an improved mutant gene by screening recombinant polynucleotides having a desired functional properties from said recombinant DNA library.

In accordance with one aspect of the present invention, there is provided a method for constructing a recombinant DNA library comprising the steps of:

(a) generating a pool of unidirectional single-stranded polynucleotide fragments randomized in length from two or more starting polynucleotides to be reassembled which have regions of similarity with each other;

(b) conducting a polymerization process comprising multi-cyclic extension reactions wherein the unidirectional single-stranded polynucleotide fragments prepared by step (a) serve only as templates and specific oligonucleotides are added to the reaction mixture as primers, the primers being extended sequentially with directionality by means of template switching to produce at least one recombinant polynucleotide, and the resulting recombinant polynucleotide being different from the starting polynucleotides in nucleotide sequence; and (c) conducting a polymerase chain reaction using at least one specific primer to amplify the recombinant polynucleotides prepared by step (b).

In accordance with another aspect of the present invention, there is provided a method for constructing a recombinant DNA library, comprising the steps of inserting the recombinant polynucleotide prepared by the above method into a vector; and transforming an expression cell with said vector containing the recombinant polynucleotide to obtain a plurality of mutant clones.

In accordance with a further aspect of the present invention, there is provided a method for evolving a polynucleotide toward a desired property which comprises screening recombinant polynucleotides having a desired functional properties from the recombinant DNA library constructed by the above method.

BRIEF DESCRIPTION OF THE DRAWINGS

The above and other objects and features of the present invention will become apparent from the following description of the invention, when taken in conjunction with the accompanying drawings, in which:

FIG. 2 compares the nucleotide sequences of the chitinase genes of *Serratia liquefaciens* (l-chi)(SEQ ID NO: 1) and *Serratia marcescens* (m-chi) (SEQ ID NO: 2). The corresponding bases of the two genes different from each other are marked by small letters.

FIG. 5 compares the nucleotide sequences of the 10 recombinant DNAs. (SEQ ID NOs: 3 to 12), which are randomly selected from the recombinant DNA library produced by the method of the present invention, with those of two wild-type genes, i.e., l-chi gene (SEQ ID NO: 1) and m-chi gene (SEQ ID NO: 2).

FIG. 6 is a schematic diagram showing the constitutions of the mutant recombinant DNAs of FIG. 5 in comparison with the two wild-type genes.

FIG. 8 compares the nucleotide sequence of R-24 chininase gene (SEQ ID NOs: 13) with those of two wild-type genes, i.e., l-chi gene (SEQ ID NO: 1) and m-chi gene (SEQ ID NO: 2).

FIG. 10 compares the nucleotide sequences of M-13 mutant (SEQ ID NO: 15) and M-20 mutant (SEQ ID NO: 16) with that of wild-type chitosanase gene (SEQ ID NO: 14).

FIG. 11 depicts the differences in heat-stabilities of wild-type chitosanase derived from Bacillus sp. KCTC 0377BP, mutant M-13 and mutant M-20.

DETAILED DESCRIPTION OF THE INVENTION

Figure 1:
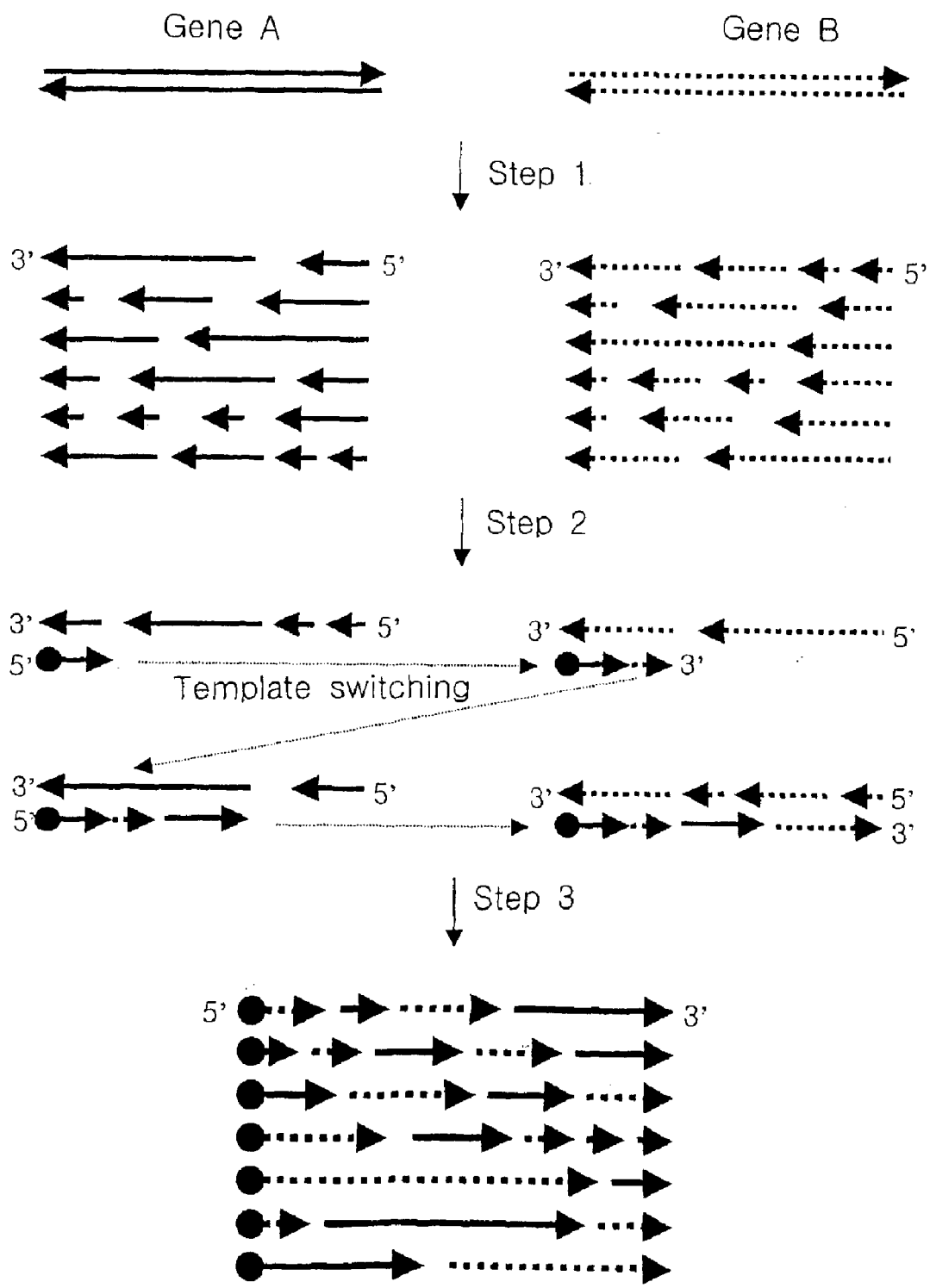
FIG. 1 shows the schematic diagram illustrating the inventive method for constructing a recombinant DNA library employing unidirectional single-stranded polynucleotide fragments as templates for the polymerase chain reaction.

The present inventors have endeavored to develop a new method for solving the problems of the prior art, and have accomplished the present invention by establishing a new method for producing a recombinant DNA library wherein a pool of various recombinant DNAs can be obtained more easily owing to the increased randomness introduced by a new principle different from those of the prior art.

The above-described DNA shuffling method of Maxygen, Inc. (U.S. Pat. Nos. 5,605,793; 6,117,679; and 6,132,970) and Gene Reassembly method of Diversa Corporation (U.S. Pat. No. 5,965,408) are commonly characterized in that the double-stranded DNA fragments obtained from more than two polynucleotides to be reassembled are converted to single stands and then annealed with each other to form partially overlapping DNA segments, and, accordingly, they are used as primers as well as templates for nucleotide extension in the polymerase chain reaction (U.S. Pat. Nos. 4,683,202 and 4,683,195) and elongated by repeating identical multi-cyclic polymerization reactions. In contrast, the method of the present invention is basically different from the prior art in that the unidirectional single-stranded polynucleotide fragments derived from two or more polynucleotides to be reassembled are used and, accordingly, no partially overlapping DNA segments are formed within the pool of single-stranded polynucleotide fragments and the unidirectional polynucleotide fragments serve only as templates; that just the oligonucleotides added as primers are elongated gradually with a directionality using the unidirectional single-stranded polynucleotide fragments as templates; and that recombination is introduced by template switching during this PCR process. Further, unlike the Arnold's StEP method (U.S. Pat. No. 6,153,410) which employs the stringent conditions controlling temperature and reaction time to produce partially elongated DNA fragment from the double-stranded target DNA used as a template, the method of the present invention uses DNA fragments as templates and, therefore, DNA fragments elongated as long as the template DNA fragments can be obtained by employing a conventional condition of polymerization reaction. Further, it is possible to increase the randomness of recombination significantly since the inventive method is not influenced by the delayed elongation rate of polymerase at the sequence-specific pause sites.

The method of the present invention for producing mutant recombinant polynucleotides provides a method for producing a group of various recombinant genes by exchanging parts of two or more homologous genes with each other, and comprises the steps of:

(a) generating a pool of unidirectional single-stranded polynucleotide fragments randomized in length from two or more starting polynucleotides to be reassembled which have regions of similarity with each other;

(b) conducting a polymerization process comprising multi-cyclic extension reactions wherein the unidirectional single-stranded polynucleotide fragments prepared by step (a) serve only as templates and specific oligonucleotides are added to the reaction mixture as primers, the primers being extended sequentially with directionality by means of template switching to produce at least one recombinant polynucleotide, and the resulting recombinant polynucleotide being different from the starting polynucleotides in nucleotide sequence; and (c) conducting a polymerase chain reaction using at least one specific primer to amplify the recombinant polynucleotides prepared by step (b).

In the polymerization reaction of step (b), when the partially elongated DNA fragments from specific primers are annealed with the template DNA fragments originated from the other starting double-stranded polynucleotide in the next cycle and the polymerization reaction is progressed, then recombinant polynucleotides containing the sequences originating from the two homologous polynucleotides in a polynucleotide are resulted therefrom. By repeating such PCR cycles, it is possible to obtain various mutant recombinant polynucleotides having randomly reassembled sequences between A and B gene as shown in FIG. 1.

In addition, the present invention provides a method for constructing a recombinant DNA library, comprising the steps of inserting the recombinant polynucleotide prepared as above into a vector; and transforming an expression cell with said vector containing the recombinant polynucleotide to obtain a plurality of mutant clones.

It is possible to screen a useful gene from the recombinant DNA library constructed by the inventive method.

Accordingly, the present invention further provides a method for identifying an improved mutant gene, which comprises screening recombinant polynucleotides having a desired functional property from the recombinant DNA library constructed by the above method.

The present invention relates to a method for producing a recombinant DNA library by random recombination between two or more genetic materials. According to the present invention, it is possible to synthesize various kinds of recombinant genes by in vitro random recombination and to prepare a novel polypeptide having a desired property by screening a clone having a desired gene from a recombinant DNA library constructed by using the recombinant genes together with a suitable expression vector and a host cell and expressing the polypeptide therefrom.

As used herein, the term "unidirectional single-stranded DNA or polynucleotide fragments" means that the single-stranded DNA or polynucleotide fragments are not anti-parallel, but parallel to each other and, accordingly, they cannot anneal with each other via complementary hydrogen bonds even if they are mixed together. For instance, when the entire nucleotide sequence of a double-stranded DNA is as follows,

5'-AGGTCCAGTTAGCATTCGGAAAGGCCGTTTGA GAGAG-3' (SEQ ID NO: 17)

3'-TCCAGGTCAATCGTAAGCCTTTCCGGCAAAC TCTCTC-5' (SEQ ID NO: 18)

the single-stranded DNAs derived therefrom such as 3'-TCCAGGTCAATCGTAAG-5' (SEQ ID NO: 19), 3'-AAACTCTCTC-5' (SEQ ID NO: 20), 3'-TTTCCGGCAAACTCTCTC-5' (SEQ ID NO: 21), 3'-CCTTTCCGGCAAACTCTCTC-5' (SEQ ID NO: 22) and 3'-TCAATCG TAAGCCTTTCCGGCAAACTCTCTC-5' (SEQ ID NO: 23) are considered to be unidirectional. Such unidirectional single-stranded DNA or polynucleotide fragments, which are employed in the method of the present invention only as templates for polymerase chain reactions, may be prepared to have various lengths depending on the sizes of the polynucleotides to be reassembled.

The term "recombinant DNA" as used herein means a chimeric DNA of a nucleotide sequence mosaic including nucleotide sequences originating from two-or more-polynucleotides, which are substantially homologous but not identical, in a molecule. The chimeric DNA contains a region of original nucleotide sequence and another region of mutated nucleotide sequence. FIGS. 5 and 6 illustrates such recombinant DNAs synthesized by the random in vitro DNA recombination by the method of the present invention. Unlike the recombinant DNA naturally produced by the gene exchange due to the crossing over between homologous chromosomes in the meiosis during sexual reproduction, the recombinant DNAs of the inventive method is produced to have various nucleotide sequences in a short time by the in vitro random recombination between homologous DNA strands and they can be inserted into a vector and expressed in a host cell transformed by the vector. A recombinant DNA library consisting of clones containing various recombinant DNAs can be constructed and a recombinant DNA having a desired property can be screened therefrom. As discussed above, the combination of in vitro production of random recombinant DNA library between two or more homologous polynucleotides with a screening technique mimicking the natural selection has an advantage in that an improved gene or mutant protein having a desired property can be obtained in a short time.

As used herein, the term "homologous" means that one single-stranded nucleic acid sequence may hybridize to a complementary single-stranded nucleic acid sequence. The degree of hybridization may depend on a number of factors including the amount of identity between the nucleic acid sequences and the hybridization conditions such as temperature and salt concentration.

As used herein, the term "mutation" means changes in the sequence of a wild-type nucleic acid sequence or changes in the sequence of a peptide expressed therefrom.

As used herein, the term "DNA library" means a set of polynucleotides or recombinant DNA fragments each consisting of two or more polynucleotides and produced by random recombination. The DNA library includes: a set of polynucleotides having various nucleotide sequence; a sum of DNAs having various nucleotide sequences or cloned DNAs; or, in a broad sense, a set of clones containing said DNAs. A recombinant DNA encoding a protein having a desired property can be screened from such DNA library and used for protein expression.

More specifically, the present invention provides a method for producing recombinant polynucleotides having randomly and artificially mutated various nucleotide sequences from naturally existing or artificially prepared two or more homologous polynucleotides by the following steps. FIG. 1 illustrates this in vitro DNA recombination method.

Step 1: A set of unidirectional single-stranded polynucleotide fragments of random lengths are generated from two or more starting polynucleotides to be reassembled, wherein the starting polynucleotides have regions of similarity with each other (Step 1 of FIG. 1).

The starting polynucleotides for use in the present invention may have a homology of more than 50% with each other, and it is preferred to employ starting polynucleotides having homologies of more than 80%.

All of the single-stranded polynucleotide fragments produced from two or more homologous polynucleotides have identical unidirectional properties. Therefore, they are parallel to each other and, accordingly, a complementary annealing between them through complementary hydrogen bonds cannot occur even if they are mixed together.

The unidirectional single-stranded polynucleotide fragments can be prepared by any one of conventional methods, e.g., a method producing unidirectional single-stranded polynucleotide fragments from RNA by reverse-transcription, a method for producing single-stranded polynucleotide fragments by gradual unidirectional deletion of nucleotides, a method for producing single-stranded polynucleotide fragments from complementary single-stranded polynucleotides. The single-stranded polynucleotide fragments can be prepared from RNA or single-stranded DNA beginning with random primers(Feinberg, A. P. and Vogelstein, B., *Anal. Biochem.*, 132: 6–13 (1983)) by employing reverse transcriptase (Gerard, G. F. et al., *Mol. Biotechnol.*, 8: 61–77 (1997)), bacteriophage T4 DNA polymerase(Nossal, N. G., *J. Biol. Chem.*, 249: 5668–5676 (1974)), bacteriophage T7 DNA polymerase(Tabor, S. and Richardson, C. C., *J. Biol. Chem.*, 264: 6447–6458 (1989)), Klenow enzyme(Klenow, H. and Henningsen, I., *Proc. Natl. Acad. Sci. USA*, 65: 168 (1970)), etc. At this time, the size of single-stranded polynucleotide can be regulated by controlling the concentration of random primers or adding an appropriate concentration of dideoxynucleotides (2',3'-dideoxyadenosine 5'-triphosphate, 2',3'-dideoxyguanosine 5'-triphosphate, 2',3'-dideoxycytidine 5'-triphosphate, 2',3'-dideoxythymidine 5'-triphosphate) to the reaction mixture to obtain single-stranded polynucleotide fragments of which length is gradually elongated from the random primers. The single-stranded polynucleotide fragments having gradual unidirectional deletions of nucleotides may be obtained by employing exonucleases capable of successively digesting the nucleotides from the 5' end of a single-stranded polynucleotide.

More specifically, the unidirectional single-stranded polynucleotide fragments can be prepared by any one of the following processes:

A process comprising the steps of (i) conducting a transcription process to produce RNA from at least one starting polynucleotide; and (ii) conducting a reverse transcription process, wherein random primers are used as primers and the RNA transcript of step (i) as a template;

A process comprising the steps of (i) generating a 3'-overhang on one side of the starting double-stranded polynucleotides by digesting with at least one restriction enzyme; (ii) producing a pool of double-stranded polynucleotides having unidirectional sequential deletion by treating the reaction mixture of step (i) with exonuclease III followed by removing aliquots of-the reaction mixture at a chosen time interval and further blocking the activity of the exonuclease III; (iii) treating the resulting double-stranded polynucleotides having a 5'-overhang with an S1 nuclease and a DNA polymerase to form a blunt end thereof; (iv) generating a new 3'-overhang to the same side which has 3'-overhang in step (i); and (v) treating the polynucleotides of step (iv) with exonuclease III to generate single-stranded polynucleotides;

A process comprising the steps of (i) generating a 3'-overhang on one side of the starting double-stranded polynucleotides by digesting with at least one restriction enzyme; (ii) treating the polynucleotides of step (i) with exonuclease III to generate single-stranded polynucleotides; and (iii) conducting a polymerization process on the single-stranded polynucleotides of step (ii) using random primers;

A process comprising the steps of (i) generating a 3'-overhang on one side of the starting double-stranded polynucleotides by digesting with at least one restriction enzyme; (ii) treating the polynucleotides of step (i) with exonuclease III to generate single-stranded polynucleotides; and (iii) producing a pool of single-stranded polynucleotides having unidirectional sequential deletion by treating the single-stranded polynucleotides of step (ii) with a single-strand specific 5'→3' exonuclease followed by removing aliquots of the reaction mixture at a chosen time interval and further blocking the activity of the exonuclease.

A process comprising the steps of (i) conducting a polymerase chain reaction on the starting double-stranded polynucleotides using only one kind of oligonucleotide among forward and reverse primers; (ii) isolating the resulting single-stranded polynucleotides from the starting double-stranded polynucleotides; and (iii) conducting a polymerization process on the single-stranded polynucleotides of step (ii) using random primers;

A process comprising the steps of (i) conducting a polymerase chain reaction on the starting double-stranded polynucleotides using only one kind of oligonucleotide among forward and reverse primers; (ii) isolating the resulting single-stranded polynucleotides from the starting double-stranded polynucleotides; and (iii) treating the single-stranded polynucleotides of step (ii) with a single-strand specific 5'→3' exonuclease followed by removing aliquots of the reaction mixture at a chosen time interval and further blocking the activity of the exonuclease; and A process for preparing the steps of (i) isolating a single-stranded polynucleotide from a viral vector or plasmid vector which has at least one starting polynucleotide insert; and (ii) conducting a polymerization process on the single-stranded polynucleotides of step (i) using random primers.

Step 2: The second step of the inventive method may comprise the steps of (i) conducting at least one cycle wherein the primers are extended to the end of the unidirectional single-stranded DNA fragments used as templates; (ii) conducting at least one subsequent cycle wherein each of the resulting extended polynucleotides of step (i) is further extended to the end of an unidirectional single-stranded DNA fragment other than the unidirectional single-stranded DNA fragment used in step (i) by means of template switching; and (iii) repeating step (ii) until recombinant polynucleotides of desired length are obtained.

Specifically, the unidirectional single-stranded polynucleotide fragments of various lengths prepared in Step 1 are mixed together, a specific oligonucleotide having a nucleotide sequence complementary to the single-stranded polynucleotide fragments are added thereto, and a polymerase chain reaction is carried out under a proper stringency. Then, the specific oligonucleotide serves as a primer of polymerase chain reaction and is elongated gradually at one direction (5'→3') in each turn of reactions, whereby the recombination reaction occurs. The synthesized polynucleotides are separated into single strands by denaturation process and re-annealed. At this time, the synthesized polynucleotide may be annealed with other polynucleotide fragment containing a homologous sequence.

More specifically, a mixture of double-stranded polynucleotides can be denatured by heat and consequent polymerase chain reaction consists of the following three steps. First, double-stranded template DNA is treated at 90 to 98° C. for 10 sec to 5 min in order to separate into single-strands (denaturation). Thereafter, by lowering the temperature, previously added primers are annealed with a complementary single-stranded template DNA(annealing). This step is carried out at 40 to 72° C. for 10 sec to 2 min. Then, upon regulation of the temperature within a range of 70 to 78° C., four kinds of dNTPs(dATP, dGTP, dCTP, dTTP) in the reaction mixture begin to react and a is DNA complementary to the template DNA is synthesized and elongated. The reaction time depends on the length of DNA being synthesized.

In case of producing various recombinant DNAs in such a manner from two or more polynucleotides having homologous nucleotide sequences, a polynucleotide may extend from an oligonucleotide primer, which is capable of hybridizing with at least one of the starting polynucleotides, up to the 5' end of the unidirectional single-stranded DNA fragment used as a template in a cycle of synthesis; and the resulting polynucleotide may further extend to the end of other unidirectional single-stranded polynucleotide originating from other starting polynucleotide by template switching in the next cycle. At this time, a recombination boundary is formed between the oligonucleotides synthesized by employing as templates unidirectional single-stranded polynucleotides originating from different starting polynucleotides.

In Step 2 for the extension of polynucleotide, the unidirectional single-stranded polynucleotide fragments prepared in Step 1 are employed only as templates for generating the recombinant DNAs and, accordingly, the primers added at the begining are extended gradually to one direction (5'→3') using them as templates through the repetitive PCR to result in generation of recombinant polynucleotides.

In Step 2, the DNA recombination is conducted by periodically repeating the steps of denaturation, annealing and extension at the presence of DNA polymerase for the desired period. The degree of recombination depends on the homology between the groups of single-stranded polynucleotides derived from different starting polynucleotides.

Step 3: By sufficiently repeating the PCR cycles of Step 2 and amplifying the resulting mutant recombinant polynucleotides by a normal PCR method, a recombinant double-stranded DNA library is prepared. The recombinant DNA library thus obtained may consist of various kinds of mutant double-stranded polynucleotides which contain in a molecule the identical and heterogenous regions as compared with corresponding regions of any one of the starting double-stranded polynucleotides. The nucleotide sequence of the recombinant DNA may be determined by a conventional method, e.g., Maxam-Gilbert's method (Maxam, A. M and Gilbert, W., *Mol. Biol.*(*Mosk*), 20: 581–638 (1986)), Dideoxy method (Messing, J. et al., *Nucleic Acids Res.*, 24; 309–321(1981)), or a method using DNA fluorescence marker and automated DNA sequence analyzer.

The present invention further provides a method for constructing a recombinant DNA library for screening a desired gene using the recombinant DNAs obtained by the above method. Specially, it comprises the steps of inserting the mutant recombinant double-stranded DNA obtained in Step 3 into an appropriate expression vector, introducing the resulting expression vector into an expression cell to obtain a library containing a plurality of clones; screening a desired polynucleotide from the clones; and expressing a protein from the polynucleotide by a conventional method. Suitable expression methods include: producing and accumulating a gene product in cells; secreting a gene product from a cell and accumulating them in a medium; secreting a gene product into a periplasm; and the like methods. For screening a desired gene product from a recombinant DNA library, the methods known in the art, e.g. immunochemical method, radiochemical method, a method employing surface expressing system, and gene chip screening method, may be employed alone or in combination. In preparing the recombinant DNA library, any expression vector that operates in a selected host cell may be employed, exemplary vectors including conventional vectors of phage, plasmid, phagemid, viral vector and artificial chromosome known in the art. The method-for constructing the expression vector is well known in the art, e.g., in Sambrook, J. et al., *Molecular Cloning: A Laboratory Manual*, $2^{nd}$ ed., (1989) Cold Spring Harbor Laboratory Press, N.Y. A suitable host cell may be transformed with the resulting expression vector. The suitable host cells for expressing the recombinant DNA include a bacterium such as *E. coli, Bacillus subtilis* and *B. brevis*, etc.; an Actinomyces such as *Streptomyces lividans*; a yeast such as *Saccharomyces serevisiae*; a fungus such as *Aspergillus oryzae, A. nidulans* and *A. niger*; an animal cell such as COS-7, CHO, Vero and mouse L cells; an insect cell; and a plant cell.

The present invention provides a method for preparing various, random, mutant recombinant DNAs in a short period of time. Specifically, a library of mutant recombinant polynucleotides can be obtained by adding oligonucleotide primers to a mixture of unidirectional single-stranded DNA fragments derived from two or more of homologous nucleic acid sequences or polynucleotides; and conducting repetitive PCR to obtain the library of mutant recombinant polynucleotides, wherein random recombinations between the nucleotide sequences of the single-stranded oligonucleotide fragments are occurred.

The recombinant DNAs prepared by the inventive method may be genes encoding proteins, e.g., enzymes, antibodies, vaccines(antigens), hormones, growth factors, binding proteins and plasma proteins. For instance, the recombinant DNA may encode an enzyme, said enzyme being selected from the group consisting of hydrolase, lyase, transferase, oxidoreductase, ligase and isomerase. A preferred embodiment of the present invention provides a method for constructing a recombinant DNA library by preparing a recombinant gene (recombinant DNA) having a random mutation between *Serratia marcescens* chitinase gene (SEQ ID NO: 1, designated "m-chi") and *S. liquefaciens* chitinase gene (SEQ ID NO: 2, designated "l-chi") and cloning the recombinant gene. About 10,000 clones were prepared by the inventive method and, among them, 10 clones were randomly selected to determine the nucleotide sequences thereof. Comparison of their nucleotide sequences with those of the two wild-type genes exhibited that one time of recombination is occurred between the two genes in recombinant clones 3, 4 and 10; two times of recombinations, in recombinant clones 1, 2, 7 and 8; three times of recombinations, in recombinant clones 6 and 9; and four times of recombinations, in recombinant clone 5. These results demonstrate that the inventive method is effective in constructing a recombinant DNA library having a random recombination between two or more kinds of polynucleotides.

The inventive method for constructing a recombinant DNA library has a wide applicability. This in vitro mutagenization method may be used in a laboratory as means for biochemical studies. Since it allows to understand the mechanism of a protein involving in the maintenance and regulation of life in a molecular level, it may be used as means for producing and screening a proten such as an enzyme, antibody, vaccine (antigen), hormone, adsorption protein or plasma protein, thereby inducing the change of substrate specificity, change of reaction specificity, increase of activity, change of antigenicity, change of safety of a protein. Therefore, it is ultimately applied to various industrial fields for the development of a medicine, improvement and enhancement of food quality, improvement of energy conversion rate, breeding and quality improvement in livestock and fishery, development and production of novel chemical product, etc. (Chartrain M. et al., *Curr. Opin. In Biotech.*, 11: 209–214 (2000); Miyazaki K. et al., *J. Mol Biol.*, 297: 1015–1026 (2000); Giver, L. and Arnold, F. H., *Curr. Opin. Chem. Biol.*, 2: 335–338 (1998); Kumamaru, T. et al., *Nat. Biotechnol.*, 16: 663–666 (1998); and Patten, P. A., *Curr. Opin. Biotechnol.*, 8: 724–733 (1997)).

The present invention is further defined in the following Examples. It should be understood that these Examples, while indicating preferred embodiments of the invention, are given by way of illustration only. From the above discussion and these-Examples, one skilled in the art can ascertain the essential characteristics of this invention, and without departing from the spirit and scope thereof, can make various changes and modifications of the invention to adapt it to various usage and conditions.

EXAMPLE 1

Generating Unidirectional Single-stranded Polynucleotide Fragments

A pool of unidirectional single-stranded polynucleotide fragments having random length was prepared from a pair of double-stranded polynucleotides which have regions of similarity with each other as follows:

1-1) Preparation of Unidirectional Single-stranded DNA Fragments by Reverse Transcription In an embodiment of the present invention, genes encoding chitinase of *Serratia marcescens* and *Serratia liquefaciens* (hereinafter, referred to as "m-chi" and "l-chi", respectively) were chosen as starting polynucleotides to be reassembled, the nucleotide sequences of which are described in FIG. 2.

HindIII/Xba I fragments containing m-chi and l-chi genes, respectively, were cloned into pUC19, resulting in pUC19-m-chi and pUC19-l-chi. These plasmids were treated with Nde I, gap-filled with Klenow and then digested with HindIII. The resulting DNA inserts of about 2-kb were ligated to the HindIII/EcoRV backbone of pBluescript II KS (Stratagene) to give 5-kb recombinant plasmids. The resulting plasmids, pBSK-m-chi and pBSK-l-chi, were then linearized with Spe I.

200 ng of the linearized plasmids was added to transcription buffer solution [40 mM Tris-HCl(pH 7.9), 6 mM $MgCl_2$, 2 mM spermidine, 10 mM NaCl, 10 mM DTT] supplemented with 0.5 mM each rNTP, 40 units of RNasin and 17 units of T3 RNA polymerase up to the total volume of 20 $\mu l$ and incubated at 37° C. for 1 hour. The RNA transcripts of the m-chi and l-chi genes obtained by the above in vitro transcription were analyzed by electrophoresis on 1% agarose gel. The bands of 5-kb plasmid and RNA transcripts are detected in lanes 2 and 3 of FIG. 3(a). Purified with RNAeasy column (Qiagen), 200 ng of each RNA transcribed from the two chitinase genes was mixed. The RNA mixture was added to the reaction buffer[10 mM Tris-HCl(pH 8.3), 15 mM KCl, 0.6 mM MgCl$_2$, 0.2 mM DTT] supplemented with 6 µg of random hexamer (Genotech, Inc.), 0.2 mM each dNTP, 40 units of RNasin and 50 units of M-MLV reverse transcriptase to the total volume of 50 µl and reverse transcription was performed at 37° C. for 1 hour. After the reverse transcription, the RNA templates were removed by incubating the reaction mixture with 20 ng of RNase I at 37° C. for 1 hour.

Since the random hexamer can be hybridized with the template RNA at all the location thereof by chance, nucleotide extension from the random hexamer generates unidirectional single-stranded DNA fragments with random length.

Figure 3:
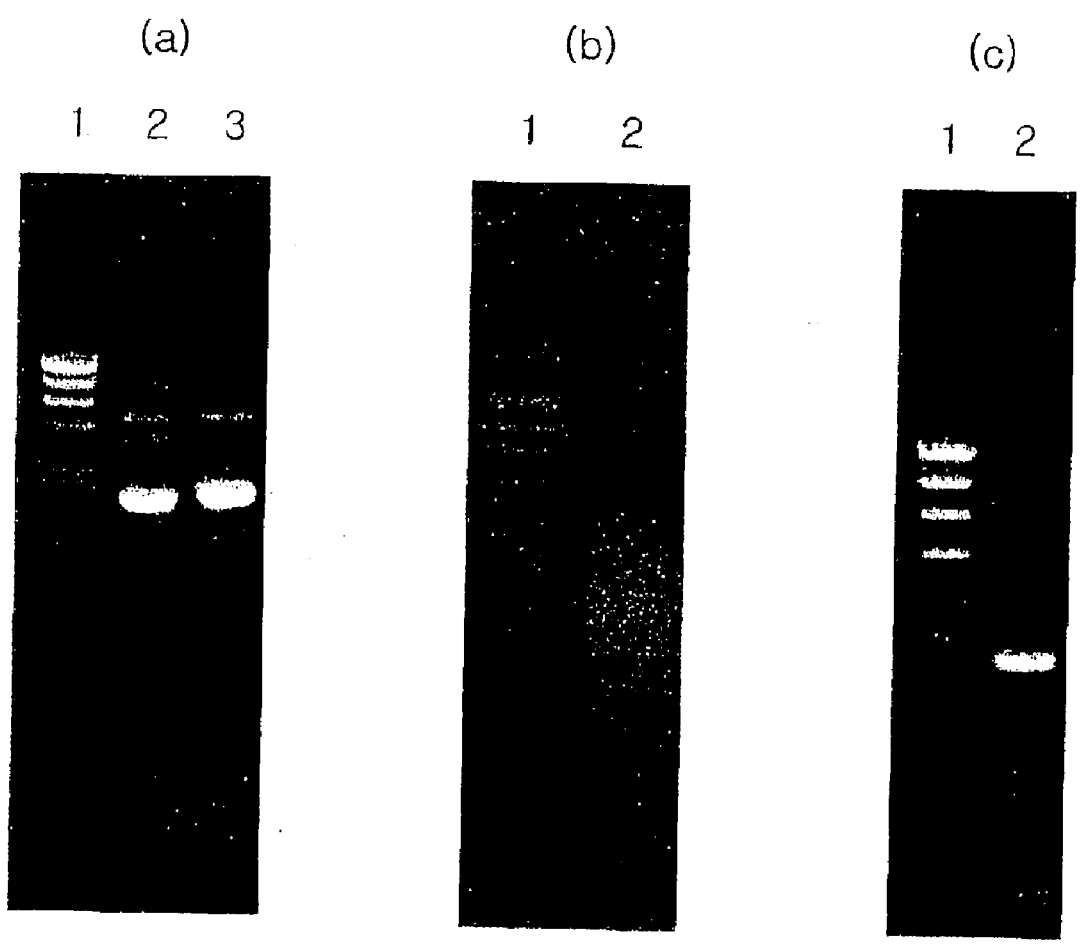
FIG. 3 displays the result of 1% agarose gel electrophoresis, wherein lane 1 of (a) is a standard DNA size marker (23, 9.4, 6.6, 4.4, 2.3, 2.0 and 0.56 kb from the top), lane 2 of (a), in vitro transcription product of chitinase gene of *Serratia marcescens*, lane 3 of (a), in vitro transcription product of chitinase gene of *Serratia liquefaciens*; lane 1 of (b) is a standard DNA size marker (23, 9.4, 6.6, 4.4, 2.3, 2.0 and 0.56 kb from the top), and lane 2 of (b), single-stranded DNA fragments produced by reverse transcription; and lane 1 of (c) is a standard DNA size marker (23, 9.4, 6.6, 4.4, 2.3, 2.0 and 0.56 kb from the top), and lane 2 of (c). PCR products produced by employing unidirectional single-stranded DNA fragments as templates.

The products of reverse transcription were electrophorezed on 1% agarose gel (lane 2, FIG. 3(b)) and the single-stranded DNA fragments were cut and purified using a Geneclean kit (Bio 101).

1-2) Preparation of Unidirectional Single-Strand DNA Fragments with Serial 5' Deletions This method is based on two useful features of exonuclease III: (i) processive digestion at a very uniform rate and (ii) failure to initiate digestion at DNA ends with 4-base 3'-protrusions(Henikoff, S., Gene 28, 351–359, 1984).

Plasmid pGEM-T (Promega) having m-chi gene of 30 µg was linearized with a pair of restriction enzymes, Sph I and Nco I, wherein Sph I produces 4-base 3'-protrusions resistant to the exonuclease III digestion while Nco I generates 4-base 5'-overhanging ends. As for l-chi gene, the above process was conducted as same. The linearized polynucleotides dissolved in exonuclease III reaction buffer[66 mM Tris-HCl (pH 8.0), 0.66 mM MgCl$_2$] up to the volume of 60 µl were digested with 2 units of exonuclease III. 2.5 µl of aliquot was then removed at intervals of twenty seconds, and the enzyme reaction was terminated. The resulting aliquot was mixed with 7.5 µl of S1 nuclease mix [S1 nuclease reaction buffer (300 mM potassium acetate, pH 4.6, 2.5 M NaCl, 10 mM ZnSO$_4$, 50% glycerol) plus 50 units of S1 nuclease] and then placed at room temperature for 15 minutes.

After the S1 nuclease was inactivated by S1 stop solution [300 mM Tris base, 50 mM EDTA], polymerization was performed at 37° C. for 30 min by adding Klenow and then the products were cleaved with Sac I. The resulting double-stranded DNA fragments having random deletions sequentially were analyzed by electrophoresis on 1% agarose gel. The DNA fragments were extracted from the gel and reacted with 2 units of exonuclease III for 1 hour to produce a set of single-stranded DNA fragments having unidirectional deletions thereon.

1-3) Preparation of Unidirectional Single-strand DNA Fragments Using Single-Stranded DNA as a Template Plasmid pGEM-T (Promega) having each of m-chi and l-chi genes of 5 µg was linearized with a pair of restriction enzymes, Sph I and Nco I. The linearized polynucleotides dissolved in exonuclease III reaction buffer[66 mM Tris-HCl (pH 8.0), 0.66 nM MgCl$_2$] up to the-volume of 60 µl were digested with 2 units of exonuclease III at 37° C. for 30 min.

The resulting linearized single-stranded polynucleotides were used as templates to generate the single-stranded DNA fragments in a polymerization mix[10 units of Klenow, 6 µg of random hexamers, 0.1 mM each dNTP, 10 mM Tris-HCl (pH 7.5), 5 mM MgCl$_2$, 7.5 mM DTT] at 37° C.

The resulting unidirectional single-stranded DNA fragments were analyzed by electrophoresis on 1% agarose gel and subsequently purified using a Geneclean kit(Bio 101).

EXAMPLE 2

Reassembly of Polynucleotides by Polymerase Chain Reaction Using the Unidirectional Single-stranded DNA Fragment as a Template The unidirectional single-stranded DNA fragments obtained above served as templates for polymerase chain reaction. A reaction mixture contained 20 ng of the single-stranded DNA fragments, 0.2 mM each dNTP, 2 MM MgCl$_2$, 50 mM KCl, 10 mM Tris-HCl(pH 8.8), 0.1% Triton X-100, 2 units of Vent DNA polymerase (New England BioLabs) and 25 pmole of a primer in a total volume of 50 µl, wherein the primer being an oligonucleotide (SEQ ID NO: 24) having the nucleotide sequence identical to those at the 5' termini of m-chi and l-chi genes. PCR was carried out on an MJ Research thermal cycler (PTC-100) at 94° C. for 3 min; 94° C. for 30 seconds, 55° C. for 30 seconds, 72° C. for 30 seconds(30 cycles); and 72° C., 5 min. For the amplification of a full-length DNA, secondary PCR was carried out on the above PCR products using 25 pmole of a 3'-specific oligonucleotide (SEQ ID NO: 25) as a primer. PCR was carried out on an MJ Research thermal cycler (PTC-100) at 94° C. for 3 min; 94° C. for 30 seconds, 55° C. for 30 seconds, 72° C. for 30 seconds(30 cycles); and 72° C., 5 min. The resulting PCR products of about 1.7 kb were analyzed by 1% agarose gel electrophoresis (lane 2, FIG. 3(c)).

EXAMPLE 3

Sequencing and Screening

The PCR products of example 2 were extracted from the gel by a Geneclean kit(Bio 101), digested with HindIII and Xba I, and ligated to the HindIII/Xba I backbone of pBluescript II KS. The resulting recombinant plasmid was transformed to E. coli JM83 and transformants were selected on LB-agar plates supplemented with 100 µg/ml ampicillin. Plasmid DNA was isolated from the randomly chosen 14 colonies by Qiagen Spin Miniprep kit(Qiagen) and digested with restriction enzymes, Not I, Pst I and Hinc II.

Figure 4:
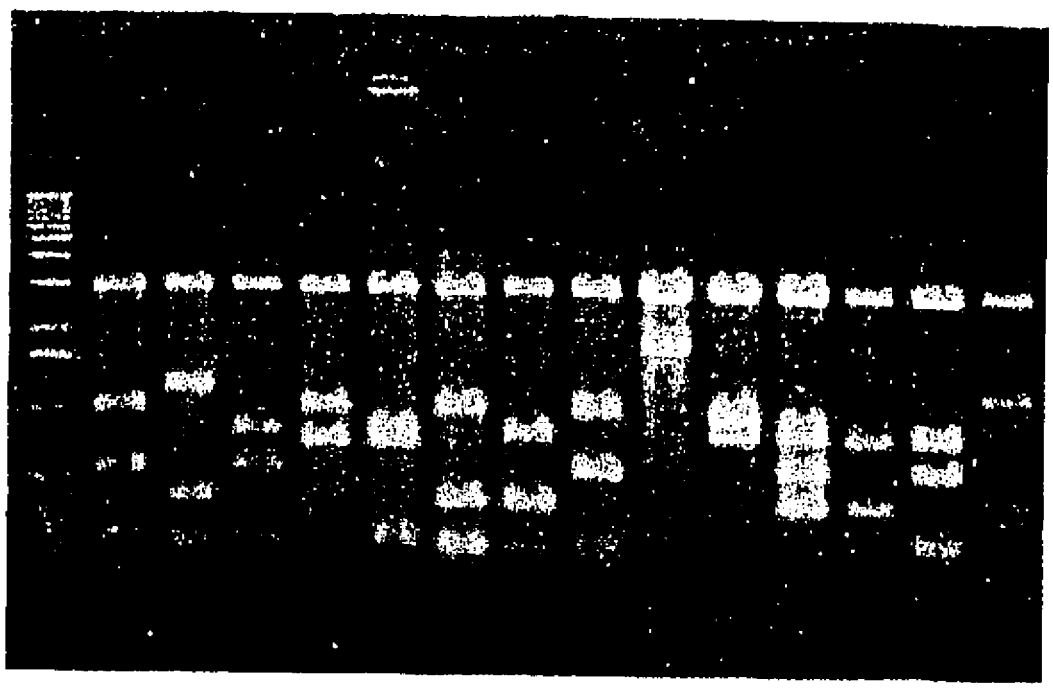
FIG. 4 represents the result of 1% agarose gel electrophoresis of the digestion products obtained by extracting the plasmid DNAs from 14 clones randomly selected from the recombinant DNA library prepared by the inventive method and digesting the plasmid DNAs with restriction enzymes NotI, PstI and HincII. Lane 1 is a standard DNA size marker and lanes 2 to 15, digestion products of the plasmid DNAs from the randomly selected 14 clones.

FIG. 4 shows various sizes of DNA resolved by usual electrophoresis on 1% agarose gel. The band patterns of DNA fragments of l-chi gene cleaved with the same three restriction enzymes are shown in lane 5, those of m-chi gene in lanes 8 and 13. The remaining lanes represent patterns of random recombinant DNA reassembled from m-chi and l-chi genes, the patterns different from those of wild type DNA fragments. These results show that at least 11 clones of the randomly selected 14 clones contain recombinant DNA reassembled from a pair of the wild-type DNA.

To identify the resulting recombinant DNA, HindIII/Xba I fragment of the 10 plasmids was sequenced using the ABI PRISM Dye terminator Cycle Sequencing Kit (PE Biosystems) and the sequences were compared with those of the wild-type m-chi and l-chi genes, alignments of which were shown in FIG. 5 and further depicted in the schematic diagram of FIG. 6.

As shown in FIG. 6, recombination between the two wild-type genes took place once as for the recombinant DNA clones 3, 4 and 10; twice as for clones 1, 2, 7 and 8; three times as for clones 6 and 9; and four times as for clone 5. These results suggest that the method of the present invention using unidirectional single-stranded polynucleotides can efficiently generate a random recombinant DNA library from two or more kinds of starting polynucleotides.

Figure 7:
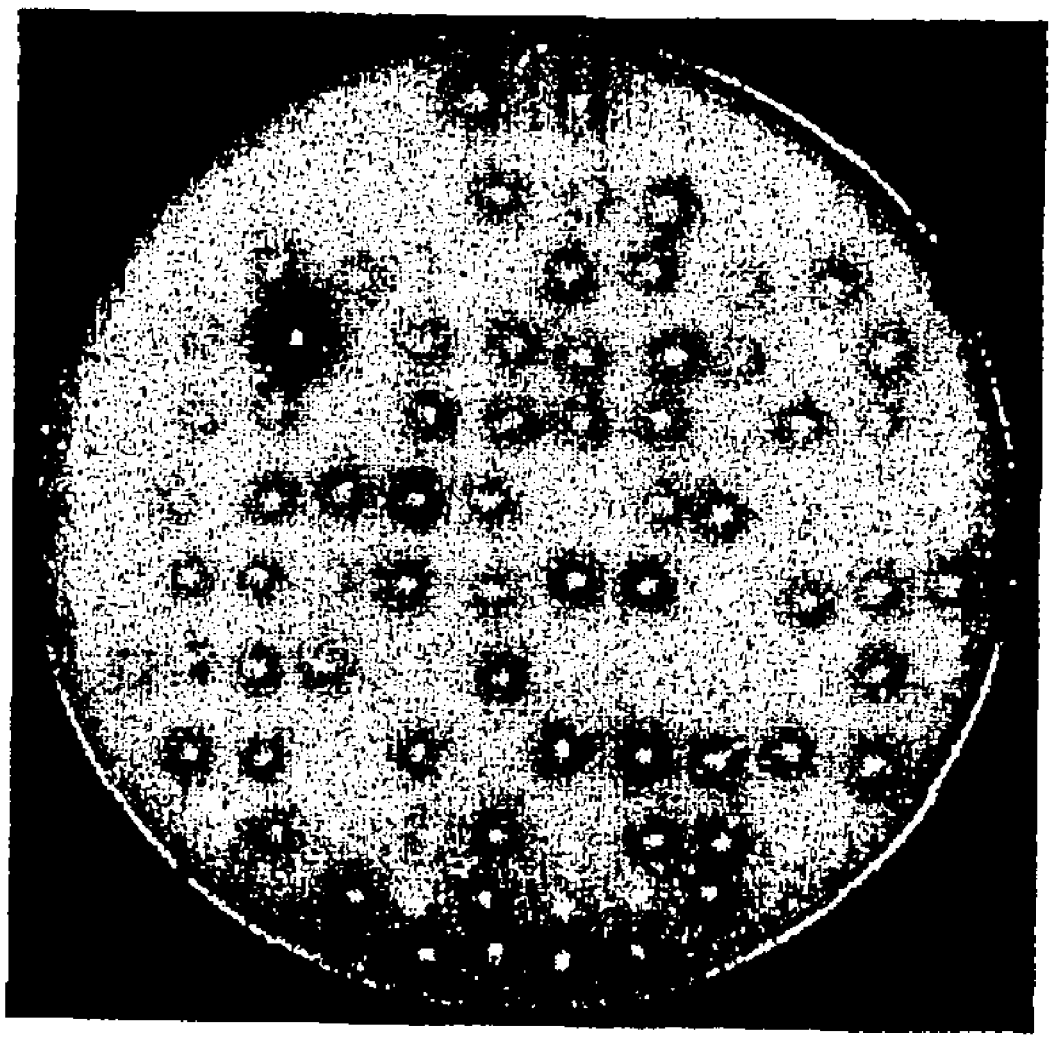
FIG. 7 shows the difference in the sizes of the clear zones made by the colonies expressing the recombinant chitinase genes on LB-agar plates containing 100 μg/ml ampicillin and 0.5% swollen chitin, depending on the chitin decomposition capabilities of the colonies.
Figure 9:
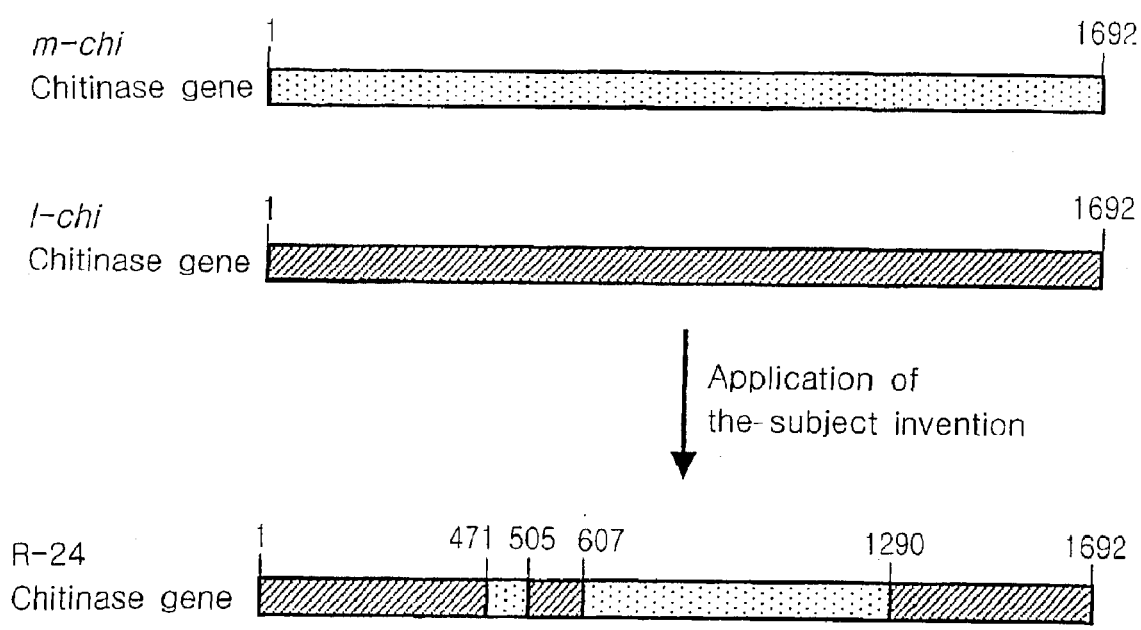
FIG. 9 is a schematic diagram showing the constitution of R-24 chininase gene in comparison with the two wild-type genes.

To screening a recombinant polynucleotide encoding a chitinase which has specific activity higher than that of wild-type enzyme, the colonies were transferred by replica-plating method to LB-agar plates containing 100 µg/ml ampicillin and 0.5% swollen chitin, and incubated at 37° C. overnight until clear plaques were developed. About 800 colonies were screened according to the degree of their clearance. FIG. 7 shows the variance of the sizes of clear zones formed by the colonies expressing the recombinant chitinase depending on their chitin decomposing activities different from each other. A chitinase produced by a colony forming a clear zone larger than wild type was designated R-24 chitinase. Plasmid DNA was extracted from the clone by Qiaprep Spin Miniprep method (Qiagen) and the nucleotide sequence of R-24 chininase gene was analyzed. FIG. 8 compares the nucleotide sequence of R-24 chininase gene (SEQ ID NOs: 13) with those of two wild-type genes, i.e., l-chi gene (SEQ ID NO: 1) and m-chi gene (SEQ ID NO: 2). FIG. 9 is a schematic diagram showing the constitution of R-24 chininase gene in comparison with the two wild-type genes. From FIG. 9, it can be seen that R-24 chitinase gene was produced by four times of recmbinations between the two wild-type genes.

Table 1 shows the comparison of the specific activity of R-24 chitinase with those of the two wild-type chitinases.

TABLE 1

Specific activities of the wild-type chitinases and recombinant R-24 chitinase

| Chitinase | Specific activity (U/mg) |
|---|---|
| *Serratia marcescens* chitinase | 150.6 |
| *Serratia liquefaciens* chitinase | 201.3 |
| R-24 chitinase | 227.2 |

As can be seen from Table 1, specific activity of R-24 chitinase is higher than *Serratia marcescens* chitinase and *Serratia liquefaciens* chitinase by factors of 1.5 and 1.1, respectively.

EXAMPLE 4

Directed Evolution of a Chitosanase for Thermostability 4-1) Preparation of Mutant Chitosanases by Error-prone PCR About 0.5-kb DNA fragment obtained by EcoRV/Sal I double digestion of pBR322 was inserted into EcoRV/Sal I digestion site of pBluescript II SK. The resulting vector construct was then cut with Xba I and EcoR I, and ligated to about 1.4-kb chitosanase gene obtained by digesting *Bacillus sp.* (KCTC 0377BP) with same restriction enzymes, resulting in a recombinant vector construct, pBSK-csn-322, containing chitosanase gene.

The pBSK-csn-322 was used as a template for error-prone polymerase chain reaction. Each 50 pmole of primers csn-Xba I (SEQ ID NO: 26) and csn-c1(SEQ ID NO: 27) was used for an error-prone PCR reaction which was performed in 100 µl of PCR mix comprising 10 mM Tris-HCl(pH 8.3), 50 mM KCl, 4 mM MgCl$_2$, 0.2 mM dATP, 0.2 mM dGTP 1 mM dCTP, 1 mM dTTP, 0.15 mM MnCl$_2$, 10 ng of template DNA and 5 units of Taq polymerase using an MJ Research Thermal cycler (PTC-200). The PCR conditions were as follows: 94° C. for 3 min; 94° C. for 30 seconds, 55° C. for 30 seconds and 72° C. for 30 seconds(30 cycles); and followed by 72° C., 5 min.

The resulting 1.4-kb DNA fragment was digested with Xba I and EcoR I, then ligated to Xba I/EcoR I backbone of pBSK-csn-322. The resulting recombinant plasmid was transformed to *E. coli* JM83 and positive transformants were selected by culturing them on LB-agar plates supplemented with 100 µg/ml ampicillin at 37° C. for 18 hours. The colonies formed on the plates were replica-plated onto a fresh plates and incubated at 37° C. for 20 hours. The petri dish containing the colonies was heated on a water bath at 70° C. for 15 minutes, and then 50 mM Na-acetate buffer solution containing 0.1% chitosan and 1% agarose was poured-onto the LB-agar plates. After the plates was placed at 37° C. for 24 hours, colonies still having chitosanase activity to produce clear plaques were selected using 0.2% Congo Red. As a result of aforementioned process, 9 positive clones having improved thermal stability were isolated out of about 12,000 clones. Plasmid DNAs were extracted from the clones by Qiaprep Spin Miniprep method (Qiagen) and the nucleotide sequences of chitosanase genes therein were analyzed. Table 2 shows the amino acid substitution sites of thermostable mutant chitosanases produced by error-prone PCR in comparison with the wild-type chitosanase.

TABLE 2

Amino acid substitution sites of thermostable mutant chitosanases produced by error-prone PCR

| Mutant chitosanase | Amino acid substitution sites |
|---|---|
| d10–68 | D305G |
| e3–97 | E308G |
| e4–12 | I389M |
| e15–20 | T131I, N368D |
| e18–5 | S24P, T277A, N368D |
| e22–23 | K172E, S376P |
| e26–27 | Q159R |
| e26–98 | E107D, Q442R |
| e30–97 | S376P, Y451C |

4-2) Construction of the First Recombinant DNA Library and Screening

DNA reassembly process according to the present invention was carried out using the 9 mutant chitosanase genes selected in 4-1) above as starting polynucleotides.

The plasmids extracted from the 9 clones were mixed in each quantity of 500 ng and then the linearized DNA fragments of about 4.9-kb in size were obtained by Xho I digestion. The linearized fragments of 200 ng were transcribed in 20 µl of transcription buffer solution[40 mM Tris-HCl, pH 7.8, 6 mM MgCl$_2$, 2 mM spermidine, 10 mM NaCl, 10 mM DTT] containing 0.5 mM each rNTPs, 40 units of RNasin and 17 unist of T3 RNA polymerase at 37° C. for 1 hour. The resulting RNA transcripts of the mutant genes for chitosanase were purified in RNAeasy column (Qiagen).

Reverse Transcription was conducted on 200 ng of the RNA in 50 µl of reaction solution[10 mM Tris-HCl, pH 8.3, 15 mM KCl, 0.6 mM MgCl$_2$, 0.2 mM DTT] containing 6 µg of random hexamer, 0.2 mM each dNTPs, 40 units of RNasin and 50 units of M-MLV reverse transcriptase at 37° C. for 1 hour. The template RNA was then removed by RNase I at 37° C. for 1 hour. Through the reverse transcription process, unidirectional single-stranded DNAs of random size were synthesized from the random hexamer annealed with the template RNA. The resulting single-stranded DNA was analyzed by 1% agarose gel electrophoresis and extracted from the gel using a Geneclean kit(Bio 101).

The unidirectional single-stranded DNA fragments obtained above served as templates for polymerase chain reaction. A reaction mixture contained 10 ng of single-stranded DNA fragments, 0.2 mM each dNTP, 2 mM MgCl$_2$, 50 mM KCl, 10 mM This-HCl(pH 8.8), 0.1% Triton X-100, 2 units of Vent DNA polymerase (New England BioLabs) and 25 pmole of csn-Xba I primer(SEQ ID NO: 26) in a total volume of 50 µl. PCR was carried out on an MJ Research thermal cycler (PTC-100) at 94° C. for 3 min; 94° C. for 30 seconds, 55° C. for 30 seconds, 72° C. for 30 seconds(30 cycles); and 72° C., 5 min. The full-length DNA of about 1.4-kb in size was then amplified by PCR using 25 pmole of csn-c1 primer (SEQ ID NO: 27) under the same conditions as described above. The resulting 1.4-kb DNA was digested with Xba I and EcoR I and then ligated to the Xba I/EcoR I backbone of pBSK-csn-322. The resulting plasmid was transformed to *E. coli* KM83 and positive transformants were selected on LB-agar plates supplemented with 100 μg/ml ampicillin at 37° C. for 20 hours. Grown colonies were transferred onto fresh plates by replica-plating method and incubated at 37° C. for 20 hours. The plates were heated on water bath at 75° C. for 20 minutes, and then 50 mM Na-acetate solution containing 0.1% chitosan and 1% agarose was added onto the LB-agar plates. After incubated at 37° C. overnight, colonies still having chitosanase activity resulting in clear plaque around them notwithstanding the heat treatment were selected on 0.2% Congo Red.

Through the aforementioned process, 23 clones having improvement in heat resistance compared to the 8 clones obtained by error-prone PCR were selected out of about 12,000 clones.

4-3) Construction of Secondary Recombinant DNA Library and Screening

Secondary recombinant DNA library was constructed with the 23 mutant chitosanase genes, which had been obtained by the screening of the first recombinant DNA library, through the same process as described in 4-2) above. After heated at 80° C. for 30 min, the resulting colonies of 16,000 or more were screened for mutant chitosanase having more improved thermal stability than the starting materials, 23 mutant chitosanases. Two mutants were selected and polypeptides encoded by them were designated as M-13 and M-20, respectively.

4-4) Determination of Amino Acid Substitution Sites and Analysis for Thermal Stability of M-13 and M-20

From the colonies expressing the mutant chitosanases, M-13 and M-20, plasmid DNAs were extracted and the nucleotide sequences of the chitosanase genes were analyzed. FIG. 10 represents the comparison between the sequences of wild-type chitosanase and the genes encoding M-13 and M-20, respectively. Further, deduced amino acid sequences of the wild-type chitosanase and the thermostable M-13 and M-20 mutants were analyzed and the amino acid substitution sites of the mutant chitosanase different from those of the wild-type chitosanase were presented in Table 3.

TABLE 3

Amino acid substitution sites of thermostable mutant chitosanases produced by the inventive method

| Mutant chitosanase | Amino acid substitution sites |
| --- | --- |
| M-13 chitosanase | N60Y, E107D, Q159R, N228T, D305G, E308G, N368D, S376P, F384L, I389M, D435G |
| M-20 chitosanase | S24P, E107D, Q159R, N286D, D305G, E308G, N357D, N368D, N371D |

As can be seen from Table 3, when compared with the substitution sites present in the mutants prepared by the error-prone PCR as shown in Table 2, it was exhibited that the substitution sites present in seven mutants, i.e., E107D, Q159R, D305G, E308G, N368D, S376P and I389M, were accumulated in M-13 chitosanase; and the substitution sites present in six mutants, i.e., S24P, E107D, Q159R, D305G, E308G and N368D, in M-13 chitosanase, by the recombination. This result demonstrates that the method of the present invention is useful for the efficient production of recombinant polynucleotides. On the other hand, it can be seen that in addition to the substitution sites resulted from the recombination between the parent mutants, net 4 and 3 mutation sites were introduced into M-13 and M-20 mutant chitosanases, respectively, during the process of the inventive method.

In order to determine the thermal stabilities of the mutant chitosanases, the wild-type chitosanase, M-13 mutant and M-20 mutant were treated at 60 C and the remaining activities according to time were determined. FIG. 11 shows the differences in the thermal stabilities of the wild-type chitosanase, M-13 mutant and M-20 mutant. In FIG. 11, half-lives($T_{1/2}$) of the enzymes, which means that the activity thereof decreases by 50% as compared to the initial activity, are 5.1 min for the wild-type, 6.9 hours for M-13 mutant and 11.6 hours for M-20 mutant. This result shows that the thermal stabilities at 60° C. of M-13 and M-20 mutants increased by 81 and 136 folds, respectively, than the wild-type chitosanase.

As can be appreciated from the disclosure and the examples above, the method of the present invention can be used for in vitro recombination of homologous polynucleotides and the directed molecular evolution of proteins for desired properties. It is also contemplated that the method of the present invention has advantages over the conventional methods in that random diversity of the polynucleotides is achieved in a short time.

While the invention has been described with respect to the above specific embodiments, it should be recognized that various modifications and changes may be made to the invention by those skilled in the art which also fall within the scope of the invention as defined by the appended claims.

What is claimed is:

1. A method for producing recombinant polynucleotides comprising the steps of:
   (a) generating a pool of unidirectional single-stranded polynucleotide fragments randomized in length from at least one starting polynucleotide to be reassembled, which have regions of similarity with each other;
   (b) conducting a polymerization process comprising multi-cyclic extension reactions, wherein the unidirectional single-stranded polynucleotide fragments prepared by step (a) serve as templates sequentially and specific oligonucleotides are added to the reaction mixture as primers, the primers being extended by means of template switching to produce at least one recombinant polynucleotide, and the resulting recombinant polynucleotides being different from the starting polynucleotides in nucleotide sequence; and
   (c) conducting a polymerase chain reaction using at least one specific primer to amplify the recombinant polynucleotides prepared by step (b).

2. The method of claim 1, wherein step (a) comprises:

(i) conducting a transcription process to produce RNA from at least one starting polynucleotide; and (ii) conducting a reverse transcription process, wherein random primers are used as primers and the RNA transcript of step (i) as a template.

3. The method of claim 1, wherein step (a) comprises:

(i) generating a 3'-overhang on one side of the starting double-stranded polynucleotide by digesting with at least one restriction enzyme;

(ii) producing a pool of double-stranded polynucleotides having unidirectional sequential deletion by treating the reaction mixture of step (i) with exonuclease III followed by removing aliquots of the reaction mixture at a chosen time interval and further blocking the activity of the exonuclease III;

(iii) treating the resulting double-stranded polynucleotides having a 5'-overhang with an S1 nuclease and a DNA polymerase to form a blunt end thereof;

(iv) generating a new 3'-overhang to the same side which has 3'-overhang in step (i); and (v) treating the polynucleotides of step (iv) with exonuclease III to generate single-stranded polynucleotide fragments.

4. The method of claim 1, wherein step (a) comprises:

(i) generating a 3'-overhang on one side of the starting double-stranded polynucleotides by digesting with at least one restriction enzyme;

(ii) treating the polynucleotides of step (i) with exonuclease III to generate single-stranded polynucleotides; and (iii) conducting a polymerization process on the single-stranded polynucleotides of step (ii) using random primers.

5. The method of claim 1, wherein step (a) comprises:

(i) generating a 3'-overhang on one side of the starting double-stranded polynucleotides by digesting with at least one restriction enzyme;

(ii) treating the polynucleotides of step (i) with exonuclease III to generate single-stranded polynucleotides; and (iii) producing a pool of single-stranded polynucleotides having unidirectional sequential deletion by treating the single-stranded polynucleotides of step (ii) with a single-strand specific 5'→3' exonuclease followed by removing aliquots of the reaction mixture at a chosen time interval and further blocking the activity of the exonuclease.

6. The method of claim 1, wherein step (a) comprises:

(i) conducting a polymerase chain reaction on the starting double-stranded polynucleotides using only one kind of oligonucleotide among forward and reverse primers;

(ii) isolating the resulting single-stranded polynucleotides from the starting double-stranded polynucleotides; and (iii) conducting a polymerization process on the single-stranded polynucleotides of step (ii) using random primers.

7. The method of claim 1, wherein step (a) comprises:

(i) conducting a polymerase chain reaction on the starting double-stranded polynucleotides using only one kind of oligonucleotide among forward and reverse primers;

(ii) isolating the resulting single-stranded polynucleotides from the starting double-stranded polynucleotides; and (iii) producing a pool of single-stranded polynucleotides having unidirectional sequential deletion by treating the single-stranded polynucleotides of step (ii) with a single-strand specific 5'→3' exonuclease followed by removing aliquots of the reaction mixture at a chosen time interval and further blocking the activity of the exonuclease.

8. The method of claim 1, wherein step (a) comprises:

(i) isolating a single-stranded polynucleotide from a viral vector or plasmid vector which has at least one starting polynucleotide insert; and (ii) conducting a polymerization process on the single-stranded polynucleotides of step (i) using random primers.

9. The method of claim 1, wherein step (b) comprises the steps of:

(i) conducting at least one cycle wherein the primers are extended to the end of the unidirectional single-stranded DNA fragments used as templates;

(ii) conducting at least one subsequent cycle wherein each of the resulting extended polynucleotides of step (i) is further extended to the end of an unidirectional single-stranded DNA fragment other than the unidirectional single-stranded DNA fragment used in step (i) by means of template switching; and (iii) repeating step (ii) until recombinant polynucleotides of desired length are obtained.

10. The method of claim 1, wherein the specific oligonucleotides of step (b) have specific nucleotide sequences which is capable of hybridizing with at least one starting polynucleotide.

11. The method of claim 1, wherein the starting polynucleotide is a gene encoding any one of proteins selected from the group consisting of enzymes, antibodies, antigens, binding proteins, hormones, growth factors and plasma proteins, or a part thereof.

12. The method of claim 11, wherein the enzyme is selected from the group consisting of hydrolase, lyase, transferase, oxidoreductase, ligase and isomerase.

13. The method of claim 1, wherein the starting polynucleotide is a wild type DNA or a mutant type DNA obtained therefrom.

14. A method for constructing a recombinant DNA library, comprising the steps of inserting the recombinant polynucleotide prepared by the method of any one of claims 1 to 10 into a vector; and transforming an expression cell with said vector containing the recombinant polynucleotide to obtain a plurality of mutant clones.

15. The method of claim 14, wherein the vector is selected from the group consisting of a phage, a plasmid, a phagemid, a viral vector and an artificial chromosome.

16. The method of claim 14, wherein the expression cell is selected from the group consisting of bacteria, fungi, plant cells, animal cells and insect cells.

17. A method for evolving a polynucleotide toward a desired property which comprises screening recombinant polynucleotides having a desired functional properties from the recombinant DNA library constructed by the method of claim 14.

* * * * *

SEQUENCE LISTING

<160> NUMBER OF SEQ ID NOS: 27

<210> SEQ ID NO 1
<211> LENGTH: 1692
<212> TYPE: DNA
<213> ORGANISM: Serratia liquefaciens

<400> SEQUENCE: 1

```
atgcgcaaat ttaataaacc gctgttggcg ttgctgatcg cagcacgct  gtgctctgcg    60
gcgcaggccg ctgcaccggg caaacctacg ttggcctggg caataccaa  attcgccatt   120
gtcgaagtcg atcaagcggc gacggcttat aataatctgg tgaaagtaaa aagtgccgcc   180
gacgtttctg tttcatggaa tttatggaat ggcgatacccg gtaccacggc aaaagtatta   240
ttaaatggca agaagtttg  gagtggtgcc tcaaccggta gttcgggaac cgcaaacttt   300
aaggtgaata aggcggccg  ttatcaaatg caggtggcgt tatgcaacgc cgacggctgt   360
accgccagcg atgcaaccga aattgtggtg gcagataccg acggtagcca tttggcacct   420
ttaaaagaac ctttgttgga aaagaataag ccttataaac aagactccgg caaagtggtt   480
ggctcttatt tcgttgaatg gggcgtttac ggccgtaatt tcaccgtcga taaacttccg   540
gctcagaacc tgacgcacct gctgtacggc tttatcccta tctgtggcgg tgacggcatc   600
aacgacagcc tgaaagagat cgaaggcagc ttccaggcgt tacagcgttc ctgtcagggg   660
cgtgaagact taaggtatc  gatccacgat ccgttcgctg cgctgcagaa aggtcagaag   720
ggcgtgaccg cctgggacga cccctacaaa ggcaacttcg ccagttgat  ggcgttgaaa   780
caggcgcgcc cggacctgaa aatcctgccg tcgatcggtg gctggacgtt atccgatccg   840
ttcttcttta tgggcgataa ggtgaagcgc gatcgcttcg tcggctcggt gaaggagttc   900
ctgcaaacct ggaagttctt tgatggcgta gatatcgact gggaattccc gggcgggcag   960
ggtgctaacc gaaactggg  cagtacgcag gatgggcaa  cctatgtgca gctgatgaaa  1020
gagctgcgcg ccatgctgga tcagctttcg gcggaaacgg gccgtaagta tgaactgacc  1080
tctgcgatca gcgccggcaa ggataaaatc gataaggtgg attacaacac cgcacaaaac  1140
tcgatggatc acatttttcct gatgagttac gacttctatg gggcattcga tctgaaaaat  1200
ctgggccacc agactgcgct gaaagcgccg gcctggaaac cggatacggc gtataccacg  1260
gtgaatggcg ttaatgcact gctcacgcag ggcgtgaagc cgggcaaaat cgtggtgggc  1320
accgccatgt acgtcgcgg  ttggaccggg gtgaacggtt accagaacaa cattccgttt  1380
accggcaccg ccactggccc ggtgaaaggc acctgggaaa atggcatcgt ggattaccgc  1440
cagatcgcca tgagtttat  gagcggcgaa tggcagtaca gctacgatgc taccgctgaa  1500
gcaccctatg tcttcaaacc ttccactggc gatctgatca ccttcgacga tgcgcgctcg  1560
gtgcaggcga gggcaaata  tgtgctggat aagcagctgg gcgggttgtt ctcatgggaa  1620
attgacgccg acaacggcga tattctgaat aacatgaaca gcagcctggg caacagcgtc  1680
ggtacgcctt aa                                                      1692
```

<210> SEQ ID NO 2
<211> LENGTH: 1692
<212> TYPE: DNA
<213> ORGANISM: Serratia marcescens

<400> SEQUENCE: 2

```
atgcgcaaat ttaataaacc gctgttggcg ctgttgatcg cagcacgct  gtgttccgcg    60
gcgcaggccg ccgcgccggg caagccgacc atcgcctggg caacaccaa  gttcgccatc   120
gttgaagttg accaggcggc taccgcttat aataatttgg tgaaggtaaa aaatgccgcc   180
gatgtttccg tctcctggaa tttatggaat ggcgacgcgg gcacgacggc caagatttta   240
ttaaatggta agaggcgtg  gagtggtcct tcaaccggat cttccggtac ggcgaatttt   300
aaagtgaata aggcggccg  ttatcaaatg caggtggcat tgtgcaatgc cgacggctgc   360
```

-continued

```
accgccagtg acgccaccga aattgtggtg gccgacaccg acggcagcca tttggcgccg    420
ttgaaagagc cgctgctgga aaagaataaa ccgtataaac agaactccgg caaagtggtc    480
ggttcttatt tcgtcgagtg gggcgtttac gggcgcaatt tcaccgtcga caagatcccg    540
gcgcaaaacc tgacccacct gctgtacggc tttatcccga tctgcggcgg caatggcatc    600
aacgacagcc tgaaagagat tgaaggcagc ttccaggcgt tacagcgctc ctgccagggc    660
cgcgaggact tcaaagtctc ggtccacgat ccgttcgccg cgctgcaaaa agcgcagaag    720
ggcgtgaccg cctgggatga ccctacaag ggcaacttcg ccagctgat ggcgctgaag     780
caggcgcatc ctgacctgaa atcctgccg tcgatcggcg gctggacgct gtccgacccg     840
ttcttcttca tgggcgacaa ggtgaagcgc gatcgcttcg tcggttcggt gaaagagttc    900
ctgcagacct ggaagttctt cgacggcgtg gatatcgact gggagttccc gggcggcaaa    960
ggcgccaacc ctaacctggg cagcccgcaa gacgggaaa cctatgtgtt gctgatgaag   1020
gagctgcggg cgatgctgga tcagctgtcg gcggaaaccg gccgcaagta tgagctgacc   1080
tccgccatca gcgccggtaa ggacaagatc gacaaggtgg cttacaacgt tgcgcagaac   1140
tcgatggatc acatcttcct gatgagctac gacttctatg gcgccttcga tctgaagaac   1200
ctggggcatc agaccgcgct gaatgcgccg gcctggaagc cggacaccgc ttacaccacg   1260
gtgaacggcg tcaatgcgct gctggcgcag gcgtcaagc cgggcaagat cgtggtcggc   1320
accgccatgt atggccgcgg ctggaccggg gtgaacggct accagaacaa cattccgttc   1380
accggtaccc ccactgggcc ggttaaaggc acctgggaga acggcatcgt ggactaccgc   1440
caaatcgccg ccagttcat gagcggcgag tggcagtata cctacgacgc cacggcggaa   1500
gcgccttacg tgttcaaacc ttccaccggc gatctgatca ccttcgacga tgcccgctcg   1560
gtgcaggcca aaggcaagta cgtgctggat aagcagctgg gcggcctgtt ctcctgggag   1620
atcgacgcgg ataacggcga tattctcaac agcatgaacg ccagcctggg caacagcgcc   1680
ggcgttcaat aa                                                      1692
```

<210> SEQ ID NO 3
<211> LENGTH: 1692
<212> TYPE: DNA
<213> ORGANISM: Artificial Sequence
<220> FEATURE:
<223> OTHER INFORMATION: Chitinase recombinant DNA 1

<400> SEQUENCE: 3

```
atgcgcaaat taataaaacc gctgttggcg ttgctgatcg gcagcacgct gtgctctgcg     60
gcgcaggccg ctgcaccggg caaacctacg ttggcctggg caataccaa attcgccatt    120
gtcgaagtcg atcaagcggc gacggcttat aataatctgg tgaaagtaaa aagtgccgcc    180
gacgtttctg tttcatggaa tttatggaat ggcgataccg gtaccacggc aaaagtatta    240
ttaaatggca agaagtttg gagtggtgcc tcaaccggta gttcgggaac cgcaaacttt    300
aaggtgaata aggcggccg ttatcaaatg caggtggcgt tatgcaacgc cgacggctgt    360
accgccagcg atgcaaccga aattgtggtg gcagataccg acggtagcca tttggcacct    420
ttaaagaaac ctttgttgga aaagaataag ccttataaac aagactccgg caaagtggtc    480
ggttcttatt tcgtcgagtg gggcgtttac gggcgcaatt tcaccgtcga caagatcccg    540
gctcagaacc tgacgcacct gctgtacggc tttatcccta tctgtggcgg tgacggcatc    600
aacgacagcc tgaaagagat cgaaggcagc ttccaggcgt tacagcgttc ctgtcagggg    660
```

```
cgtgaagact ttaaggtatc gatccacgat ccgttcgctg cgctgcagaa aggtcagaag    720
ggcgtgaccg cctgggacga ccctacaaa ggcaacttcg ccagttgat ggcgttgaaa    780 caggcgcgcc cggacctgaa atcctgccg tcgatcggtg gctggacgtt atccgatccg    840
ttcttcttta tgggcgataa ggtgaagcgc gatcgcttcg tcggctcggt gaaggagttc    900
ctgcaaacct ggaagttctt tgatggcgta gatatcgact gggaattccc gggcggggcag    960 ggtgctaacc cgaaactggg cagtacgcag gatgggcaa cctatgtgca gctgatgaaa   1020
gagctgcgcg ccatgctgga tcagcttttcg gcggaaacgg ccgtaagta tgaactgacc   1080 tctgcgatca gcgccggcaa ggataaaatc gataaggtgg attacaacac cgcacaaaac   1140
tcgatggatc acattttcct gatgagttac gacttctatg gggcattcga tctgaaaaat   1200
ctgggccacc agactgcgct gaaagcgccg gcctggaaac cggatacggc gtataccacg   1260
gtgaatggcg ttaatgcact gctcacgcag ggcgtgaagc cgggcaaaat cgtggtgggc   1320
accgccatgt acgtcgcgg ttggaccggg gtgaacggtt accagaacaa cattccgttt   1380
accggcaccg ccactggccc ggtgaaaggc acctgggaaa atggcatcgt ggattaccgc   1440
cagatcgcca atgagtttat gagcggcgaa tggcagtaca gctacgatgc taccgctgaa   1500
gcaccctatg tcttcaaacc ttccactggc gatctgatca ccttcgacga tgcgcgctcg   1560
gtgcaggcga agggcaaata tgtgctggat aagcagctgg gcgggttgtt ctcatgggaa   1620
attgacgccg acaacggcga tattctgaat aacatgaaca gcagcctggg caacagcgtc   1680
ggtacgcctt aa                                                      1692
```

<210> SEQ ID NO 4
<211> LENGTH: 1692
<212> TYPE: DNA
<213> ORGANISM: Artificial Sequence
<220> FEATURE:
<223> OTHER INFORMATION: Chitinase recombinant DNA 2

<400> SEQUENCE: 4

```
atgcgcaaat ttaataaacc gctgttggcg ttgctgatcg gcagcacgct gtgctctgcg     60
gcgcaggccg ctgcaccggg caaacctacg ttggcctggg gcaataccaa attcgccatt    120
gtcgaagtcg atcaagcggc gacggcttat aataatctgg tgaaagtaaa aagtgccgcc    180
gacgtttctg tttcatggaa tttatggaat ggcgataccg gtaccacggc aaaagtatta    240
ttaaatggca agaagttttg gagtggtgcc tcaaccggta gttcgggaac cgcaaaacttt    300 aaggtgaata aggcggccg ttatcaaatg caggtggcgt tatgcaacgc cgacggctgt    360
accgccagcg atgcaaccga aattgtggtg gcagataccg acgtagcca tttggcacct    420 ttaaaagaac ctttgttgga aaagaataag ccttataaac aagactccgg caaagtggtt    480
ggctcttatt tcgttgaatg gggcgtttac ggccgtaatt tcaccgtcga taaacttccg    540
gctcagaacc tgacgcacct gctgtacggc tttatcccta tctgtggcgg tgacggcatc    600
aacgacagcc tgaaagagat cgaaggcagc ttccaggcgt tacagcgttc ctgtcagggg    660
cgtgaagact ttaaggtatc gatccacgat ccgttcgctg cgctgcagaa aggtcagaag    720
ggcgtgaccg cctgggacga ccctacaaa ggcaacttcg ccagttgat ggcgttgaaa    780 caggcgcgcc cggacctgaa atcctgccg tcgatcggtg gctggacgtt atccgatccg    840
ttcttcttta tgggcgataa ggtgaagcgc gatcgcttcg tcggctcggt gaagagttc    900 ctgcagacct ggaagttctt cgacggcgtg gatatcgact gggagttccc gggcggcaaa    960
ggcgccaacc ctaacctggg cagcccgcaa gacggggaaa cctatgtgtt gctgatgaag   1020
```

-continued

```
gagctgcggg cgatgctgga tcagctgtcg gcggaaaccg gccgcaagta tgagctgacc    1080
tccgccatca gcgccggtaa ggacaagatc gacaaggtgg cttacaacgt tgcgcagaac    1140
tcgatggatc acatcttcct gatgagctac gacttctatg cgccttcga tctgaagaac    1200 ctggggcatc agaccgcgct gaatgcgccg gcctggaagc cggacaccgc ttacaccacg    1260
gtgaacggcg tcaatgcgct gctggcgcag ggcgtcaagc cgggcaagat cgtggtcggc    1320
accgccatgt atggccgcgg ctggaccggg gtgaacggct accagaacaa cattccgttc    1380
accggtaccg ccactgggcc ggttaaaggc acctgggaga acggcatcgt ggactaccgc    1440
cagatcgcca atgagtttat gagcggcgaa tggcagtaca gctacgatgc taccgctgaa    1500
gcaccctatg tcttcaaacc ttccactggc gatctgatca ccttcgacga tgcgcgctcg    1560
gtgcaggcga agggcaaata tgtgctggat aagcagctgg cggggttgtt ctcatgggaa    1620
attgacgccg acaacggcga tattctgaat aacatgaaca gcagcctggg caacagcgtc    1680
ggtacgcctt aa                                                         1692

<210> SEQ ID NO 5
<211> LENGTH: 1692
<212> TYPE: DNA
<213> ORGANISM: Artificial Sequence
<220> FEATURE:
<223> OTHER INFORMATION: Chitinase recombinant DNA 3

<400> SEQUENCE: 5
atgcgcaaat ttaataaacc gctgttggcg ctgttgatcg cagcacgct gtgttccgcg      60 gcgcaggccg ccgcgccggg caagccgacc atcgcctggg caacaccaa gttcgccatc      120 gttgaagttg accaggcggc taccgcttat aataatttgg tgaaggtaaa aaatgccgcc    180
gatgtttccg tctcctggaa tttatggaat ggcgacgcgg gcacgacggc caagatttta    240
ttaaatggta agaggcgtg gagtggtcct caaccggat cttccggtac ggcgaatttt      300
aaagtgaata aaggcggccg ttatcaaatg caggtggcat tgtgcaatgc cgacggctgc    360
accgccagtg acgccaccga aattgtggtg gccgacaccg acggcagcca tttggcgccg    420
ttgaaagagc cgctgctgga aaagaataaa ccgtataaac agaactccgg caaagtggtc    480
ggttcttatt tcgtcgagtg gggcgtttac gggcgcaatt tcaccgtcga caagatcccg    540
gcgcaaaacc tgacccacct gctgtacggc tttatcccga tctgcggcgg caatggcatc    600
aacgacagcc tgaaagagat tgaaggcagc ttccaggcgt tacagcgctc ctgccagggc    660
cgcgaggact tcaaagtctc ggtccacgat ccgttcgccg cgctgcaaaa agcgcagaag    720
ggcgtgaccg cctgggatga cccctacaag ggcaacttcg ccagctgat ggcgctgaag      780 caggcgcatc ctgacctgaa aatcctgccg tcgatcggcg gctggacgtt atccgatccg    840 ttcttctttta tgggcgataa ggtgaagcgc gatcgcttcg tcggctcggt gaaggagttc    900
ctgcaaacct ggaagttctt tgatggcgta gatatcgact gggaattccc gggcgggcag    960
ggtgctaacc cgaaactggg cagtacgcag gatgggggcaa cctatgtgca gctgatgaaa    1020
gagctgcgcg ccatgctgga tcagctttcg gcggaaacgg gccgtaagta tgaactgacc    1080
tctgcgatca gcgccggcaa ggataaaatc gataaggtgg attacaacac cgcacaaaac    1140
tcgatggatc acatttttcct gatgagttac gacttctatg gggcattcga tctgaaaaat    1200
ctgggccacc agactgcgct gaaagcgccg gcctggaaac cggatacggc gtataccacg    1260
gtgaatggcg ttaatgcact gctcacgcag ggcgtgaagc cgggcaaaat cgtggtgggc    1320
```

```
accgccatgt acggtcgcgg ttggaccggg gtgaacggtt accagaacaa cattccgttt    1380
accggcaccg ccactggccc ggtgaaaggc acctgggaaa atggcatcgt ggattaccgc    1440
cagatcgcca atgagtttat gagcggcgaa tggcagtaca gctacgatgc taccgctgaa    1500
gcaccctatg tcttcaaacc ttccactggc gatctgatca ccttcgacga tgcgcgctcg    1560
gtgcaggcga agggcaaata tgtgctggat aagcagctgg gcgggttgtt ctcatgggaa    1620
attgacgccg acaacggcga tattctgaat aacatgaaca gcagcctggg caacagcgtc    1680
ggtacgcctt aa                                                         1692

<210> SEQ ID NO 6
<211> LENGTH: 1692
<212> TYPE: DNA
<213> ORGANISM: Artificial Sequence
<220> FEATURE:
<223> OTHER INFORMATION: Chitinase recombinant DNA 4

<400> SEQUENCE: 6
atgcgcaaat ttaataaacc gctgttggcg ctgttgatcg gcagcacgct gtgttccgcg     60
gcgcaggccg ccgcgccggg caagccgacc atcgcctggg caacaccaa gttcgccatc     120 gttgaagttg accaggcggc taccgcttat aataatttgg tgaaggtaaa aaatgccgcc    180
gatgtttccg tctcctggaa tttatggaat ggcgacgcgg gcacgacggc caagatttta    240
ttaaatggta agaggcgtg gagtggtcct tcaaccggat cttccggtac ggcgaatttt    300
aaagtgaata aaggcggccg ttatcaaatg caggtggcat tgtgcaatgc cgacggctgc    360
accgccagtg acgccaccga aattgtggtg ccgacaccg acggcagcca tttggcgccg    420
ttgaaagagc cgctgctgga aaagaataaa ccgtataaac agaactccgg caaagtggtc    480
ggttcttatt tcgtcgagtg gggcgtttac gggcgcaatt tcaccgtcga caagatcccg    540
gcgcaaaacc tgacccacct gctgtacggc tttatcccta tctgtggcgg tgacggcatc    600
aacgacagcc tgaaagagat cgaaggcagc ttccaggcgt acagcgttc ctgtcagggg    660 cgtgaagact ttaaggtatc gatccacgat ccgttcgctg cgctgcagaa aggtcagaag    720
ggcgtgaccg cctgggacga ccctacaaa ggcaacttcg ccagttgat ggcgttgaaa    780 caggcgcgcc cggacctgaa aatcctgccg tcgatcggtg gctggacgtt atccgatccg    840 ttcttctttta tgggcgataa ggtgaagcgc gatcgcttcg tcggctcggt gaaggagttc    900
ctgcaaacct ggaagttctt tgatggcgta gatatcgact gggaattccc gggcgggcag    960 gtgctaacc cgaaactggg cagtacgcag gatggggcaa cctatgtgca gctgatgaaa    1020
gagctgcgcg ccatgctgga tcagctttcg gcggaaacgg ccgtaagta tgaactgacc    1080 tctgcgatca gcgccggcaa ggataaaatc gataaggtgg attacaacac cgcacaaaac    1140
tcgatggatc acatttttcct gatgagttac gacttctatg gggcattcga tctgaaaaat    1200
ctgggccacc agactgcgct gaaagcgccg gcctggaaac cggatacggc gtataccacg    1260
gtgaatggcg ttaatgcact gctcacgcag gcgtgaagc cgggcaaaat cgtggtgggc    1320
accgccatgt acggtcgcgg ttggaccggg gtgaacggtt accagaacaa cattccgttt    1380
accggcaccg ccactggccc ggtgaaaggc acctgggaaa atggcatcgt ggattaccgc    1440
cagatcgcca atgagtttat gagcggcgaa tggcagtaca gctacgatgc taccgctgaa    1500
gcaccctatg tcttcaaacc ttccactggc gatctgatca ccttcgacga tgcgcgctcg    1560
gtgcaggcga agggcaaata tgtgctggat aagcagctgg gcgggttgtt ctcatgggaa    1620
attgacgccg acaacggcga tattctgaat aacatgaaca gcagcctggg caacagcgtc    1680
```
ggtacgcctt aa                                                         1692

<210> SEQ ID NO 7
<211> LENGTH: 1692
<212> TYPE: DNA
<213> ORGANISM: Artificial Sequence
<220> FEATURE:
<223> OTHER INFORMATION: Chitinase recombinant DNA 5

<400> SEQUENCE: 7

| | | | | | |
|---|---|---|---|---|---|
| atgcgcaaat | ttaataaacc | gctgttggcg | ctgttgatcg | cagcacgct | gtgttccgcg | 60 |
| gcgcaggccg | ccgcgccggg | caagccgacc | atcgcctggg | caacaccaa | gttcgccatc | 120 |
| gttgaagttg | accaggcggc | taccgcttat | aataatttgg | tgaaggtaaa | aaatgccgcc | 180 |
| gatgtttccg | tctcctggaa | tttatggaat | ggcgacgcgg | gcacgacggc | caagatttta | 240 |
| ttaaatggta | agaggcgtg | gagtggtcct | tcaaccggat | cttccggtac | ggcgaatttt | 300 |
| aaagtgaata | aggcggccg | ttatcaaatg | caggtggcat | tgtgcaatgc | cgacggctgc | 360 |
| accgccagtg | acgccaccga | aattgtggtg | gccgacaccg | acggcagcca | tttggcgccg | 420 |
| ttgaaagagc | cgctgctgga | aaagaataaa | ccgtataaac | agaactccgg | caaagtggtc | 480 |
| ggttcttatt | tcgtcgagtg | gggcgtttac | ggccgtaatt | tcaccgtcga | taaacttccg | 540 |
| gctcagaacc | tgacgcacct | gctgtacggc | tttatcccta | tctgtggcgg | tgacggcatc | 600 |
| aacgacagcc | tgaaagagat | cgaaggcagc | ttccaggcgt | tacagcgttc | ctgtcagggg | 660 |
| cgtgaagact | ttaaggtatc | gatccacgat | ccgttcgctg | cgctgcagaa | aggtcagaag | 720 |
| ggcgtgaccg | cctgggacga | cccctacaaa | ggcaacttcg | ccagttgat | ggcgttgaaa | 780 |
| caggcgcgcc | cggacctgaa | aatcctgccg | tcgatcggtg | gctggacgtt | atccgatccg | 840 |
| ttcttcttta | tgggcgataa | ggtgaagcgc | gatcgcttcg | tcggctcggt | gaaagagttc | 900 |
| ctgcagacct | ggaagttctt | cgacggcgtg | gatatcgact | gggagttccc | gggcggcaaa | 960 |
| ggcgccaacc | ctaacctggg | cagcccgcaa | gacggggaaa | cctatgtgtt | gctgatgaag | 1020 |
| gagctgcggg | cgatgctgga | tcagctgtcg | gcggaaaccg | gccgcaagta | tgagctgacc | 1080 |
| tccgccatca | gcgccggtaa | ggacaagatc | gacaaggtgg | cttacaacgt | tgcgcagaac | 1140 |
| tcgatggatc | acatcttcct | gatgagctac | gacttctatg | gcgccttcga | tctgaagaac | 1200 |
| ctggggcatc | agaccgcgct | gaaagcgccg | gcctggaaac | cggatacggc | gtataccacg | 1260 |
| gtgaatggcg | ttaatgcact | gctcacgcag | ggcgtgaagc | cgggcaaaat | cgtggtgggc | 1320 |
| accgccatgt | acggtcgcgg | ttggaccggg | gtgaacggtt | accagaacaa | cattccgttt | 1380 |
| accggcaccg | ccactggccc | ggtgaaaggc | acctgggaaa | atggcatcgt | ggattaccgc | 1440 |
| cagatcgcca | atgagtttat | gagcggcgaa | tggcagtaca | gctacgatgc | taccgctgaa | 1500 |
| gcaccctatg | tcttcaaacc | ttccactggc | gatctgatca | ccttcgacga | tgcccgctcg | 1560 |
| gtgcaggcca | aaggcaagta | cgtgctggat | aagcagctgg | gcggcctgtt | ctcctgggag | 1620 |
| atcgacgcgg | ataacggcga | tattctcaac | agcatgaacg | ccagcctggg | caacagcgcc | 1680 |
| ggcgttcaat | aa | | | | | 1692 |

<210> SEQ ID NO 8
<211> LENGTH: 1692
<212> TYPE: DNA
<213> ORGANISM: Artificial Sequence
<220> FEATURE:
<223> OTHER INFORMATION: Chitinase recombinant DNA 6

-continued

<400> SEQUENCE: 8

```
atgcgcaaat ttaataaacc gctgttggcg ctgttgatcg gcagcacgct gtgttccgcg      60
gcgcaggccg ccgcgccggg caagccgacc atcgcctggg caacaccaa gttcgccatc     120
gttgaagttg accaggcggc taccgcttat aataatttgg tgaaggtaaa aaatgccgcc    180
gatgtttccg tctcctggaa tttatggaat ggcgacgcgg gcacgacggc caagatttta    240
ttaaatggta aagaggcgtg gagtggtcct tcaaccggat cttccggtac ggcgaatttt    300
aaagtgaata aaggcggccg ttatcaaatg caggtggcat tgtgcaatgc cgacggctgc    360
accgccagtg acgccaccga aattgtggtg gcagataccg acggtagcca tttggcacct    420
ttaaaagaac ctttgttgga aagaataag ccttataaac aagactccgg caaagtggtt     480
ggctcttatt tcgttgaatg gggcgtttac ggccgtaatt tcaccgtcga taaacttccg    540
gctcagaacc tgacgcacct gctgtacggc tttatcccta tctgtggcgg tgacggcatc    600
aacgacagcc tgaaagagat tgaaggcagc ttccaggcgt tacagcgttc ctgtcagggg    660
cgtgaagact ttaaggtatc gatccacgat ccgttcgctg cgctgcagaa aggtcagaag    720
ggcgtgaccg cctgggacga ccctacaaa ggcaacttcg ccagttgat ggcgttgaaa      780
caggcgcgcc cggacctgaa atcctgccg tcgatcggtg gctggacgtt atccgatccg     840
ttcttcttta tgggcgacaa ggtgaagcgc gatcgcttcg tcggttcggt gaaagagttc    900
ctgcagacct ggaagttctt cgacggcgtg gatatcgact gggagttccc gggcggcaaa    960
ggcgccaacc ctaacctggg cagcccgcaa gacggggaaa cctatgtgtt gctgatgaag   1020
gagctgcggg cgatgctgga tcagctgtcg gcggaaaccg gccgcaagta tgagctgacc   1080
tccgccatca gcgccggtaa ggataaaatc gataaggtgg attacaacac cgcacaaaac   1140
tcgatggatc acatttttcct gatgagttac gacttctatg gggcattcga tctgaaaaat   1200
ctgggccacc agactgcgct gaaagcgccg gcctggaaac cggatacggc gtataccacg   1260
gtgaatggcg ttaatgcact gctcacgcag ggcgtgaagc cgggcaaaat cgtggtgggc   1320
accgccatgt acgtcgcgg ttggaccggg gtgaacggtt accagaacaa cattccgttt    1380
accggcaccg ccactggccc ggtgaaaggc acctgggaaa atggcatcgt ggattaccgc   1440
cagatcgcca tgagtttat gagcggcgaa tggcagtaca gctacgatgc taccgctgaa   1500
gcaccctatg tcttcaaacc ttccactggc gatctgatca ccttcgacga tgcgcgctcg   1560
gtgcaggcga agggcaaata tgtgctggat aagcagctgg gcgggttgtt ctcatgggaa   1620
attgacgccg acaacggcga tattctgaat aacatgaaca gcagcctggg caacagcgtc   1680
ggtacgcctt aa                                                       1692
```

<210> SEQ ID NO 9
<211> LENGTH: 1692
<212> TYPE: DNA
<213> ORGANISM: Artificial Sequence
<220> FEATURE:
<223> OTHER INFORMATION: Chitinase recombinant DNA 7

<400> SEQUENCE: 9

```
atgcgcaaat ttaataaacc gctgttggcg ttgctgatcg gcagcacgct gtgctctgcg      60
gcgcaggccg ctgcaccggg caaacctacg ttggcctggg caataccaa attcgccatt     120
gtcgaagtcg atcaagcggc gacggcttat aataatctgg tgaaagtaaa aagtgccgcc    180
gacgtttctg tttcatggaa tttatggaat ggcgataccg gtaccacggc aaaagtatta    240
ttaaatggca aagaagtttg gagtggtgcc tcaaccggta gttcgggaac cgcaaacttt    300
```

-continued

```
aaggtgaata aaggcggccg ttatcaaatg caggtggcgt tatgcaacgc cgacggctgt      360
accgccagcg atgcaaccga aattgtggtg gcagataccg acggtagcca tttggcacct      420
ttaaaagaac ctttgttgga aaagaataag ccttataaac aagactccgg caaagtggtt      480
ggctcttatt tcgttgaatg gggcgtttac ggccgtaatt tcaccgtcga taaacttccg      540
gctcagaacc tgacgcacct gctgtacggc tttatcccta tctgtggcgg tgacggcatc      600
aacgacagcc tgaaagagat cgaaggcagc ttccaggcgt tacagcgttc ctgtcagggg      660
cgtgaagact ttaaggtatc gatccacgat ccgttcgccg cgctgcaaaa agcgcagaag      720
ggcgtgaccg cctgggatga cccctacaag ggcaacttcg gccagctgat ggcgctgaag      780
caggcgcatc ctgacctgaa aatcctgccg tcgatcggcg gctggacgct gtccgacccg      840
ttcttcttca tgggcgacaa ggtgaagcgc gatcgcttcg tcggttcggt gaaagagttc      900
ctgcagacct ggaagttctt cgacggcgtg gatatcgact gggagttccc gggcggccaa      960
ggcgccaacc ctaacctggg cagcccgcaa gacggggaaa cctatgtgtt gctgatgaag     1020
gagctgcggg cgatgctgga tcagctgtcg gcggaaaccg gccgcaagta tgagctgacc     1080
tccgcgatca gcgccggcaa ggataaaatc gataaggtgg attacaacac cgcacaaaac     1140
tcgatggatc acattttcct gatgagttac gacttctatg gggcattcga tctgaaaaat     1200
ctgggccacc agactgcgct gaaagcgccg gcctggaaac cggatacggc gtataccacg     1260
gtgaatggcg ttaatgcact gctcgcgcag ggcgtgaagc cgggcaaaat cgtggtgggc     1320
accgccatgt acgtcgcgg ttggaccggg gtgaacggtt accagaacaa cattccgttt     1380
accggcaccg ccactggccc ggtgaaaggc acctgggaaa atggcatcgt ggattaccgc     1440
cagatcgcca atgagtttat gagcggcgaa tggcagtaca gctacgatgc taccgctgaa     1500
gcaccctatg tcttcaaacc ttccactggc gatctgatca ccttcgacga tgcgcgctcg     1560
gtgcaggcga agggcaaata tgtgctggat aagcagctgg gcgggttgtt ctcatgggaa     1620
attgacgccg acaacggcga tattctgaat aacatgaaca gcagcctggg caacagcgtc     1680
ggtacgcctt aa                                                        1692
```

<210> SEQ ID NO 10
<211> LENGTH: 1692
<212> TYPE: DNA
<213> ORGANISM: Artificial Sequence
<220> FEATURE:
<223> OTHER INFORMATION: Chitinase recombinant DNA 8

<400> SEQUENCE: 10

```
atgcgcaaat ttaataaacc gctgttggcg ctgttgatcg cagcacgct gtgttccgcg        60 gcgcaggccg ccgcgccggg caagccgacc atcgcctggg gcaacaccaa gttcgccatc      120
gttgaagttg accaggcggc taccgcttat aataatttgg tgaaggtaaa aaatgccgcc      180
gatgtttccg tctcctggaa tttatggaat ggcgacgcgg gcacgacggc caagatttta      240
ttaaatggta agaggcgtg gagtggtcct tcaaccggat cttccggtac ggcgaatttt      300
aaagtgaata aaggcggccg ttatcaaatg caggtggcgt tatgcaacgc cgacggctgt      360
accgccagcg atgcaaccga aattgtggtg gccgacaccg acggcagcca tttggcgccg      420
ttgaaagagc cgctgctgga aaagaataaa ccgtataaac agaactccgg caaagtggtc      480
ggttcttatt tcgtcgagtg gggcgtttac gggcgcaatt tcaccgtcga caagatcccg      540
gcgcaaaacc tgacccacct gctgtacggc tttatcccga tctgcggcgg caatggcatc      600
```

```
aacgacagcc tgaaagagat tgaaggcagc ttccaggcgt tacagcgctc ctgccagggc     660
cgcgaggact tcaaagtctc ggtccacgat ccgttcgccg cgctgcaaaa agcgcagaag     720
ggcgtgaccg cctgggatga cccctacaag ggcaacttcg ccagctgat ggcgctgaag      780 caggcgcatc ctgacctgaa aatcctgccg tcgatcggcg gctggacgct gtccgacccg    840
ttcttcttaa tgggcgacaa ggtgaagcgc gatcgcttcg tcggttcggt gaaagagttc     900
ctgcagacct ggaagttctt cgacggcgtg gatatcgact gggagttccc gggcggcaaa     960
ggcgccaacc ctaacctggg cagcccgcaa gacggggaaa cctatgtgtt gctgatgaag    1020
gagctgcggg cgatgctgga tcagctgtcg gcggaaaccg gccgcaagta tgagctgacc    1080
tccgccatca gcgccggtaa ggacaagatc gacaaggtgg cttacaacgt tgcgcagaac    1140
tcgatggatc acatcttcct gatgagctac gacttctatg cgccttcga tctgaagaac     1200 ctggggcatc agaccgcgct gaatgcgccg gcctggaagc cggacaccgc ttacaccacg    1260
gtgaacggcg tcaatgcgct gctggcgcag ggcgtcaagc cgggcaagat cgtggtcggc    1320
accgccatgt atggccgcgg ctggaccggg gtgaacggct accagaacaa cattccgttc    1380
accggtaccg ccactgggcc ggttaaaggc acctgggaga acggcatcgt ggactaccgc    1440
caaatcgccg gccagttcat gagcggcgag tggcagtata cctacgacgc cacggcggaa    1500
gcgccttacg tgttcaaacc ttccaccggc gatctgatca ccttcgacga tgcccgctcg    1560
gtgcaggcca aaggcaagta cgtgctggat aagcagctgg gcggcctgtt ctcctgggag    1620
atcgacgcgg ataacggcga tattctcaac agcatgaacg ccagcctggg caacagcgcc    1680
ggcgttcaat aa                                                          1692

<210> SEQ ID NO 11
<211> LENGTH: 1692
<212> TYPE: DNA
<213> ORGANISM: Artificial Sequence
<220> FEATURE:
<223> OTHER INFORMATION: Chitinase recombinant DNA 9

<400> SEQUENCE: 11
atgcgcaaat taataaaacc gctgttggcg ctgttgatcg gcagcacgct gtgttccgcg     60
gcgcaggccg ccgcgccggg caagccgacc atcgcctggg gcaacaccaa gttcgccatc    120
gttgaagttg atcaagcggc gacggcttat aataatctgg tgaaagtaaa aagtgccgcc    180
gacgtttctg tttcatggaa tttatggaat ggcgataccg gtaccacggc aaaagtatta    240
ttaaatggca aagaagttta gagtggtgcc tcaaccggta gttcgggaac cgcaaacttt    300
aaggtgaata aggcggccg ttatcaaatg caggtggcgt tatgcaacgc cgacggctgt     360
accgccagcg atgcaaccga aattgtggtg gcagataccg acggtagcca tttggcacct    420
ttaaaagaac ctttgttgga aaagaataag ccttataaac aagactccgg caaagtggtt    480
ggctcttatt tcgttgaatg gggcgtttac ggccgtaatt tcaccgtcga taacttccg      540 gctcagaacc tgacgcacct gctgtacggc tttatcccta tctgtggcgg tgacggcatc    600
aacgacagcc tgaaagagat cgaaggcagc ttccaggcgt tacagcgttc ctgtcagggg    660
cgtgaagact ttaaggtatc gatccacgat ccgttcgctg cgctgccgaa aggtcagaag    720
ggcgtgaccg cctgggacga cccctacaaa ggcaacttcg ccagttgat ggcgttgaaa     780 caggcgcgcc cggacctgaa aatcctgccg tcgatcggtg gctggacgtt atccgatccg    840
ttcttcttta tgggcgataa ggtgaagcgc gatcgcttcg tcggctcggt gaaggagttc    900
ctgcaaacct ggaagttctt tgatggcgta gatatcgact gggaattccc gggcgggcag    960
```

-continued

```
ggtgctaacc cgaaactggg cagtacgcag gatggggcaa cctatgtgca gctgatgaaa     1020
gagctgcgcg ccatgctgga tcagctttcg gcggaaacgg ccgtaagta tgaactgacc     1080 tctgcgatca gcgccggcaa ggataaaatc gataaggtgg attacaacac cgcacaaaac     1140
tcgatggatc acatttttcct gatgagttac gacttctatg gggccttcga tctgaagaac    1200
ctggggcatc agaccgcgct gaatgcgccg gcctggaagc cggacaccgc ttacaccacg     1260
gtgaacggcg tcaatgcgct gctggcgcag gcgtcaagc cgggcaaaat cgtggtgggc      1320
accgccatgt acggtcgcgg ttggaccggg gtgaacggtt accagaacaa cattccgttt     1380
accggcaccg ccactggccc ggtgaaaggc acctgggaaa atggcatcgt ggattaccgc     1440
cagatcgcca atgagtttat gagcggcgaa tggcagtaca gctacgatgc taccgctgaa     1500
gcaccctatg tcttcaaacc ttccactggc gatctgatca ccttcgacga tgcgcgctcg    1560
gtgcaggcga agggcaaata tgtgctggat aagcagctgg gcgggttgtt ctcatgggaa    1620
attgacgccg acaacggcga tattctgaat aacatgaaca gcagcctggg caacagcgtc    1680
ggtacgcctt aa                                                         1692
```

<210> SEQ ID NO 12
<211> LENGTH: 1692
<212> TYPE: DNA
<213> ORGANISM: Artificial Sequence
<220> FEATURE:
<223> OTHER INFORMATION: Chitinase recombinant DNA 10

<400> SEQUENCE: 12

```
atgcgcaaat ttaataaacc gctgttggcg ctgttgatcg gcagcacgct gtgttccgcg     60
gcgcaggccg ccgcgccggg caagccgacc atcgcctggg gcaacaccaa gttcgccatc    120
gttgaagttg accaggcggc taccgcttat aataatttgg tgaaggtaaa aaatgccgcc    180
gatgtttccg tctcctggaa tttatggaat ggcgacgcgg gcacgacggc caagatttta    240
ttaaatggta agaggcgtg gagtggtcct caaccggat cttccggtac ggcgaatttt      300
aaagtgaata aaggcggccg ttatcaaatg caggtggcat tgtgcaatgc cgacggctgc    360
accgccagtg acgccaccga aattgtggtg ccgacaccg acggcagcca tttggcgccg    420
ttgaaagagc cgctgctgga aagaataaa ccgtataaac agaactccgg caaagtggtc     480
ggttcttatt tcgtcgagtg gggcgtttac gggcgcaatt tcaccgtcga caagatcccg    540
gcgcagaaac tgacgcacct gctgtacggc tttatcccga tctgcggcgg tgatggcatc    600
aacgacagcc tgaaagagat cgaaggcagc ttccaggcgt tacagcgctc ctgtcagggg    660
cgcgaagact tcaaggtatc ggtccacgat ccgttcgccg cgctgcagaa agggcagaag    720
ggcgtgaccg cctgggacga cccctacaag ggcaacttcg ccagctgat ggcgctgaag    780 caggcgcgcc cggacctgaa aatcctgccg tcgatcggtg ctggacgtt atccgatccg    840 ttcttctta tgggcgataa ggtgaagcgc gatcgcttcg tcggctcggt gaaggagttc    900
ctgcaaacct ggaagttctt tgatggcgta gatatcgact gggaattccc gggcgggcag    960
ggtgctaacc cgaaactggg cagtatgcag gatggggcaa cctatgtgca gctgatgaaa   1020
gagctgcgcg ccatgctgga tcagctttcg gcggaaacgg ccgtaagta tgaactgacc    1080 tctgcgatca gcgccggcaa ggataaaatc gataaggtgg attacaacac cgcacaaaac   1140
tcgatggatc acattttcct gatgagttac gacttctatg gggcattcga tctgaaaaat   1200
ctgggccacc agactgcgct gaaagcgccg gcctggaaac cggatacggc gtataccacg   1260
```

-continued

```
gtgaatggcg ttaatgcact gctcacgcag ggcgtgaagc cgggcaaaat cgtggtgggc    1320
accgccatgt acggtcgcgg ttggaccggg gtgaacggtt accagaacaa cattccgttt    1380
accggcaccg ccactggccc ggtgaaaggc acctgggaaa atggcatcgt ggattaccgc    1440
cagatcgcca atgagtttat gagcggcgaa tggcagtaca gctacgatgc taccgctgaa    1500
gcaccctatg tcttcaaacc ttccactggc gatctgatca ccttcgacga tgcgcgctcg    1560
gtgcaggcga agggcaaata tgtgctggat aagcagctgg gcgggttgtt ctcatgggaa    1620
attgacgccg acaacggcga tattctgaat aacatgaaca gcagcctggg caacagcgtc    1680
ggtacgcctt aa                                                        1692
```

<210> SEQ ID NO 13
<211> LENGTH: 1692
<212> TYPE: DNA
<213> ORGANISM: Artificial Sequence
<220> FEATURE:
<223> OTHER INFORMATION: R-24 chitinase gene

<400> SEQUENCE: 13

```
atgcgcaaat ttaataaacc gctgttggcg ttgctgatcg cagcacgct gtgctctgcg      60 gcgcaggccg ctgcaccggg caaacctacg ttggcctggg caataccaa attcgccatt     120 gtcgaagtcg atcaagcggc gacggcttat aataatctgg tgaaagtaaa aagtgccgcc    180
gacgtttctg tttcatggaa tttatggaat ggcgataccg gtaccacggc aaaagtatta    240
ttaaatggca agaagtttg gagtggtgcc tcaaccggta gttcgggaac cgcaaacttt    300
aaggtgaata aaggcggccg ttatcaaatg caggtggcgt tatgcaacgc cgacggctgt    360
accgccagcg atgcaaccga aattgtggtg gcagataccg acgtagcca tttggcacct    420 ttaaaagaac ctttgttgga aagaataag ccttataaac aagactccgg caaagtggtc    480
ggttcttatt tcgtcgagtg gggcgtttac ggccgtaatt tcaccgtcga taaacttccg    540
gctcagaacc tgacgcacct gctgtacggc tttatccta tctgtggcgg tgacggcatc    600
aacgacagcc tgaaagagat tgaaggcagc ttccaggcgt acagcgctc ctgccagggc    660 cgcgaggact tcaaagtctc ggtccacgat ccgttcgccg cgctgcaaaa agcgcagaag    720
ggcgtgaccg cctgggatga ccctacaag ggcaacttcg ccagctgat ggcgctgaag    780 caggcgcatc ctgacctgaa aatcctgccg tcgatcggcg gctggacgct gtccgacccg    840
ttcttcttca tgggcgacaa ggtgaagcgc gatcgcttcg tcggttcggt gaaagagttc    900
ctgcagacct ggaagttctt cgacggcgtg gatatcgact gggagttccc gggcggcaaa    960
ggcgccaacc ctaacctggg cagcccgcaa gacggggaaa cctatgtgtt gctgatgaag   1020
gagctgcggg cgatgctgga tcagctgtcg gcggaaaccg gccgcaagta tgagctgacc   1080
tccgccatca gcgccggtaa ggacaagatc gacaaggtgg cttacaacgt tgcgcagaac   1140
tcgatggatc acatcttcct gatgagctac gacttctatg gcgccttcga tctgaagaac   1200
ctggggcatc agaccgcgct gaatgcgccg gcctggaagc cggacaccgc ttacaccacg   1260
gtgaacggcg tcaatgcgct gctggcgcag ggcgtgaagc cgggcaaaat cgtggtgggc   1320
accgccatgt acggtcgcgg ttggaccggg gtgaacggtt accagaacaa cattccgttt   1380
accggcaccg ccactggccc ggtgaaaggc acctgggaaa atggcatcgt ggattaccgc   1440
cagatcgcca atgagtttat gagcggcgaa tggcagtaca gctacgatgc taccgctgaa   1500
gcaccctatg tcttcaaacc ttccactggc gatctgatca ccttcgacga tgcgcgctcg   1560
gtgcaggcga agggcaaata tgtgctggat aagcagctgg gcgggttgtt ctcatgggaa   1620
```

```
attgacgccg acaacggcga tattctgaat aacatgaaca gcagcctggg caacagcgtc    1680
ggtacgcctt aa                                                        1692

<210> SEQ ID NO 14
<211> LENGTH: 1362
<212> TYPE: DNA
<213> ORGANISM: Bacillus sp.

<400> SEQUENCE: 14
atgaatggaa aagaaaaat tttcacatgt atttctattg taggaatcgg actagctagt      60
ttttctaatt ctagtttcgc agcaagtgta acggacaatt cagtacaaaa ttctattccc    120
gtagttaatc aacaagtagc tgctgcaaag gaaatgaaac catttccgca gcaagttaat    180
tatgcaggtg ttataaaacc gaatcatgtt acacaggaaa gtttaaatgc ttctgtaaga    240
agttactacg ataattggaa aagaaatat ttgaaaaatg atttatcttc tttacctggt     300
ggttattatg taaaggaga gattacaggt gatgctgatg ggtttaagcc acttggaact    360
tcagaaggtc aagggtatgg gatgataatt acagtattaa tggctggtta tgattcgaat    420
gctcaaaaaa tctatgacgg tttatttaaa acagcaagaa cttttaaaag ttctcaaaat    480
cctaatttaa tgggatgggt tgtcgcagat agtaaaaaag cacaaggtca ttttgattct    540
gctactgatg gagatttaga tattgcgtat tctcttcttc ttgctcataa gcagtgggga    600
tctaatggaa cagtgaatta tttgaaagaa gcacaagaca tgattacaaa aggtattaaa    660
gctagtaatg ttacaaataa taaccgacta aatttaggcg attgggattc taaaagttca    720
cttgatacga gaccatctga ttggatgatg tcacacctta gagcatttta tgaatttaca    780
ggtgataaaa cttggcttac tgttattaat aatttgtacg atgtttatac gcaatttagt    840
aataagtact ctccaaatac aggacttatt tcagatttcg ttgtaaaaaa cccaccacaa    900
cccgcaccta aagacttctt agaggagtca gaatatacaa atgcatatta ttacaatgct    960
agtcgggtac cattgagaat tgtaatggac tatgcgatgt acggcgagaa aagaagtaaa   1020
gtcatttctg ataaagtttc ttcgtggatt caaaataaaa cgaatggaaa tccttctaaa   1080
attgtggatg gttatcaatt aaatggatct aatattggta gttattcaac tgctgtatt t  1140 gtttcaccgt ttattgctgc aagtataaca agtagcaata atcaaaagtg ggtaaatagc   1200
ggttgggatt ggatgaagaa taagagagaa agttatttta gtgatagtta aatttatta   1260 actatgttat tcattacagg aaattggtgg aaacctgtac ctgatgatac aaaaatacaa   1320
aatcaaataa atgatgcaat ttatgaagga tacgataatt aa                      1362

<210> SEQ ID NO 15
<211> LENGTH: 1362
<212> TYPE: DNA
<213> ORGANISM: Artificial Sequence
<220> FEATURE:
<223> OTHER INFORMATION: M-13 mutant chitosanase gene

<400> SEQUENCE: 15
atgaatggaa aagaaaaaat tttcacatgt atttctattg taggaatcgg actagctagc     60
ttttctaatt ctagtttcgc agcaagtgta acggacaatt cagtacaaaa ttctattccc    120
gtagttaatc aacaagtagc tgctgcaaag gaaatgaaac catttccgca gcaagtttat    180
tatgcaggtg ttataaaacc gaatcatgtt acacaggaaa gtttaaatgc ttctgtaaga    240
agttactacg ataattggaa aagaaatat ttgaaaaatg atttatcttc tttacctggt     300
```

-continued

```
ggttattatg taaaaggaga tattacaggt gatgctgatg ggtttaagcc acttggaact    360
tcagaaggtc aagggtatgg gatgataatt acagtattaa tggctggtta tgattcgaat    420
gctcaaaaga tctatgacgg tttatttaaa acagcaagaa cttttaaaag ttctcgaaat    480
cctaatttaa tgggatgggt tgtcgcagat agtaaaaaag cacaaggtca ttttgattct    540
gctactgatg gagatttaga tattgcgtat tctcttcttc ttgctcataa gcagtgggga    600
tctaatggaa cagtgaatta tttgaaagaa gcacaagaca tgattacaaa aggtattaaa    660
gctagtaatg ttaccaataa tacccgacta aatttaggcg attgggattc taaaagttca    720
cttgatacga gaccatctga ttggatgatg tcacaccta gagcatttta tgaatttaca    780
ggtgataaaa cttggcttac tgttattaat aatttgtacg atgtttatac gcagtttagt    840
aataagtact ctccaaatac aggacttatt tcagatttcg ttgtaaaaaa cccaccacaa    900
cccgcaccta aaggcttctt agggagtca gaatatacaa atgcatatta ttacaatgct    960
agtcgggtac cattgagaat tgtaatggac tatgcgatgt acggcgagaa aagaagtaaa   1020
gtcatttctg ataaggtttc ttcgtggatt caaaataaaa cgaatggaaa tccttctaaa   1080
attgtggatg ttatcaatt agatggatct aatattggta gttatccaac tgctgtattt   1140
gtttcaccgc ttattgctgc aagtacaaca agtagcaata atcaaaagtg ggtaaatagc   1200
ggttgggatt ggatgaagaa taagagagaa agttatttta gtgatagtta taatttatta   1260
actatgttat tcattacagg gaattggtgg aaacccgtac ctggtgatac aaaaatacaa   1320
aatcaaataa atgatgctat ttatgaagga tacgataatt aa                      1362
```

<210> SEQ ID NO 16
<211> LENGTH: 1362
<212> TYPE: DNA
<213> ORGANISM: Artificial Sequence
<220> FEATURE:
<223> OTHER INFORMATION: M-20 mutant chitosanase gene

<400> SEQUENCE: 16

```
atgaatggaa aaagaaaaat tttcacgtgt atttctattg taggaatcgg actagctagt     60
ttttctaatc ctagtttcgc agcaagtgta acggacaatt cagtacaaaa ttctattccc    120
gtagttaatc aacaagtagc tgctgcaaag gaaatgaaac catttccgca gcaagttaat    180
tatgcaggtg ttataaaacc gaatcatgtt acacaggaaa gtttaaatgc ttctgtaaga    240
agttactacg ataattggaa aaagaaatat ttgaaaaatg atttatcttc tttacctggt    300
ggttattatg taaaaggaga tattacaggt gatgctgatg ggtttaagcc acttggaact    360
tcagaaggtc aagggtatgg gatgataatt acagtattaa tggctggtta tgattcgaat    420
gctcaaaaga tctatgacgg tttatttaaa acagcaagaa cttttaaaag ttctcgaaat    480
cctaatttaa tgggatgggt tgtcgcagat agtaaaaaag cacaaggtca ttttgattct    540
gctactgatg gagatttaga tattgcgtat tctcttcttc ttgctcataa gcagtgggga    600
tctaatggaa cagtgaatta tttgaaagaa gcacaagaca tgattacaaa aggtattaaa    660
gctagtaatg ttacaaataa tacccgacta aatttaggcg attgggattc taaaagttca    720
cttgatacga gaccatctga ttggatgatg tcacaccta gagcatttta tgagtttaca    780
ggtgataaaa cttggcttac tgttattaat aatttgtacg atgtttatac gcaatttagt    840
aataagtact ctccagatac aggacttatt tcagatttcg ttgtaaaaaa cccaccacaa    900
cccgcaccta aaggcttctt agggagtca gaatatacaa atgcatatta ttacaatgct    960
agtcgggtac cattgagaat tgtaatggac tatgcgatgt acggcgagaa aagaagtaaa   1020
```

```
gtcatttctg ataaggtttc ttcgtggatt caaaataaaa cgaatggaga tccttctaaa    1080
attgtggatg ttatcaatt agatggatct gatattggta gttattcaac tgctgtattt    1140
gtttcaccgt ttattgctgc aagtataaca agtagcaata atcaaaagtg ggtaaatagc    1200
ggttgggatt ggatgaagaa taagagagaa agttatttta gcgatagtta taatttgtta    1260
actatgttat tcattacggg aaattggtgg aaacctgtac ctgatgatac aaaaatacaa    1320
aatcaaataa atgatgcaat ttatgaagga tacgataatt aa                      1362

<210> SEQ ID NO 17
<211> LENGTH: 37
<212> TYPE: DNA
<213> ORGANISM: Artificial Sequence
<220> FEATURE:
<223> OTHER INFORMATION: Arbitrary polynucleotide

<400> SEQUENCE: 17
aggtccagtt agcattcgga aaggccgttt gagagag                              37

<210> SEQ ID NO 18
<211> LENGTH: 37
<212> TYPE: DNA
<213> ORGANISM: Artificial Sequence
<220> FEATURE:
<223> OTHER INFORMATION: Arbitrary polynucleotide

<400> SEQUENCE: 18
ctctctcaaa cggcctttcc gaatgctaac tggacct                              37

<210> SEQ ID NO 19
<211> LENGTH: 17
<212> TYPE: DNA
<213> ORGANISM: Artificial Sequence
<220> FEATURE:
<223> OTHER INFORMATION: unidirectional DNA fragment

<400> SEQUENCE: 19
gaatgctaac tggacct                                                    17

<210> SEQ ID NO 20
<211> LENGTH: 10
<212> TYPE: DNA
<213> ORGANISM: Artificial Sequence
<220> FEATURE:
<223> OTHER INFORMATION: Unidirectional DNA fragment

<400> SEQUENCE: 20
ctctctcaaa                                                            10

<210> SEQ ID NO 21
<211> LENGTH: 18
<212> TYPE: DNA
<213> ORGANISM: Artificial Sequence
<220> FEATURE:
<223> OTHER INFORMATION: Unidirectional DNA fragment

<400> SEQUENCE: 21
ctctctcaaa cggccttt                                                   18

<210> SEQ ID NO 22
<211> LENGTH: 20
<212> TYPE: DNA
<213> ORGANISM: Artificial Sequence
<220> FEATURE:
```

-continued

```
<223> OTHER INFORMATION: Unidirectional DNA fragment

<400> SEQUENCE: 22
ctctctcaaa cggcctttcc                                              20

<210> SEQ ID NO 23
<211> LENGTH: 31
<212> TYPE: DNA
<213> ORGANISM: Artificial Sequence
<220> FEATURE:
<223> OTHER INFORMATION: Unidirectional DNA fragment

<400> SEQUENCE: 23
ctctctcaaa cggcctttcc gaatgctaac t                                 31

<210> SEQ ID NO 24
<211> LENGTH: 31
<212> TYPE: DNA
<213> ORGANISM: Artificial Sequence
<220> FEATURE:
<223> OTHER INFORMATION: Oligonucleotide primer

<400> SEQUENCE: 24
cccaagcttc ctctcggaat aaaggaatca g                                 31

<210> SEQ ID NO 25
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 25
ttcaccgaac cgacgaagcg at                                           22

<210> SEQ ID NO 26
<211> LENGTH: 25
<212> TYPE: DNA
<213> ORGANISM: Artificial Sequence
<220> FEATURE:
<223> OTHER INFORMATION: Primer csn-XbaI

<400> SEQUENCE: 26
gctctagaca ttttatgtag taagc                                        25

<210> SEQ ID NO 27
<211> LENGTH: 23
<212> TYPE: DNA
<213> ORGANISM: Artificial Sequence
<220> FEATURE:
<223> OTHER INFORMATION: Primer csn-c1

<400> SEQUENCE: 27
ccggaattcg tatgctaatt ccc                                          23
```